US009907791B2

(12) United States Patent
Welm et al.

(10) Patent No.: US 9,907,791 B2
(45) Date of Patent: Mar. 6, 2018

(54) RON INHIBITORS FOR USE IN PREVENTING AND TREATING BONE LOSS

(71) Applicant: UNIVERSITY OF UTAH RESEARCH FOUNDATION, Salt Lake City, UT (US)

(72) Inventors: Alana L. Welm, Salt Lake City, UT (US); Kelsi Kretschmann Andrade, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/122,353

(22) PCT Filed: Mar. 13, 2015

(86) PCT No.: PCT/US2015/020479
§ 371 (c)(1),
(2) Date: Aug. 29, 2016

(87) PCT Pub. No.: WO2015/138925
PCT Pub. Date: Sep. 17, 2015

(65) Prior Publication Data
US 2016/0367534 A1    Dec. 22, 2016

Related U.S. Application Data

(60) Provisional application No. 61/953,309, filed on Mar. 14, 2014.

(51) Int. Cl.
*A61K 31/444* (2006.01)
*A61K 31/4355* (2006.01)

(52) U.S. Cl.
CPC ........ *A61K 31/444* (2013.01); *A61K 31/4355* (2013.01)

(58) Field of Classification Search
CPC .................................................. A61K 31/444
See application file for complete search history.

(56) References Cited

U.S. PATENT DOCUMENTS

| 2007/0117802 | A1  | 5/2007 | Borzilleri et al. |
| 2009/0197864 | A1* | 8/2009 | Li ................. C07D 491/048 514/210.21 |
| 2010/0204122 | A1  | 8/2010 | Huang |
| 2013/0089554 | A1  | 4/2013 | Blankenship et al. |

FOREIGN PATENT DOCUMENTS

WO    2013/173745    11/2013

OTHER PUBLICATIONS

Steing et al (Abstract 2915; Proceedings: AACR 103rd Annual Meeting 2012—Mar. 31-Apr. 4, 2012; Chicago, IL).*
Khan (Can. Fam Physician 2006: 743-747).*
Welm et al. (PNAS (2007); 104(18), 7570-7575).*
ClinicalTrials.gov (2008).*
Correll et al., "Deregulated inflammatory response in mice lacking the STK/RON receptor tyrosine kinase," Genes Funct., 1997, 1, 69-83.
Cui et al., "Lessons from (S)-6-(1-(6-(1-Methyl-1H-pyrazol-4-yl)-[1,2,4]triazolo[4,3-b]pyridazin-3-yl)ethyl)quinoline (PF-04254644), an Inhibitor of Receptor Tyrosine Kinase c-Met with High Protein Kinase Selectivity but Broad Phosphodiesterase Family Inhibition Leading to Myocardial Degeneration in Rats," J. Med. Chem., 2013, 56, 6651-6665.
Forrester et al., "Effect of conditional knockout of the type II TGF-beta receptor gene in mammary epithelia on mammary gland development and polyomavirus middle T antigen induced tumor formation and metastasis," Cancer Res., 15 2005, 65, 2296-302.
Gao et al., "Study of critical role of c-Met and its inhibitor SU11274 in colorectal carcinoma," Med. Oncol., 2013, 30, 546.
International Search Report and Written Opinion for Application No. PCT/US2015/020479 dated Jun. 16, 2015 (11 pages).
Kawada et al., "Dramatic antitumor effects of the dual MET/RON small-molecule inhibitor LY2801653 in non-small cell lung cancer," Cancer Res., 2014, 74, 884-895.
Molife et al., "A Phase I, Dose-Escalation Study of the Multitargeted Receptor Tyrosine Kinase Inhibitor, Golvatinib, in Patients With Advanced Solid Tumors," Clin. Cancer Res., 2014, 20, 6284-6294.
Northrup et al., "Discovery of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide (MK-8033): A Specific c-Met/Ron Dual Kinase Inhibitor with Preferential Affinity for the Activated State of c-Met," J. Med. Chem., 2013, 56, 2294-2310.
Parfitt, et al., "Bone histomorphometry: standardization of nomenclature, symbols, and units. Report of the ASBMR Histomorphometry Nomenclature Committee," J. Bone Miner. Res., 1987, 2, 595-610.
Rho et al., "MET and AXL inhibitor NPS-1034 exerts efficacy against lung cancer cells resistant to EGFR kinase inhibitors because of MET or AXL activation," Cancer Res., 2014, 74, 253-262.
Schroeder et al., "Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily," J. Met Chem., 2009, 52, 1251-1254.
Shah et al., "Phase II Study Evaluating 2 Dosing Schedules of Oral Foretinib (GSK1363089), cMET/VEGFR2 Inhibitor, in Patients with Metastatic Gastric Cancer," PLoS One, 2013, 8, e54014.
Spence et al., "Regional Osteoporosis in Osteoma," The Journal of Bone and Joint Surgery, 1961, vol. 43 B, No. 3, 501-507.
Steinig et al., "Novel 6-aminofuro[3,2-c]pyridines as potent, orally efficacious inhibitors of cMET and RON kinases," Bioorg. Met Chem., 2013, 23, 4381-4387.

(Continued)

*Primary Examiner* — Shirley V Gembeh
(74) *Attorney, Agent, or Firm* — Michael Best & Friedrich LLP

(57) ABSTRACT

Provided herein are methods for inhibiting osteolysis or treating osteoporosis in a subject in need thereof, the method including administering to the subject at least one RON inhibitor. The osteolysis may be caused by a condition selected from the group consisting of cancer, inflammation, and cyst. The condition may include a bone tumor or a tumor located in bone. The subject may have been diagnosed with bone cancer. The inhibitor may be ASLAN002. The inhibitor may be OSI-296. The inhibitor may be selective or specific for RON. The inhibitor may not depend on the function of RANKL or TGFβ.

10 Claims, 53 Drawing Sheets

(56) References Cited

OTHER PUBLICATIONS

Waltz et al., "Ron-mediated cytoplasmic signaling is dispensable for viability but is required to limit inflammatory responses," J. Clin. Invest., 2001, 108, 567-76.
Wang et al., "Synthesis and c-Met Kinase Inhibition of 3,5-Disubstituted and 3,5,7-Trisubstituted Quinolines: Identification of 3-(4-Acetylpiperazin-1-yl)-5-(3-nitrobenzylamino)-7-(trifluoromethyl)quinoline as a Novel Anticancer Agent," J. Med. Chem., 2011, 54, 2127-2142.
Welm, et al., "MET and MYC cooperate in mammary tumorigenesis," Proc. Natl. Acad. Sci. USA, 2005, 102, 4324-9.
Yasuda et al., "Preclinical rationale for use of the clinically-available multitargeted tyrosine kinase inhibitor crizotinib in ROS1 translocated lung cancer," J. Thorac. Oncol., 2012, 7, 1086-1090.
Zhang et al., "Identification of a Novel Recepteur d'Origine Nantais/C-Met Small-Molecule Kinase Inhibitor With Antitumor Activity in Vivo," Cancer Res., 2008, 68, 6680-6687.

\* cited by examiner

D

Normal bones

RON INHIBITORS FOR USE IN PREVENTING AND TREATING BONE LOSS

CROSS-REFERENCE TO RELATED APPLICATIONS

This is a U.S. national stage entry of International Patent Application No. PCT/US2015/020479, filed on Mar. 13, 2015, which claims priority to U.S. Provisional Patent Application No. 61/953,309, filed on Mar. 14, 2014, the entire contents of all of which are fully incorporated herein by reference.

STATEMENT REGARDING FEDERALLY SPONSORED RESEARCH

This invention was made with government support under Grant Numbers W81XWH-08-1-0109 and W81XWH-10-1-0366 awarded by ARMY/MRMC—Medical Research and Materiel Command. The government has certain rights in the invention.

BRIEF DESCRIPTION OF SEQUENCE LISTING

The instant application contains a Sequence Listing which has been submitted in ASCII format via EFS-Web and is hereby incorporated by reference in its entirety. Said ASCII copy, created on Aug. 22, 2016, is named U-5628-026389-9117-US01-SEQ-LIST-08-29-16.txt, and is 38,980 bytes in size.

FIELD

This disclosure relates to compositions and methods for inhibiting osteolysis or treating osteoporosis.

INTRODUCTION

Over 70% of patients with metastatic breast cancer have bone metastases. These metastases cause a number of complications including severe pain, nerve compression, hypercalcemia, and debilitating bone fractures. The development and growth of bone metastases depend on the interactions between tumor cells and cells within the bone microenvironment. Bone homeostasis is normally maintained by balanced osteoclast and osteoblast activities, and it is the ability of tumor cells to disrupt this delicate balance that results in bone destruction and metastatic tumor growth. The "vicious cycle" hypothesis describes the complex interactions that result in bone destruction and subsequent metastatic tumor growth. As active osteoclasts resorb bone, growth factors such as TGFβ are released from the bone matrix into the bone-tumor microenvironment. Such growth factors not only increase survival and proliferation of the metastatic tumor cells, but also lead to production of factors such as parathyroid hormone-related peptide and interleukin 11. These factors indirectly lead to further osteoclast differentiation and activation by stimulating secretion of receptor activator of nuclear factor-kB ligand (RANKL) from osteoblasts. RANKL is a key mediator of osteoclastogenesis and osteoclast activity, thus completing the cycle of bone resorption and metastatic tumor growth. Although several molecular contributors of bone metastasis have been identified, of which RANKL is key, identification of other targetable pathways may lead to additional therapies and/or more effective therapeutic combinations.

SUMMARY

In an aspect, the disclosure relates to methods for inhibiting osteolysis or for treating osteoporosis in a subject in need thereof. The methods may include administering to the subject at least one RON inhibitor.

The disclosure provides for other aspects and embodiments that will be apparent in light of the following detailed description and accompanying Figures.

BRIEF DESCRIPTION OF THE DRAWINGS

FIG. 1 shows that MSP increases tumor-driven osteolysis through host Ron activity.

FIG. 2 shows that RON is required for tumor-driven osteolysis of human breast cancer.

FIG. 3 shows that RON inhibition reduces MSP tumor-induced osteolysis in prophylactic and adjuvant settings.

FIG. 4 shows that MSP tumor-induced osteolysis is not dependent on RANKL or TGFβ signaling.

FIG. 5 shows that expression of MSP in human breast cancer increases tumor-induced osteolysis and overrides dependence on RANKL signaling.

FIG. 6 shows that MSP promotes osteoclast activity and survival through activation of Src and Akt signaling pathways.

FIG. 7 shows that loss of RON activity protects from osteoporotic bone loss.

FIG. 14B is a chart of the expression of MSP in lung carcinomas.

µM of the Src inhibitor AZD0530 added daily.

DETAILED DESCRIPTION

Figure 1A:
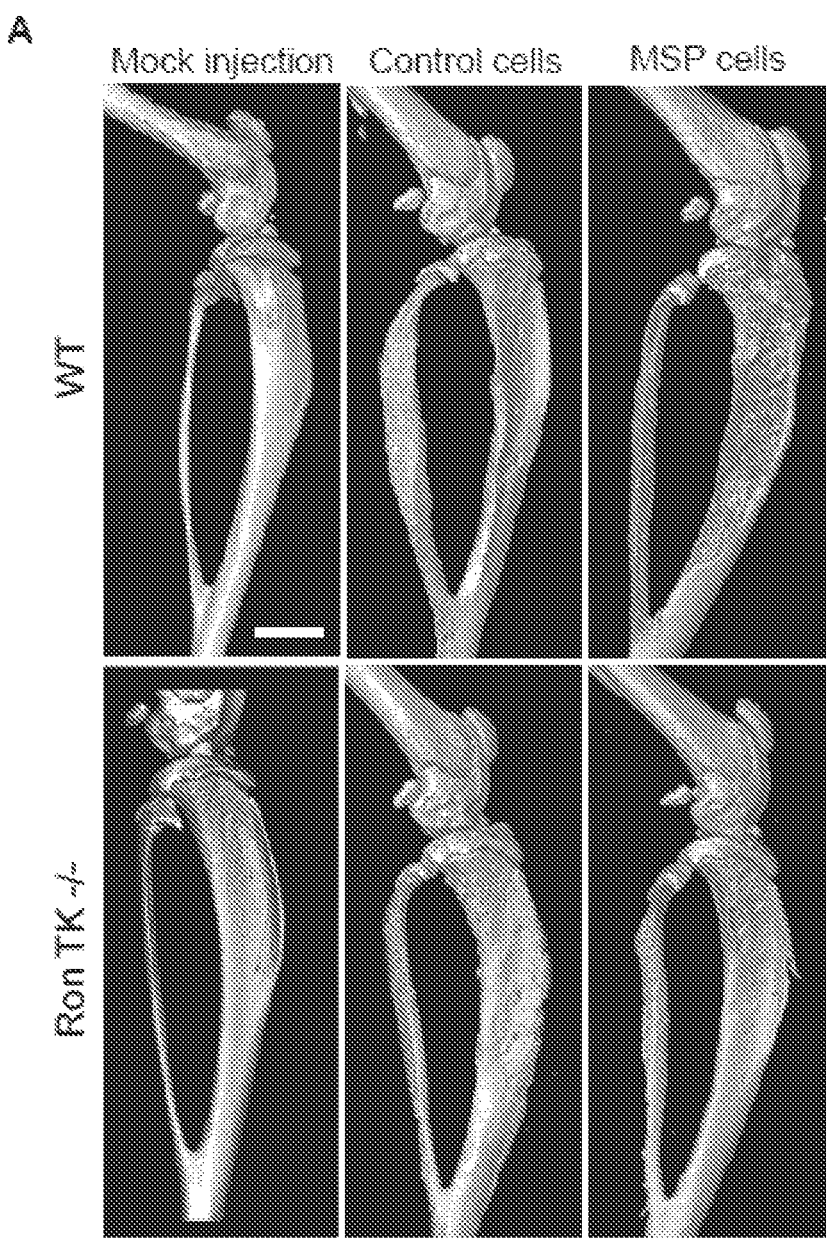
FIG. 1A is a series of microcomputed tomography (μCT) scans of bone lesions in the tibias of both wild-type (WT) mice, and mice in which the tyrosine kinase domain of RON had been deleted from the genome (RonTK−/−), 21 days post tumor cell injection.

The present disclosure relates to the discovery that the RON ligand, macrophage-stimulating protein (MSP), is an important mediator of tumor-driven osteolysis. Macrophage-stimulating protein (MSP, also known as human MST1 or mouse (hepatocyte growth factor like) HGFL) is a plasminogen-related growth factor that was originally identified as a serum protein that caused macrophage chemotaxis and activation. MSP is secreted as an inactive single-chain precursor (pro-MSP), which becomes active after proteolytic cleavage, forming a disulfide-linked heterodimer. The first protease identified to activate pro-MSP under biological conditions was membrane-type serine protease 1 (MT-SP1, also known as ST14 or matriptase). However, there are other proteases capable of pro-MSP maturation such as hepsin, human airway trypsin-like protease (HAT), and hepatocyte growth factor activator (HGFA). MSP exerts several biological effects depending on the cell type in which its receptor, macrophage-stimulating-1 receptor (MST1R, or RON), becomes activated. MSP is the only known ligand for RON, and RON is one of only two members of a distinct receptor tyrosine kinase family that also includes Met. RON is expressed in many tissues during development; however, in adults its expression is restricted to certain epithelial-derived cells (such as keratinocytes), nociceptive neurons, resident tissue macrophages, and osteoclasts. MSP can promote migration and survival of epithelial cell lines and can promote an epithelial-to-mesenchymal transition in immortalized canine kidney cells in vitro.

In addition to the effects the MSP/RON pathway has in a normal cellular context, the MSP/RON pathway may have a role in cancer. RON is expressed at high levels in many different epithelial cancers as well as malignancies of brain and bone. MSP and RON are coordinately overexpressed in over 20% of human breast cancers, and their overexpression along with matriptase has been shown to be an independent prognostic indicator for metastasis and poor survival. Overexpression of RON in breast epithelial cells leads to the transformation of cell lines and metastatic tumor development in mice. Overexpression of MSP in tumor cells driven by the polyomavirus middle T antigen under the control of the mouse mammary tumor virus promoter (MMTV-PyMT) led to spontaneous metastasis to bone and a significant increase in metastasis to other organs. MSP is sufficient to promote spontaneous metastasis to bone, yet spontaneous bone metastasis had been previously very difficult to achieve in genetically engineered mouse models. The bone metastases that developed in this model were osteolytic, replicating what is most commonly seen in human breast cancer patients. Interestingly, the overexpression of RON in mammary tumors did not lead to an increase in bone metastasis, suggesting a non-cell autonomous mechanism where tumor-host interactions may play a key role in MSP-driven bone metastasis.

Despite evidence supporting an oncogenic and bone metastatic role in breast cancer, the role of the RON receptor tyrosine kinase pathway in the bone microenvironment during metastasis has remained unknown. As disclosed herein, the inventors discovered that the RON ligand, macrophage-stimulating protein (MSP), is an important mediator of tumor-driven osteolysis. MSP overexpression leads to a significant increase in the ability of tumor cells to destroy bone and this ability requires RON activity in host osteoclasts. MSP-driven osteoclast activation does not require RANKL or TGFβ signaling and, importantly, pharmacological inhibition of RON can prevent both the development of osteolysis and the progression of existing osteolysis. In addition, the MSP/RON pathway is pertinent to other cases of pathogenic osteoclast activation; this pathway also functions in bone loss due to osteoporosis. These findings elucidate an important role for the MSP/RON pathway in osteoclast activation, providing rationale for the use of RON inhibitors for treatment of bone destruction in the setting of metastatic cancer or osteoporosis.

1. DEFINITIONS

The terms "comprise(s)," "include(s)," "having," "has," "can," "contain(s)," and variants thereof, as used herein, are intended to be open-ended (i.e., meaning "including but not limited to") transitional phrases, terms, or words that do not preclude the possibility of additional acts or structures unless otherwise noted. The use of the terms "a" and "an" and "the" and similar referents in the context of describing the invention are to be construed to cover both the singular and the plural, unless otherwise indicated herein or clearly contradicted by context. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" or "administering" refers to delivery of an inhibitor by any appropriate route to achieve the desired effect. Administration may include, but is not limited to, oral, sublingual, intramuscular, subcutaneous, intravenous, transdermal, topical, parenteral, buccal, rectal, and via injection, inhalation, and implants.

As used herein "cancer" refers to abnormal cell growth. A cancer cell may have the potential to invade or spread to other parts of the body. Cancer may include a malignant tumor or malignant neoplasm. Cancer is a subset of neoplasms, wherein a neoplasm is a group of cells that have undergone unregulated growth, and will often form a mass or lump, but may be distributed diffusely. "Metastasis" or "metastatic disease" refers to the spread of a cancer or disease from one organ or part to another not directly connected with it. The new occurrences of cancer thus generated are referred to as "metastases," a "secondary tumor," or "metastatic tumor." Cancer may include, for example, cancer of the skin, breast, prostate, lung, pancreas, colon, bone, bladder, rectum, stomach, esophagus, trachea, throat, head, neck, liver, kidney, brain, thyroid, heart, testicle, ovary, and cervix. Cancer may include carcinoma (derived from epithelial cells), sarcoma (derived from connective tissue), lymphoma (derived from hematopoietic cells), leukemia (derived from hematopoietic cells), blastoma (derived from immature "precursor" cells or embryonic tissue), or germ cell tumor (derived from pluripotent cells). In some embodiments, cancer includes bone cancer. In some embodiments, cancer includes a bone tumor or a tumor located in bone.

As used herein, an "effective amount" or "an amount sufficient to" achieve a particular result in a subject refers to an amount of a therapeutic agent (e.g., a RON inhibitor) that is effective to produce a desired effect, which is optionally a therapeutic effect (i.e., by administration of a therapeutically effective amount). In some aspects, such particular result is a reduction in osteolysis in a patient in need thereof. In some aspects, such particular result is a reduction in osteoporosis in a patient in need thereof. The progression from normal cells to cells that can form a discernible mass to outright cancer involves multiple steps known as malignant progression.

"Inhibitor" refers to an agent that inhibits the activity of one or more proteins. For example, an inhibitor may indirectly inhibit the activity of a protein by inhibiting the expression of the protein. An another example, an inhibitor may indirectly or directly bind and inhibit the activity of the protein, including catalytic activity or binding activity such as the ability of the protein to mediate binding to its target. An inhibitor is said to competitively inhibit binding of a protein if it preferentially binds to that protein to the extent that it blocks, to some degree, activity of the protein. Competitive inhibition can be determined by any method known in the art, for example, competition ELISA assays, competition binding assays, activity assays over a range of concentrations, or behavioral assays. An inhibitor can be said to inhibit a protein by at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, or at least 20%.

"Selective inhibitor" as used herein refers to an inhibitor whose activity on, for example, a protein, is greater relative to its activity on another protein under selected conditions. An inhibitor is said to be "selective" for a protein, for example, when it inhibits the activity of that protein more effectively than it would inhibit the activity of a random, unrelated protein, or even a similar or related protein having analogous but distinct function. The relative inhibition of a protein may be quantified by, for example, $IC_{50}$, $EC_{50}$, or $K_d$ values, among others. $IC_{50}$ values may be determined, for example, using Invitrogen Omnia (Waltham, Mass.). The terms "specific" and "selective" may be used interchangeably herein.

"Physiological conditions" refers to conditions of an assay or reaction that may occur in nature for that organism or cell system. Physiological conditions may include a temperature of between about 20-40° C. and a pH of between about 6-8. For example, physiological conditions may include an aqueous buffered solution at a pH of 7.2-7.6 and a temperature of about 37° C.

"Menopause" or "menopausal subject" refers to a condition in a woman when her menstrual periods stop and she is no longer able to have children. "Premenopause" or "premenopausal subject" refers to the years leading up to the last period, when the levels of reproductive hormones are already becoming more variable and lower, and the effects of hormone withdrawal are present. "Postmenopause" or "postmenopausal subject" refers to a condition in a woman who has not experienced any menstrual flow for a minimum of 12 months, assuming that she does still have a uterus, is not pregnant or lactating. In women without a uterus, menopause or postmenopause can be identified by a blood test showing a very high FSH level. Thus postmenopause is all of the time in a woman's life that takes place after her last period, or more accurately, all of the time that follows the point when her ovaries become inactive.

"Osteoporosis" as used herein is a progressive bone disease that is characterized by a decrease in bone mass and density. Osteoporosis can lead to an increased risk of fracture. Osteoporosis includes primary type 1, primary type 2, and secondary osteoporosis. As used herein, "treating osteoporosis" includes preventing osteoporosis, reducing the progression of osteoporosis, inhibiting osteolysis, or inhibiting osteoclasts, or a combination thereof.

"Osteolysis" refers to an active resorption of bone matrix by osteoclasts. Osteolysis can occur during the natural formation of healthy bones. Osteolysis often occurs in the proximity of a prosthesis and can cause an immunological response or changes in the bone's structural load. Osteolysis may be caused by a condition including, but not limited to, tumor, inflammation, hormone changes such as menopause, or cyst, or a combination thereof. In some embodiments, the tumor comprises metastatic cancer. In some embodiments, the tumor comprises a bone tumor and/or a tumor located in bone.

"Subject" or "patient" as used herein can mean any subject, particularly a mammalian subject, that wants to or is in need of being treated with the herein described therapeutic composition. A subject can be an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human. In some embodiments, the subject is a mammal. In further embodiments, the mammal is a human. In further embodiments, the mammal is a female human. In some embodiments, the subject is diagnosed with cancer. In some embodiments, the subject is diagnosed with bone cancer. In some embodiments, the subject is diagnosed with osteoporosis.

As used herein the terms "treat," "treatment," or "treatment of" in the context of treating a condition, pertains generally to treatment and therapy, whether of a human or an animal (e.g. in veterinary applications), in which a desired therapeutic effect is achieved. "Treatment" or "treating" means preventing, inhibiting the progress (e.g., reduce the rate of progress or halt the rate of progress), suppressing, repressing, ameliorating, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing or ameliorating the disease involves administering a composition of the present invention to an animal after clinical appearance of the disease.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

2. RON

Recepteur d'origine nantais (RON or Ron) belongs to a subfamily of receptor tyrosine kinases. RON is encoded by the MST1R gene. RON is also known as macrophage-stimulating protein receptor. RON is activated by a serum-derived growth factor macrophage stimulating protein (MSP). RON gene transcription is essential for embryonic development and critical in regulating certain physiological processes. Activation of RON leads to the activation of common receptor tyrosine kinase downstream-signaling pathways, such as activation of MAPK, PI3K, RAS-ERK, and beta-catenin. Furthermore, Ron participates in crosstalk with other signaling pathways such as Insulin-like growth factor 1 (IGF1R) and EGF receptor (EGFR) that are common tumorigenic mechanisms. In some embodiments, RON may comprise an amino acid sequence consisting of SEQ ID NO: 1, which is encoded by a polynucleotide sequence of SEQ ID NO: 2.

3. MET

Met, also called c-Met and MET and hepatocyte growth factor receptor (HGFR), is a receptor tyrosine kinase. Met possesses tyrosine kinase activity and is a membrane receptor protein. The primary single chain precursor protein is post-translationally cleaved to produce the alpha and beta subunits, which are disulfide linked to form the mature receptor. Hepatocyte growth factor (HGF) is the only known ligand of Met. Met is normally expressed by cells of epithelial origin, while HGF is expressed in cells of mesenchymal origin or in transformed cells such as tumors. Upon HGF stimulation, Met induces several biological responses that collectively give rise to a program known as invasive growth. Met is also important for embryonic development and wound healing. In some embodiments, Met may comprise an amino acid sequence consisting of SEQ ID NO: 3, which is encoded by a polynucleotide sequence of SEQ ID NO: 4.

4. RON INHIBITOR

Provided herein are RON inhibitors and compositions comprising the same. RON inhibitors encompass agents that inhibit the activity of RON under physiological conditions. A RON inhibitor may also inhibit the activity of members of the RON pathway including, for example, MSP, MBD4, Src, and PI3K. The amount or the activity of the protein may be reduced or inhibited using a variety of techniques known in the art. For example, an inhibitor may indirectly or directly bind and inhibit the activity of the protein, including binding activity or catalytic activity. An inhibitor may inhibit the ability of the protein to interact with cellular and extracellular components. An inhibitor may prevent or reduce expression of the protein. For example, a therapeutic composition adapted to reduce the amount or the activity of the protein may comprise a small molecule inhibitor of the protein itself or of a binding partner, an antibody specific for the protein, or a siRNA. In some embodiments, the therapeutic composition may comprise a siRNA adapted to reduce the expression of the protein. RON inhibitors may include, but are not limited to, OSI-296 (Steinig et al. *Bioorg. Med. Chem.* 2013, 23, 4381-4387), ASLAN002 (also known as BMS-777607; Schroeder et al. *J. Med. Chem.* 2009, 52, 1251-1254), LCRF-0004, Ron8, golvatinib (Molife et al. *Clin. Cancer Res.* 2014, 20, 6284-6294), LY2801653 (Kawada et al. *Cancer Res.* 2014, 74, 844-895), PF-04254644 (Cui et al. *J. Med. Chem.* 2013, 56, 6651-6665), SU11274 (Gao et al. *Med. Oncol.* 2013, 30, 546), foretinib (GSK1363089; Shah et al. *PLoS One* 2013, 8, e54014), MK-8033 (Northrup et al. *J. Med. Chem.* 2013, 56, 2294-2310), 3,5-disubstituted and 3,5,7-trisubstituted quinolines (Wang et al. *J. Med. Chem.* 2011, 54, 2127-2142), Compound I (Zhang et al. *Cancer Res.* 2008, 68, 6680-6687), NPS-1034 (Rho et al. *Cancer Res.* 2014, 74, 253-262), crizotinib (Yasuda et al. *J. Thorac. Oncol.* 2012, 7, 1086-1090), and any other agents that inhibit the activity of or reduce the amount of RON.

In some embodiments, the inhibitor is OSI-296, shown below:

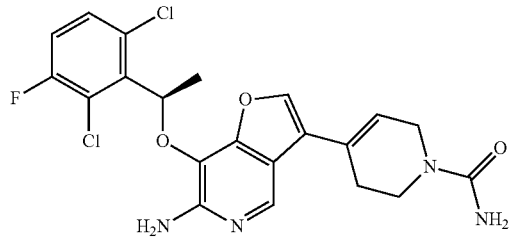

OSI-296

In some embodiments, the inhibitor is ASLAN002, shown below:

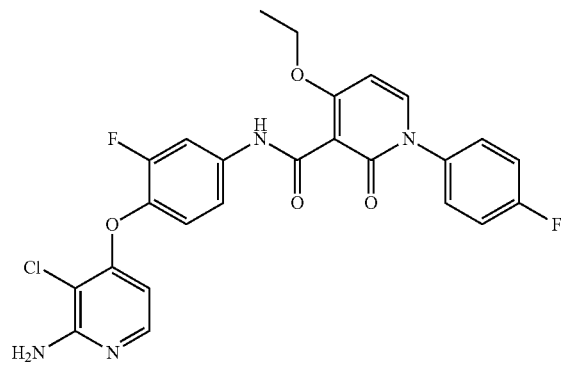

ASLAN002

In some embodiments, the inhibitor may act independently of the RANKL and/or TGFβ pathways. The inhibitor may not affect the function of RANKL and/or TGFβ. The inhibitor may not depend on the function of RANKL and/or TGFβ.

a. RON-Selective Inhibitor

The RON inhibitor may be selective or specific for RON. As used herein, a RON-selective inhibitor inhibits the activity of RON greater than it inhibits the activity of another protein, such as, for example, another receptor tyrosine kinase, under physiological conditions. Receptor tyrosine kinases other than RON include, for example, Met and Axl.

For example, a RON-selective inhibitor may inhibit RON greater than it inhibits Met under physiological conditions. For example, a RON-selective inhibitor may inhibit RON greater than it inhibits Axl under physiological conditions.

In some embodiments, a RON-selective inhibitor may inhibit the activity of RON at least about 2 times, at least about 3 times, at least about 4 times, at least about 5 times, at least about 10 times, at least about 15 times, at least about 20 times, at least about 25 times, at least about 50 times, or at least about 100 times more than it inhibits the activity of another receptor tyrosine kinase, such as Met. In some embodiments, a RON-selective inhibitor may have an $IC_{50}$ for another receptor tyrosine kinase that is at least about 2 times, at least about 3 times, at least about 4 times, at least about 5 times, at least about 10 times, at least about 15 times, at least about 20 times, at least about 25 times, at least about 50 times, or at least about 100 times greater than the $IC_{50}$ for RON. In some embodiments, the RON-selective inhibitor comprises ASLAN002.

5. METHODS OF USING THE RON INHIBITORS

RON inhibitors may be used to inhibit osteolysis or treat osteoporosis. The method includes administering to the subject at least one RON inhibitor. In some embodiments, the inhibitor is a RON-selective inhibitor.

A RON inhibitor may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

a. Methods for Inhibiting Osteolysis

Provided herein are methods for inhibiting osteolysis in a subject in need thereof. The method includes administering to the subject at least one RON inhibitor. In some embodiments, the inhibitor is a RON-selective inhibitor. Inhibiting osteolysis may include reducing bone turnover, reducing the progression of bone loss, inhibiting osteoclasts, or a combination thereof. In some embodiments, the subject has been diagnosed with a condition selected from inflammation, cyst, cancer, cancer with bone metastasis, and cancer-mediated bone destruction.

b. Methods for Treating Osteoporosis

Provided herein are methods for treating osteoporosis in a subject in need thereof. Treating osteoporosis may include preventing osteoporosis, reducing the progression of osteoporosis, or a combination thereof. The method includes administering to the subject at least one RON inhibitor. In some embodiments, the inhibitor is a RON-selective inhibitor.

All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims.

6. EXAMPLES

Example 1

Experimental Procedures

Tumor Injections and X-Ray Analysis.

All procedures involving mice and experimental protocols were approved by the Institutional Animal Care and Use Committee (IACUC) of the University of Utah. The RonTK−/− mice which reside on the FVB background, were crossed with NOD.SCID mice for an immune-compromised mouse model. As a control, wild-type FVB mice were also crossed with NOD.SCID mice. The STK−/− mice, which are on a C57BL/6 background, were compared to wild-type C57BL/6 mice as controls. Mice for all experiments were 6 to 8 weeks of age. For intratibial injections, $1\times10^5$ (PyMTor DU4475) or $3\times10^5$ (MDA-MB-231) tumor cells were resuspended in 10 μL matrigel and injected into the right tibia of anesthetized female FVB (PyMT) or NOD.SCID mice carrying various alleles of RON. Osteolysis was assessed by X-ray radiography. Dissected hindlimbs from mice sacrificed at the final time point in each experiment were placed in the Kodak In-vivo Multispectral Imaging System FX and exposed to X-ray radiography at 35 kV for 100 sec. Excess tumor tissue was removed from the bones prior to X-ray. Osteolytic lesions were quantified using Image J software (NCBI). All images were compared to the contralateral leg as an internal control.

Micro-Computed Tomography Imaging and Bone Mineral Density Measurements.

Representative samples were imaged by micro-computed tomography (μCT, Skyscan) with volume rendering snapshots of the tibia. For the osteoporosis study, representative samples were imaged and presented as volume rendering snapshots of the axial view of the tibial metaphysis region. For bone mineral density (BMD) measurements, the right tibia was removed and fixed in 10% NBF overnight. The tibia were then scanned by dual-energy X-ray absorptiometry (DXA) using a Norland pDEXA densitometer (Norland Medical Systems, White Plains, N.Y.). A region including the primary and secondary spongiosa was used to determine the BMD of the tibia.

Tissue Processing and Immunohistochemical Staining.

Hindlimb bones were excised from mice at the time of sacrifice and bones were fixed in 10% neutral-buffered formalin, decalcified in Formical-2000 (Decal Corporation, Tallman, N.Y.) for 8 days and embedded in paraffin for hematoxylin and eosin (H & E) or immunohistochemical staining. Osteoclast number was assessed as $TRAP^+$ multinucleated cells containing 4 or more nuclei and reported as $TRAP^+$ cells per field. Three sections per mouse and 5 fields per section were used for quantification with fields representing the entire length of the tibia. Tumor proliferation rate was reported as the number of cells which were positive for phospho-H3 staining compared to the number of unstained cells per field expressed as a percent. Three sections per mouse and 5 fields per section were used for quantification with analysis being restricted to within the bone marrow cavity. Immunohistochemical analysis was performed with heat-induced antigen retrieval in sodium-citrate buffer (Dako, Denmark). Primary antibodies used were anti-TRAP at 1:50 (Santa Cruz, sc-30833, Dallas, Tex.), anti-Ki67 at 1:100 (Santa Cruz, sc-12202S, Dallas, Tex.), anti-phosphoH3 at 1:100 (Cell Signaling, #9701, Beverly, Mass.), anti-NFATc1 at 1:50 (Santa Cruz, sc-13033, Dallas, Tex.), and anti-RON at 1:250 (Santa Cruz, sc-322, Dallas, Tex.).

Bones from mice lacking RON were used as a negative control. Biotinylated secondary antibody was used with the EnVision+ system HRP kit (Dako, Denmark) and nuclei counterstained with hematoxylin.

Recombinant MSP Production and Purification.

Briefly, human MSP was expressed in 293T cells following transduction with pMSCV-hMSP-Thrombin-His-V5 lentivirus, which also contained a hygromycin selection cassette. Secreted MSP was collected from serum-free supernatants, concentrated, and activated by incubation with kallikrein (Sigma, St. Louis, Mo.; K2638). The activated MSP was purified over a His-Talon column (Clontech, Mountain View, Calif.; 635651), washed, and concentrated using Amicon Ultra-15 Centrifugal Filter Devices. MSP protein concentration was quantified using a human MSP DuoSet ELISA kit (R&D Systems; DY352) on a custom MULTI-ARRAY MSD 96-well microplate platform (MesoScale Discovery, Rockville, Md.; L15XA-3) and read with the SECTOR Imager 2400. MSP specific activity was confirmed by quantifying the ability of MSP to cause phosphorylation of Ron expressed in MCF10A cells.

Plasmids and Retroviral Transduction of Osteoclast Precursors.

Wild-type Src was subcloned out of the pM5McSrc vector (Addgene plasmid 17685) by PCR and inserted into the pMSCV-puro vector (Clontech, Mountain View, Calif.) using the BglII 5' and EcoRI 3' restriction sites. The constitutively active Src mutant (Y529F) and the kinase dead Src mutant (Y529F+K297M) were generated using standard PCR techniques. A total of 5 ug of the pMSCV retroviral vectors were transfected into the 293T cell line using X-tremeGENE 9 transfection reagent (Roche Applied Science, Indianapolis, Ind.). Virus was collected 48 hours after post transfection. Ron TK−/− bone marrow precursor cells were infected with virus for 24 hours in the presence of 100 ng/mL M-CSF and 4 ug/mL Polybrene (Sigma, St. Louis, Mo.). Cells were selected in the presence of M-CSF and 1 ug/mL puromycin for 3 days prior to use as osteoclast precursors.

Osteoclast Resorption Assay.

Bone marrow osteoclasts were generated from 6 to 8 week old WT and RonTK−/− mice. Briefly, bone marrow was isolated from hindlimb bones and plated in α-MEM media containing 10% heat-inactivated fetal bovine serum (FBS, Sigma, St. Louis, Mo.), 100 units/mL penicillin-streptomycin (Hyclone), and 33 ng/mL human macrophage colony-stimulating factor (hM-CSF) (PeproTech, Rocky Hill, N.J.) for 24 hours. Non-adherent cells were collected and frozen for later use. To assess resorption activity, bone marrow precursor cells were thawed and seeded at a density of $1 \times 10^5$ cells per well in BioCoat Osteologic slides (BD Biosciences, San Jose, Calif.) in α-MEM media containing 10% FBS and antibiotics. After adhering overnight, media was removed and media containing 33 ng/mL hM-CSF and 9 ng/mL muRANKL (R & D systems, Minneapolis, Minn.) was added. The medium was changed every 3 days depending on acidification, and the assay was terminated as indicated. Recombinant human MSP was prepared and added daily as indicated. Cells were removed with 6% bleach and slides were viewed microscopically using phase-contrast with 20× magnification. Osteolytic resorption area within 5 representative fields was determined using Image J software, experiments were performed in triplicate. Recombinant MSP was prepared as follows (to be described in detail elsewhere): Concentrated, serum-free media from an MCF7 cell line engineered to overexpress MSP was cleaved with kallikrein (Invitrogen, Waltham, Mass.; 4 ng of kallikrein/1 μg of supernatant protein at 37° C. for 2.5 hours). The reaction was diluted to 20 mL with 10 mM sodium phosphate, pH 7.4 and loaded onto a 5 mL HiTrap heparin column (Millipore, Billerica, Mass.) equilibrated with 20 mL of 10 mM sodium phosphate, pH 7.4, at a rate of 1 mL/min. The column was washed with 10 mL of 10 mM sodium phosphate, pH 7.4, at a rate of 1 mL/min. The bound protein was eluted with 7 mL of serial concentrations of NaCl in 10 mM sodium phosphate, pH 7.4: 0.1 M, 0.15 M, 0.2 M, 0.25 M, 0.3 M, 0.35 M, 0.4 M, 0.45 M, and 2 M. Each fraction was collected and concentrated/desalted on a spin column. Each fraction was run for MSP western analysis and ELISA analysis to determine purity and concentration.

Osteoclast Survival Assay.

Bone marrow precursor cells were thawed and seeded at a density of $2 \times 10^5$ cells per well in a 24-well plate containing glass coverslips in α-MEM media containing 10% FBS and antibiotics. After adhering overnight, media was removed and media containing 33 ng/mL hM-CSF and 9 ng/mL muRANKL was added. Cells were allowed to differentiate for 7 days with media changed every 3 days. Coverslips were then imaged microscopically using phase contrast to determine osteoclast number in each well. To test survival, factor-containing media was removed and α-MEM media containing 10% FBS was added as well as MSP as indicated. Cells were cultured for an additional 48 hours, fixed with 10% NBF for 10 minutes and washed with 1×PBS. For TRAP fluorescent staining, the leukocyte acid phosphatase kit (Sigma, St. Louis, Mo.) was used according to the manufacturer's instructions, with the substitution of 200 μM ELF97 (Invitrogen, Waltham, Mass.) as a phosphatase substrate. Coverslips were incubated in TRAP solution for 15 minutes at 37 degrees, washed with 1×PBS and counterstained with DAPI. The number of multinucleated TRAP+ cells (containing 4 or more nuclei) within 5 representative fields were included for quantification. Experiments were performed in triplicate.

Murine RANKL ELISA.

Quantitative levels of murine RANKL in serum isolated from mice at the end-point of experiments were determined in triplicate by ELISA according to the manufacturer's protocol (Quantikine immunoassay kit, R & D systems, Minneapolis, Minn.).

Pharmacological Inhibition In Vitro and In Vivo.

For in vitro experiments, OSI-296 (OSI pharmaceuticals, Melville, N.Y.) and ASLAN002 (BMS-777607; Selleck, Houston, Tex.) were dissolved in DMSO. Inhibitors were added to in vitro osteoclast assays at a final concentration of 10 μM daily for 3 days beginning on day 9 of the experiment. muRANK-Fc (Amgen, Thousand Oaks, Calif.) was provided as a stock of 4.1 mg/mL in PBS and was added to in vitro assays at a final concentration of 10 μg/mL daily as indicated.

For in vivo experiments, the OSI-296 inhibitor was dissolved in 40% Trappsol with 0.01 M HCl, and mice were treated at a concentration of 200 mg/kg daily by oral gavage. Treatment began either 3 days after tumor cell injection for prophylactic experiments, or 3 weeks after tumor cell injection for therapeutic experiments. ASLAN002 was dissolved in 70% PEG400 with 1×PBS and mice were treated at a concentration of 50 mg/kg daily by oral gavage. muRANK-Fc was given at a concentration of 10 mg/kg every three days by intra-peritoneal injection. For the osteoporosis study, mice were treated beginning on the day after ovary removal. The treatment regimen for OSI-296 was 200 mg/kg every other day by oral gavage. ASLAN002 was administered at 50 mg/kg every other day by oral gavage. Treatment continued until the time of sacrifice at 28 days.

Cell Culture.

The DU4475 cell line (ATCC) was maintained in RPMI (Hyclone, GE Healthcare, Little Chalfont, UK) with 10% FBS and antibiotics. The MDA-MB-231 cell line (ATCC) was maintained in RPMI with 10% FBS, antibiotics, and HEPES (Sigma, St. Louis, Mo.). MC3T3-E1 subclone 4 cells (ATCC) were maintained in α-MEM with 10% FBS and antibiotics. PyMT tumors were isolated and transduced as previously described and frozen for later use (Welm, et al. Proc. Natl. Acad. Sci. USA 2005, 102, 4324-9; Welm, et al. Proc. Natl. Acad. Sci. USA 2007, 104, 7570-7575). Cells were thawed and grown for 2 to 3 days in DMEM/F12 with 10% FBS, antibiotics, insulin (Gibco, Life Technologies, Thermo Fisher, Waltham, Mass.), hydrocortisone, and epidermal growth factor prior to injections. MDA-MB-231 cells were transduced with replication-defective retroviruses containing the expression vector pMSCVpuro or MSCVpuro-MSP, and infected cells were selected with puromycin.

Western Blot Analyses.

Cells were serum starved (0.5% FBS) for 3 hours prior to lysate collection. Inhibitors were added 1 hour prior to lysis and MSP was added 15 min prior to lysis when indicated. Cells were washed with 1×PBS and harvested in lysis buffer (25 mM Tris-HCl, pH 7.5, 0.42 M NaCl, 1.5 mM $MgCl_2$, 0.5 mM EDTA, 1 mM DTT, 25% sucrose, and 0.1% Triton X-100) plus 100× protease arrest (Bioscience, Bozeman, Mont.) and 100× orthovanadate. Primary antibodies used for immunoblotting include: anti-MSP (Santa Cruz, sc-6090, Dallas, Tex.) at a 1:250 dilution, anti-pan Akt (Cell Signaling, #4691S, Beverly, Mass.) at a 1:1000 dilution, anti-pan Erk (Cell Signaling, #4695, Beverly, Mass.) at a 1:1000 dilution, anti-phospho Akt (Cell Signaling, #9271 L, Beverly, Mass.) at a 1:500 dilution, anti-phospho Erk (Cell Signaling, #4370S, Beverly, Mass.) at a 1:500 dilution, anti-Src (Cell Signaling, #2110, Beverly, Mass.) at a 1:500 dilution, and anti-phospho Src (Y416) (Cell Signaling, #2113, Beverly, Mass.) at a 1:500 dilution. The secondary antibodies used were HRP-conjugated anti-goat IgG (Santa Cruz, Dallas, Tex.) and anti-rabbit IgG (Santa Cruz, Dallas, Tex.). Chemiluminescent signals were detected using Immun-Star HRP (BioRad, Hercules, Calif.).

In Vivo Bone Labeling and Histomophometry.

To label bones, mice were intraperitoneally injected with 20 mg/kg of calcein (Sigma-Aldrich, St. Louis, Mo.) or 30 mg/kg of Alizarin Complexone (Sigma-Aldrich, St. Louis, Mo.) in a 2% sodium bicarbonate solution. Mice 6 to 8 months of age were labeled 8 days and 2 days prior to euthanasia, respectively. Tibia were fixed in 70% ethanol, embedded in methylmethacrylate and sectioned. Bone histomorphometry on H and E sections and bone labeled sections were performed as previously described (Parfitt, et al. Report of the ASBMR Histomorphometry Nomenclature Committee. J. Bone Miner. Res. 1987, 2, 595-610). Analysis of bone volume (BV/TV), and trabecular spacing (Tb. Sp.) were performed on the metaphyseal region of tibia sections stained with H and E. Bone formation rate (BFR) per bone surface (BS) and mineral apposition rate (MAR) of trabeculae were calculated within the metaphyseal region of the tibia. For all histomorphometry, three sections per mouse with 4 to 5 mice per group were analyzed. Analysis was performed using Bioquant Osteo software (Bioquant Image Analysis Corporation, Nashville, Tenn.).

Assessment of Human Plasma CTX and BSAP Levels.

All samples were de-identified and the experiments were approved by the University of Utah Institutional Review Board. Plasma samples were submitted to ARUP for clinical testing of CTX. For BSAP, the Human Bone Panel I capture plate with the Human Alkaline Phosphatase detection kit was utilized (Meso Scale Discovery, Rockville, Md.; K151HEC-2) to measure BSAP levels in undiluted plasma samples per the manufacturer's protocol.

Statistical Analysis.

Data are shown as mean+/− SEM. All experiments were analyzed using 2-tailed, unpaired, Student's t test using Prism 6 (GraphPad Software, La Jolla, Calif.).

Example 2

RON Expression in the Host is Required for MSP-Driven Breast Cancer Osteolysis

Figure 1B:
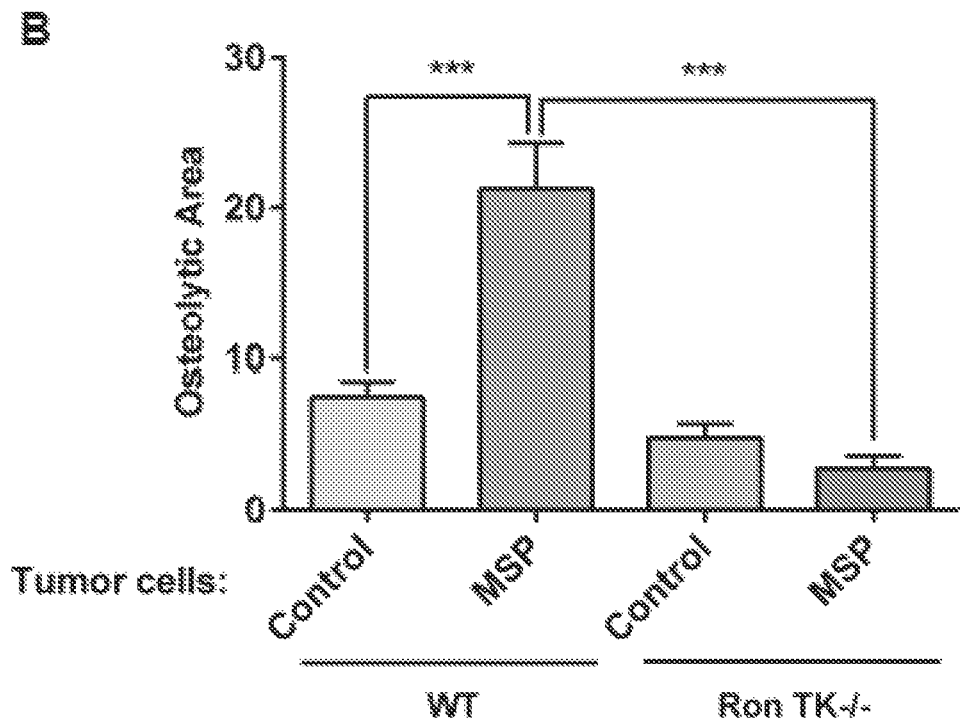
FIG. 1B is a bar chart showing the osteolytic area in tibias from WT and RonTK−/− mice ex vivo using high resolution X-ray analysis.
Figure 1C:
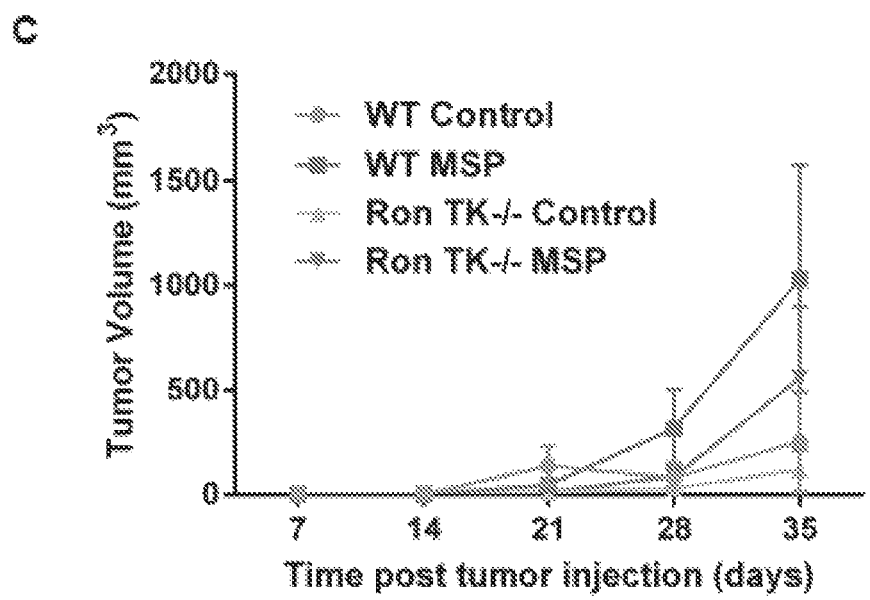
FIG. 1C is a graph of tumor volume in tibias, determined by caliper measurements, as a function of time.
Figure 1D:
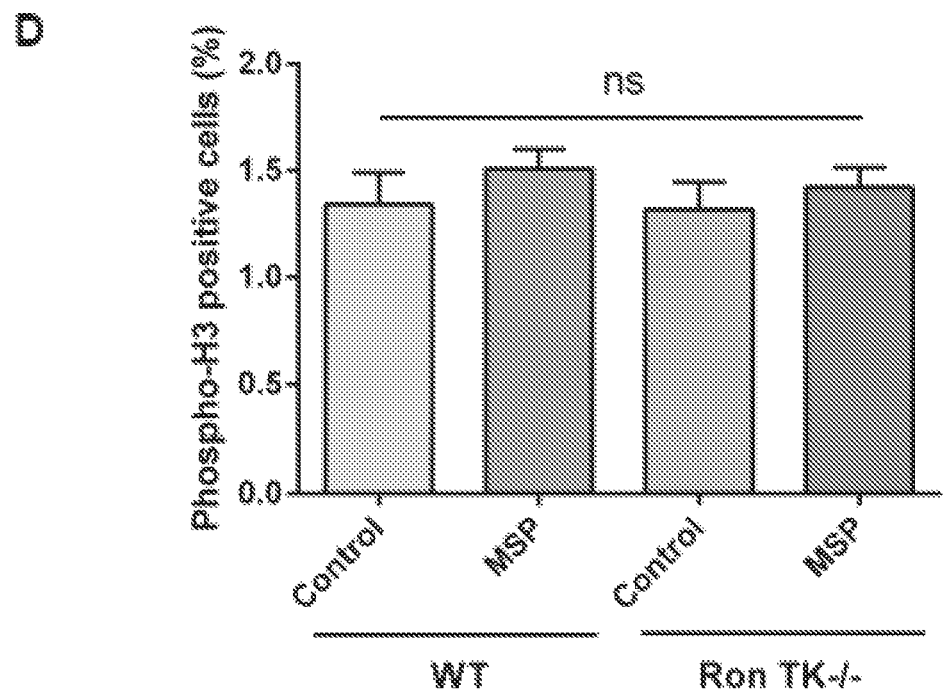
FIG. 1D is a bar chart showing the proliferation rate of PyMT control expressed as the percent of cells staining positive for phospho-H3 in various experimental groups.

MSP drives spontaneous osteolytic bone metastasis. To investigate whether MSP-mediated bone metastasis depends on non cell-autonomous activation of RON, PyMT or PyMT-MSP tumor cells were injected into the tibias of wild-type (WT) mice or mice in which the tyrosine kinase domain of RON had been deleted from the genome (RonTK−/−) (Waltz et al. J. Clin. Invest. 2001, 108, 567-76). Expression of MSP in the tumor cells significantly increased the ability of these tumors to induce osteolysis in WT bones (FIG. 1A). FIG. 1A shows Microcomputed tomography (µCT) of bone lesions in the tibia 21 days post tumor cell injection. (scale bar, 2 mm). In contrast, when tumors overexpressing MSP were injected into RonTK−/− bones, they induced very little osteolysis. This was comparable to the basal levels of osteolysis induced in control tumor cells, as FIG. 1B shows quantification of osteolytic area in tibias from mice ex vivo using high resolution X-ray analysis (n=10) 42 days post tumor cell injection (p<0.0005). MSP-driven osteolysis could not be explained by altered tumor growth in the bone, as no statistically significant differences in tumor size or proliferation were observed between cohorts (FIG. 1C and FIG. 1D). FIG. 1C shows tumor growth in tibias determined by caliper measurements, and FIG. 1D shows proliferation rate of PyMT control and MSP-expressing tumor cells expressed as the percent of cells staining positive for phospho-H3. This indicated that RON activity in the host was required for the ability of MSP expressing tumor cells to induce osteolysis in the bone microenvironment. The presence of residual tumor-induced osteolysis caused by control tumors both in WT and RonTK−/− mice demonstrated some degree of osteolysis that is independent of the MSP/RON pathway, likely RANKL-mediated (addressed below).

Figure 1E:
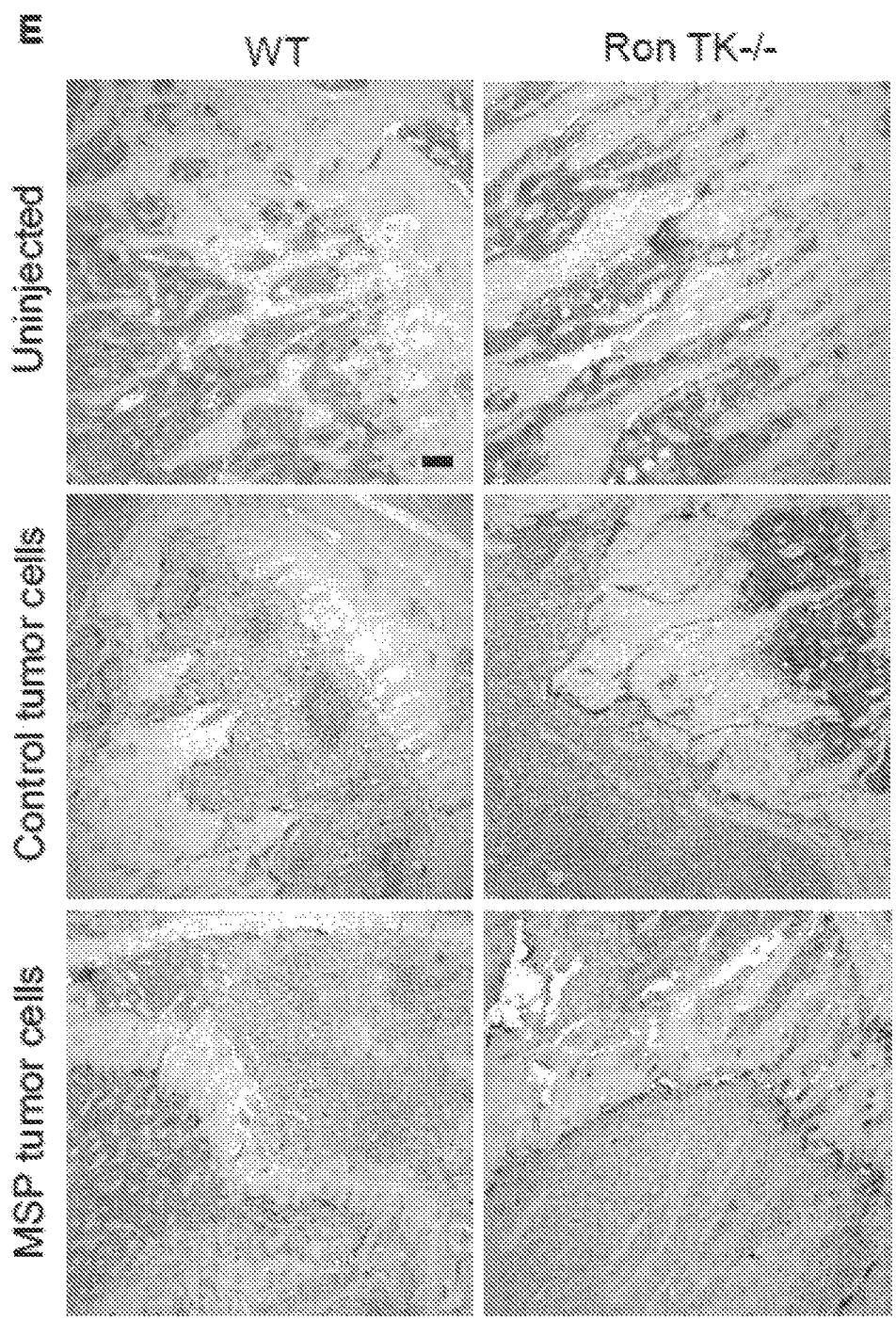
FIG. 1E is a series of images showing sections of tumor-bearing bones from various experimental groups.
Figure 1F:
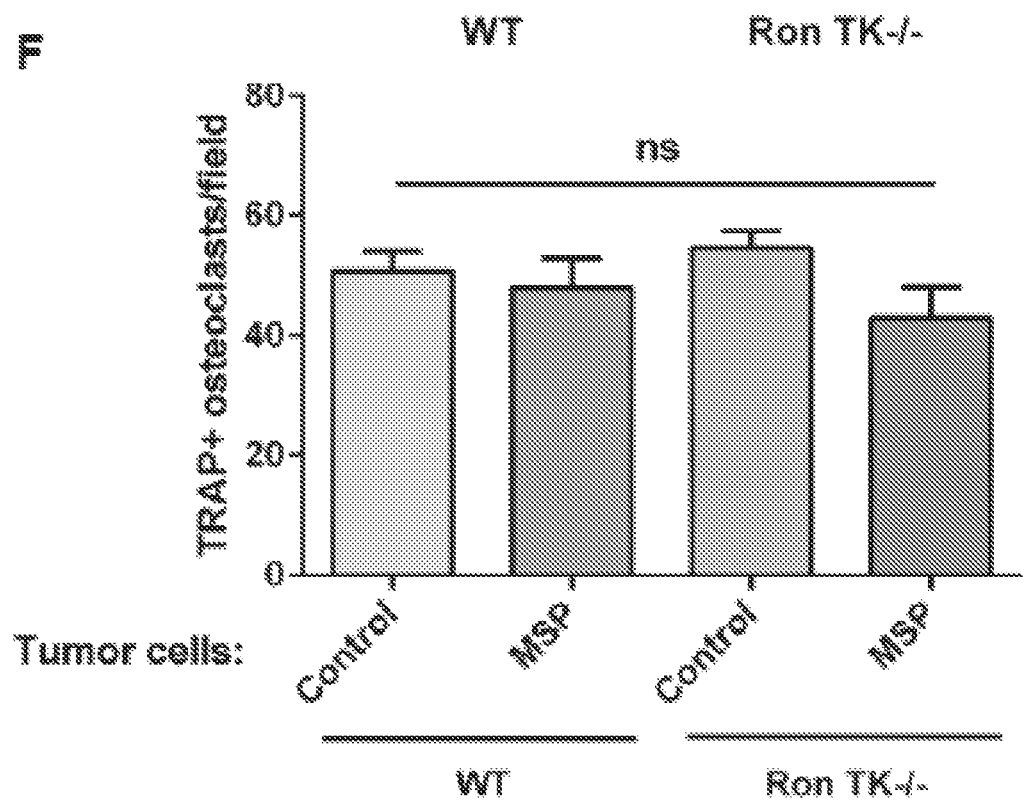
FIG. 1F is a bar chart of TRAP+ osteoclasts in various experimental groups.
Figure 8A:
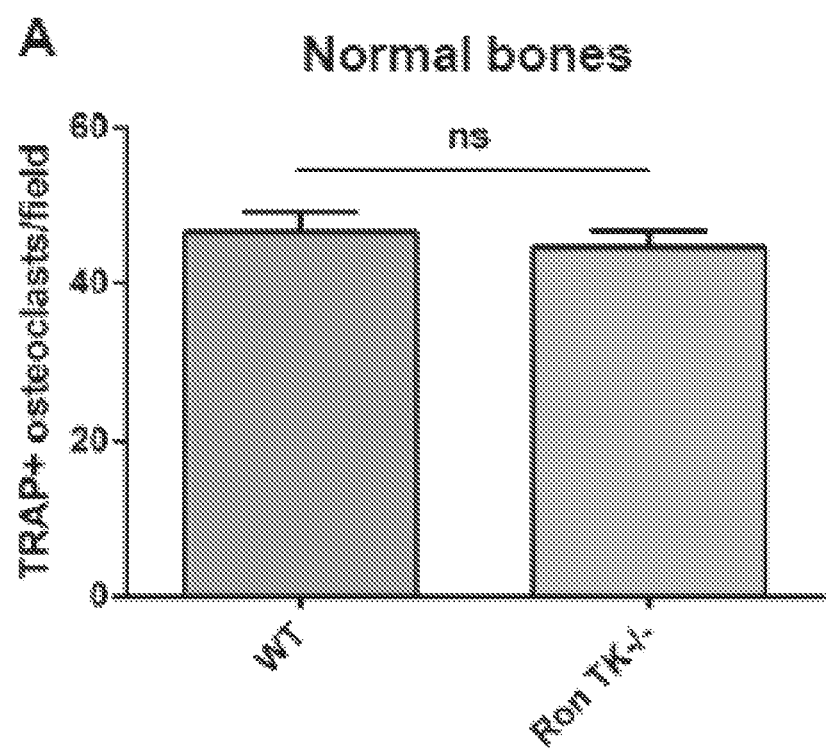
FIG. 8A is a bar chart showing TRAP+ osteoclasts from normal, uninjected WT and Ron TK−/− mice.

To determine if MSP-driven osteolysis was due to an increase in the number of osteoclasts present within the microenvironment, bone sections were stained for the osteoclast-specific protein tartrate resistant acid phosphatase (TRAP), and the number of TRAP-positive (TRAP+) multinuclear cells was quantified. No significant difference in the number of TRAP+ osteoclasts was detected when comparing bones harboring control tumors versus MSP expressing tumors (FIG. 1E and FIG. 1F). FIG. 1E shows TRAP staining on sections of tumor-bearing bones from each experimental group (scale bar, 100 µm), and FIG. 1F shows quantification of TRAP$^+$ osteoclasts in each experimental group (n=5-7 per group). Normal, non tumor-bearing bones were also examined to determine whether the RonTK−/− mice displayed a defect in osteoclastogenesis. Again, there was no difference in the number of osteoclasts present in the bones of RonTK−/− mice when compared to WT mice (FIG. 1E and FIG. 8A). FIG. 8A shows quantification of TRAP+ osteoclasts from normal, uninjected WT, and Ron TK−/− mice (n=5; ns=not significant).

Figure 8B:
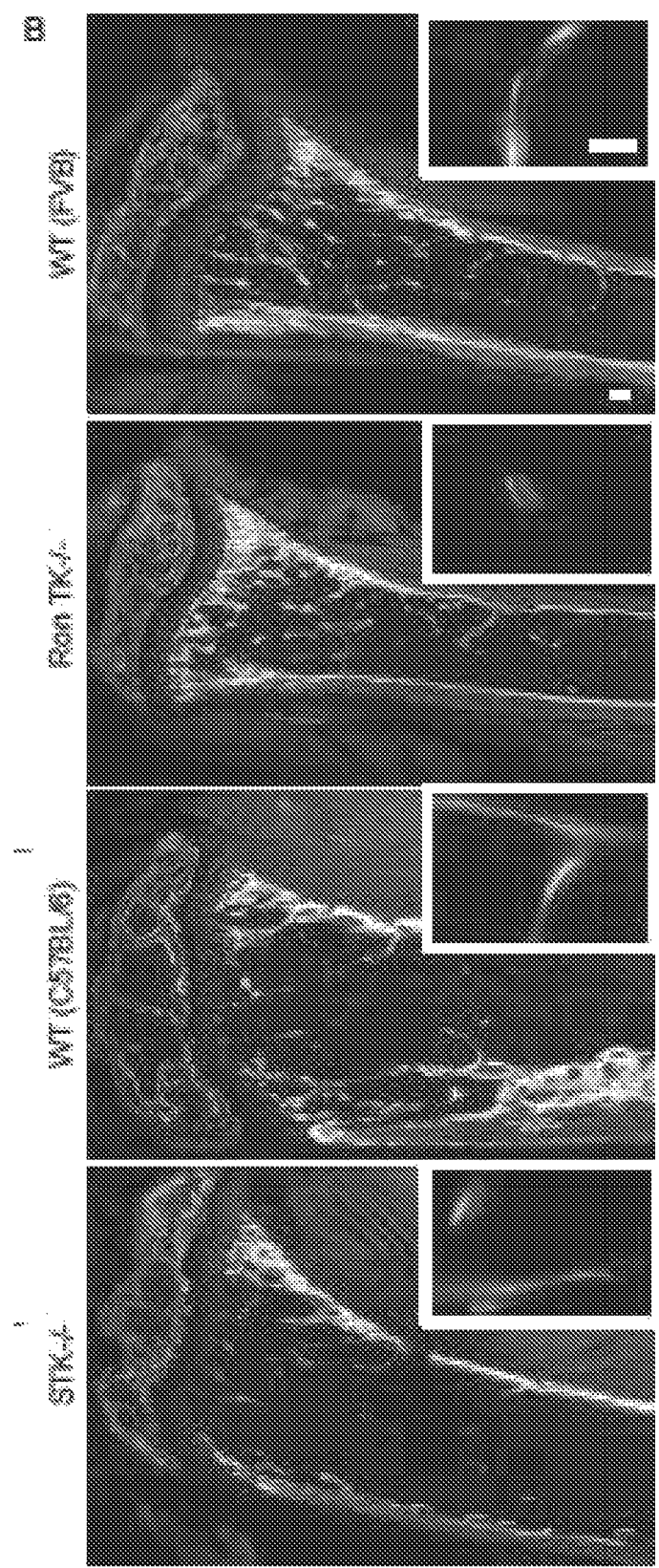
FIG. 8B is a series of images of bone formation as observed by calcein and Alizarin double labeling.
Figure 8C:
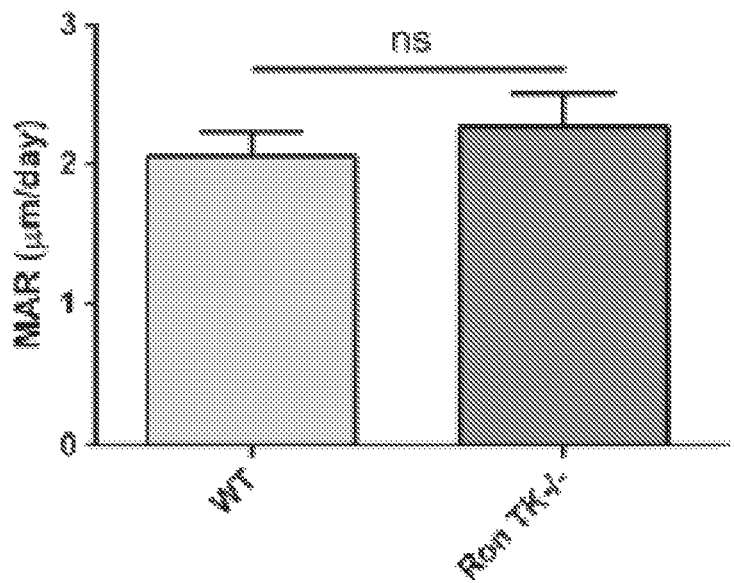
FIG. 8C is a bar chart showing mineral apposition rate determined by bone histomorphometric analysis in WT and RonTK−/− mice.
Figure 8D:
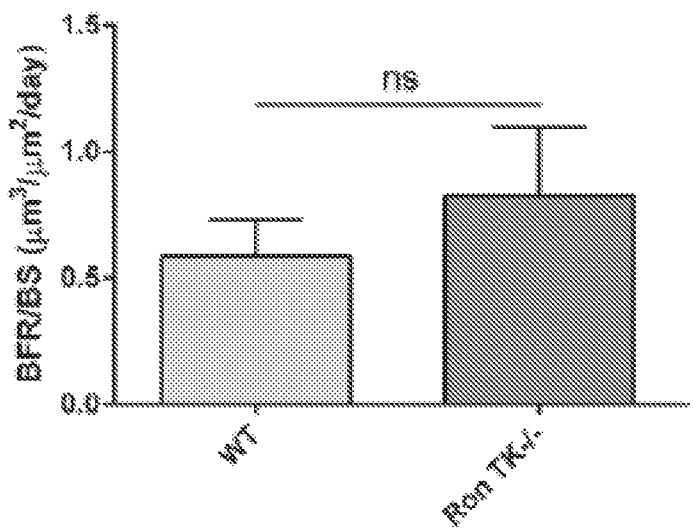
FIG. 8D is a bar chart showing bone formation rate per total bone surface in WT and RonTK−/− mice.
Figure 8E:
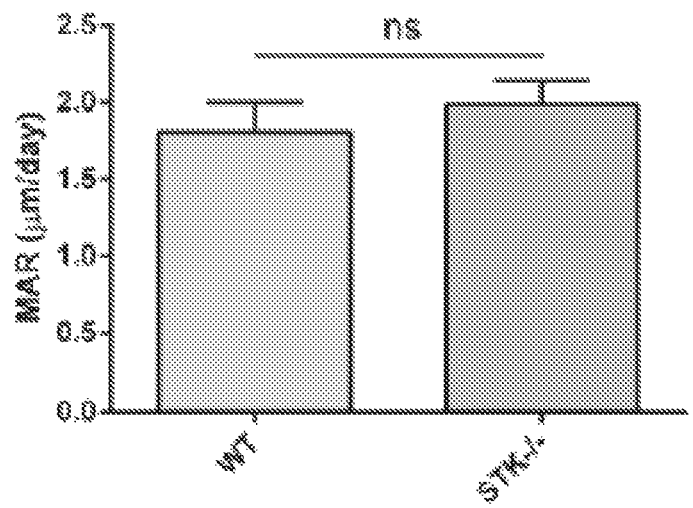
FIG. 8E is a graph of mineral apposition rate in WT and STK−/− mice.
Figure 8F:
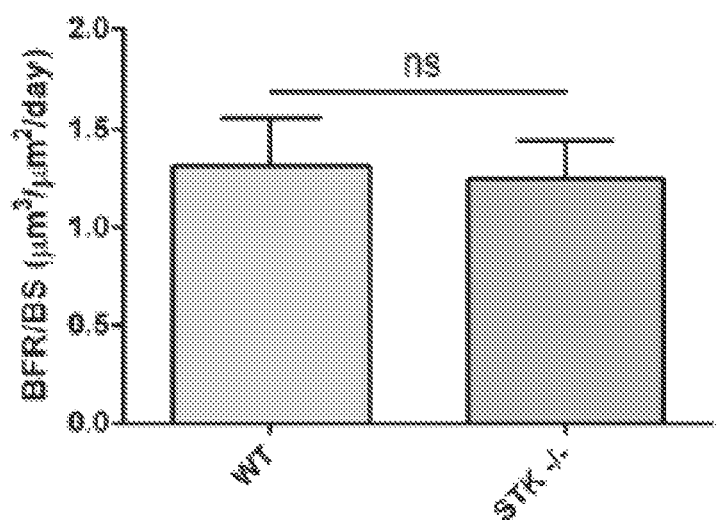
FIG. 8F is a bar chart showing bone formation rate per total bone surface in WT and STK−/− mice.
Figure 8G:
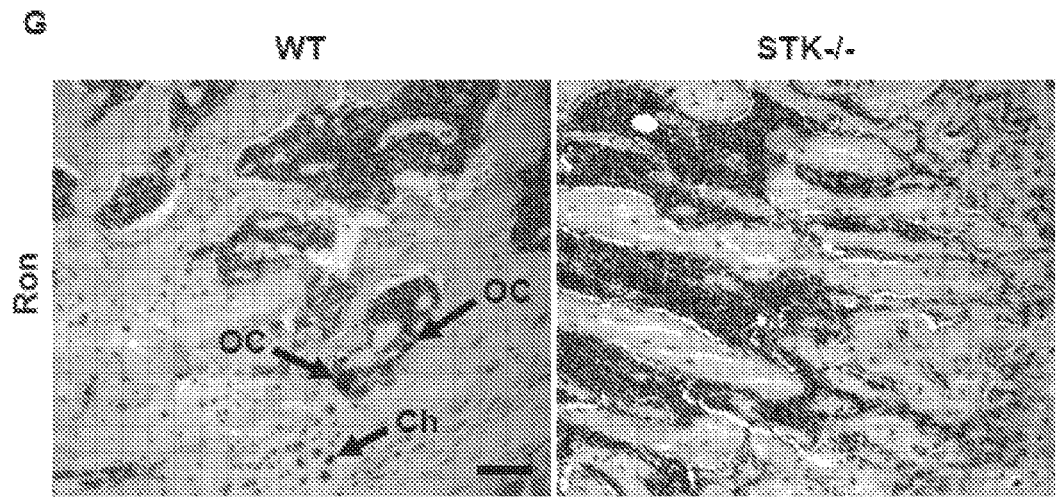
FIG. 8G is a pair of images of tissue sections stained for RON in normal, uninjected WT, and STK−/− mice.
Figure 8H:
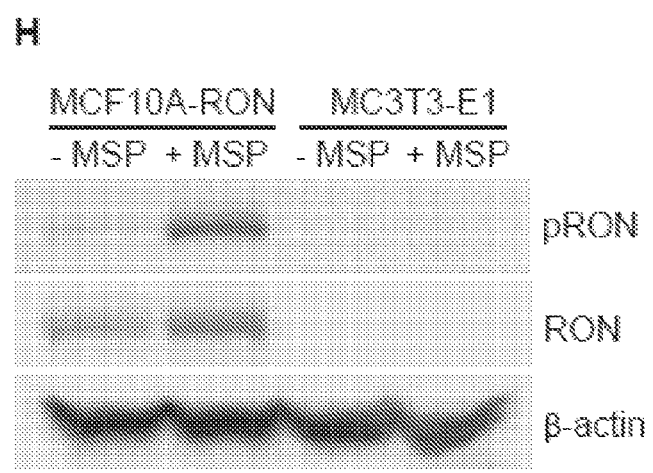
FIG. 8H is a Western analysis for RON and phospho-Ron in the MCF10A-Ron and MC3T3-E1 cell lines.

To determine if protection from osteolysis in the RonTK−/− mice was due to an increase in bone formation due to elevated osteoblast activity, WT and RonTK−/− bones were labeled in vivo and histomorphometric bone parameters were analyzed. There were no significant differences in the mineral apposition rate (MAR) or the bone formation rate (BFR), indicating that there was no inherent difference in osteoblast activity between WT and RonTK−/− mice (FIG. 8B-D). FIG. 8B shows bone formation as observed by calcein and Alizarin double labeling (scale bar=100 μm for images at 4× magnification and 50 μm for inset images at 40× magnification). FIG. 8C shows mineral apposition rate determined by bone histomorphometric analysis in WT and RonTK−/− mice (n=4-5; ns=not significant). FIG. 8D shows bone formation rate per total bone surface in WT and RonTK−/− mice (n=4-5; ns=not significant). To ensure that a tyrosine kinase-independent function of RON was not contributing to osteoblast activity, bones of mice completely lacking murine RON (STK) protein (Correll et al. *Genes Funct.* 1997, 1, 69-83) were also examined. Again, no differences in osteoblast activity were seen between WT and total RON knockout mice (STK−/−) (FIG. 8B and FIG. 8E-F). FIG. 8E shows mineral apposition rate in WT and STK−/− mice (n=4-5; ns=not significant). FIG. 8F shows bone formation rate per total bone surface in WT and STK−/− mice (n=4-5; ns=not significant). Consistent with this finding, staining bone sections with antibodies specific for RON showed expression in osteoclasts and chondrocytes, but not in osteoblasts (FIG. 8G), and no RON or phosphorylated RON expression was detected in the MC3T3-E1 osteoblast cell line (FIG. 8H). FIG. 8G shows tissue sections stained for RON in normal, uninjected WT, and STK−/− mice. FIG. 8H shows a western analysis for RON and phospho-RON in the MCF10A-RON and MC3T3-E1 cell lines. Cells were grown in the presence of 10% serum to 90% confluency. The media was then exchanged for media containing 0.5% serum and the cells were cultured overnight. 100 pg/mL MSP was added for 15 minutes and lysates were prepared. The MCF10A cell line overexpressing RON served as the positive control for RON and phospho-RON expression while the MC3T3-E1 cell line demonstrated the lack of RON expression in osteoblasts. Together, these data strongly suggest that the ability of MSP-expressing tumor cells to induce osteolysis was not due to changes in osteoclast numbers or osteoblast activity. The hypothesis that MSP-mediated osteolysis was due to RON-dependent effects on osteoclast activity was therefore pursued.

Example 3

Host RON Activity Drives Osteolysis from Metastatic Human Breast Cancer

Figure 2A:
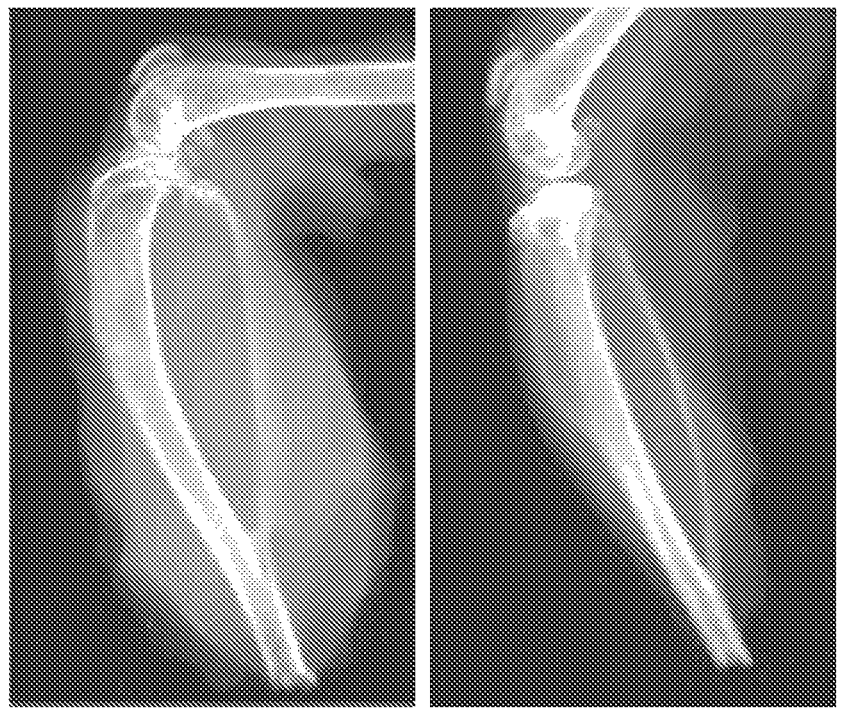
FIG. 2A is a pair of representative X-ray images of DU4475 bone lesions in NOD.SCID/WT or NOD.SCID/Ron TK−/− mice.
Figure 2B:
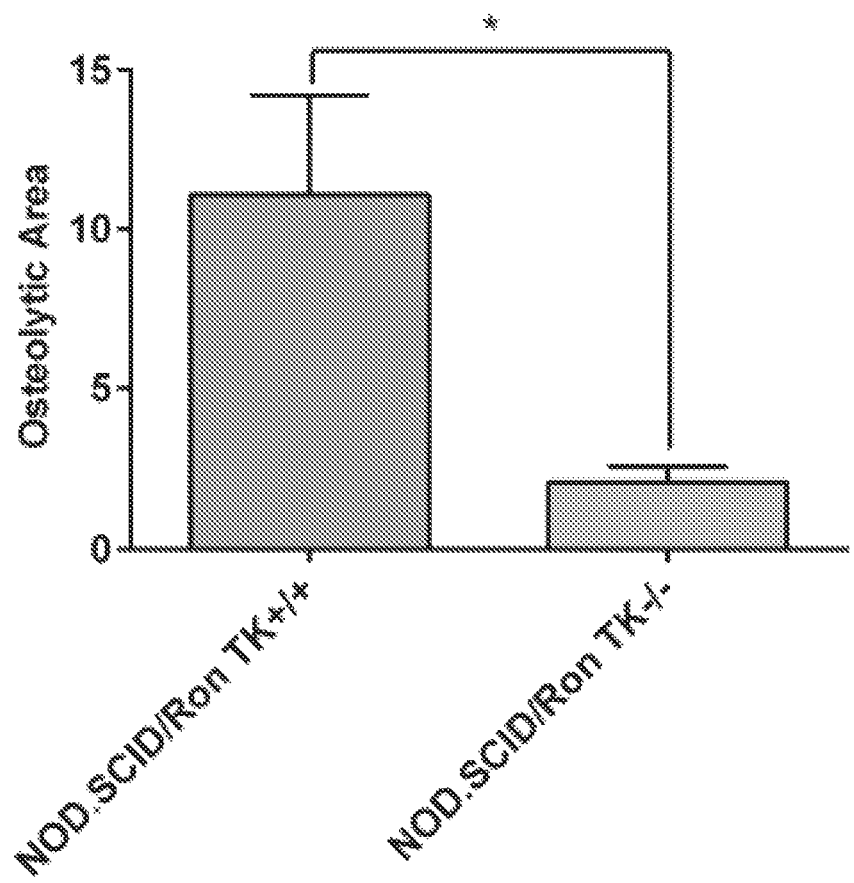
FIG. 2B is a bar chart showing osteolytic area from tibial bone lesions.
Figure 2C:
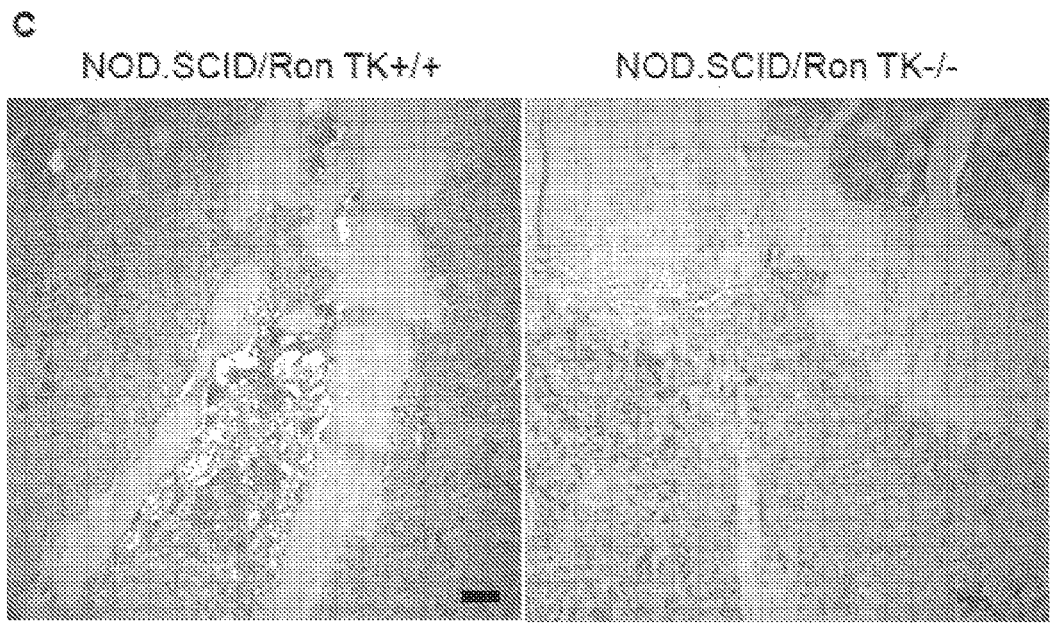
FIG. 2C is a pair of images of TRAP staining on sections of tumor-bearing bones from various experimental groups.
Figure 2D:
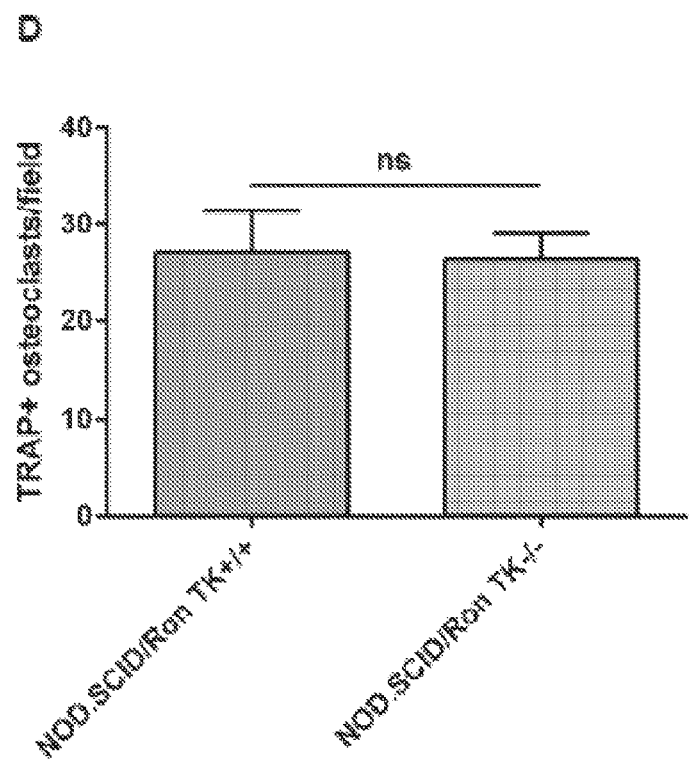
FIG. 2D is a bar chart showing the number of TRAP+ osteoclasts per field in various experimental groups.
Figure 2E:
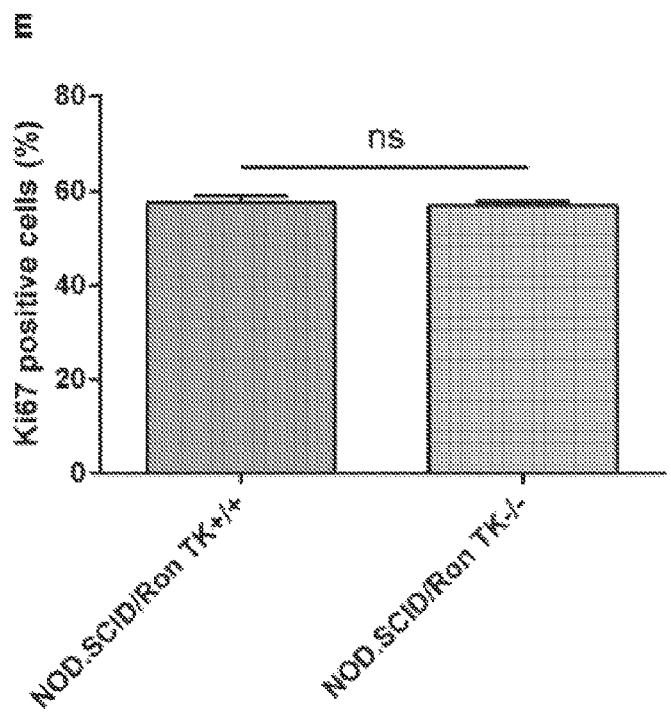
FIG. 2E is a bar chart showing the proliferation rate of DU4475 tumor cells in the bone, expressed as the percentage of Ki67 positive cells.
Figure 9A:
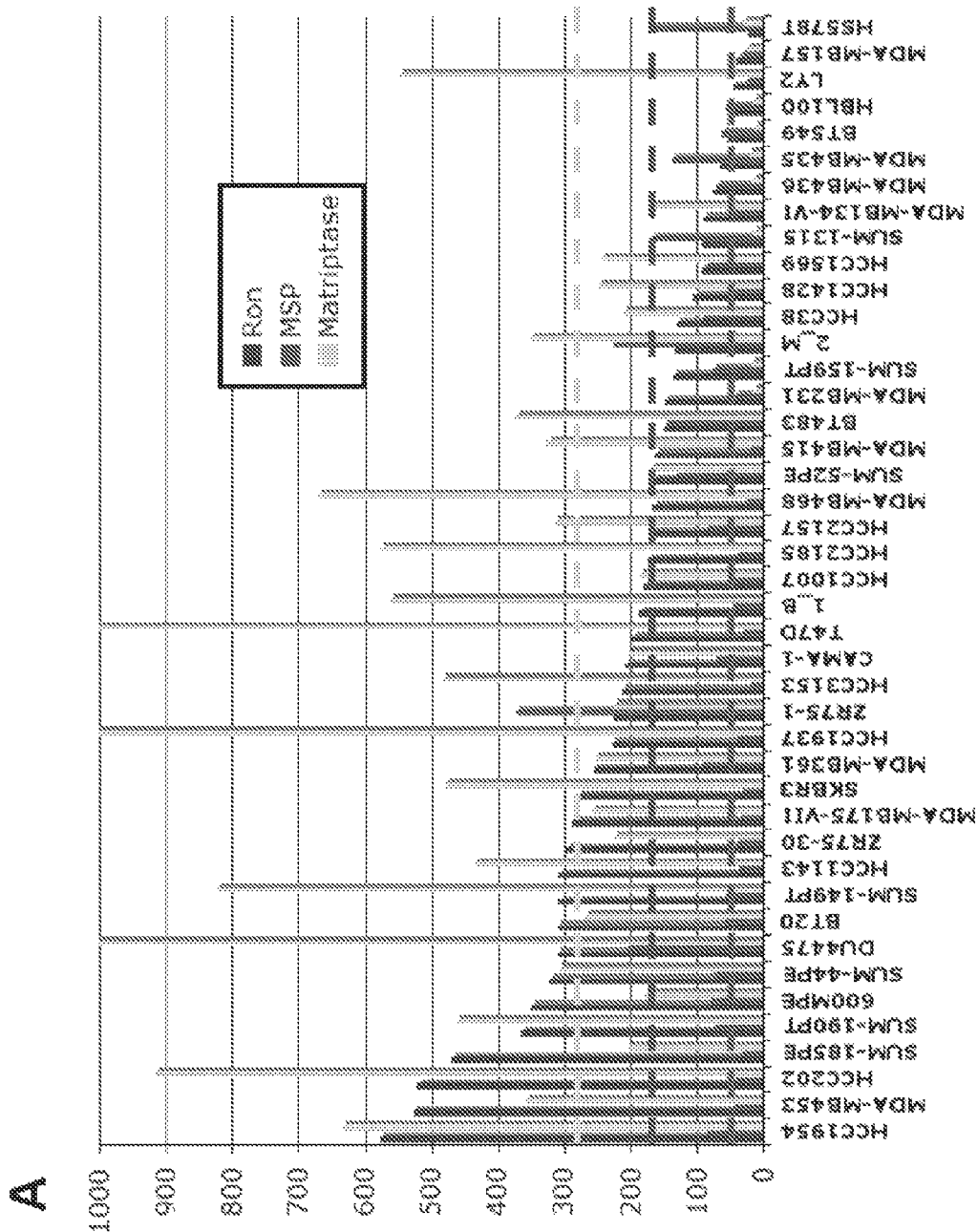
FIG. 9A is a bar chart showing mRNA expression levels of MSP, RON, and matriptase in a panel of human breast cancer cell lines.
Figure 9B:
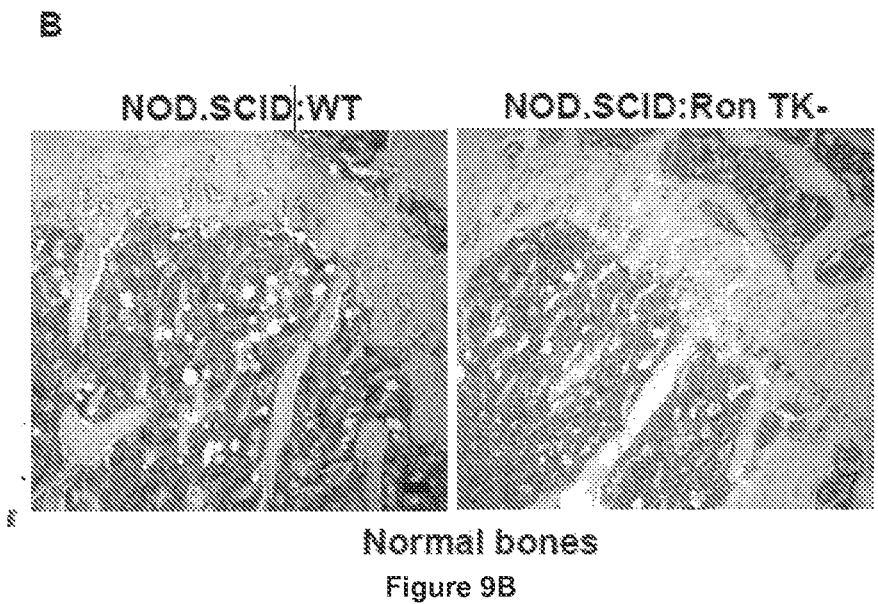
FIG. 9B is a pair of images of TRAP stained normal, uninjected NOD.SCID:WT, and NOD.SCID:Ron TK−/− bones.
Figure 9C:
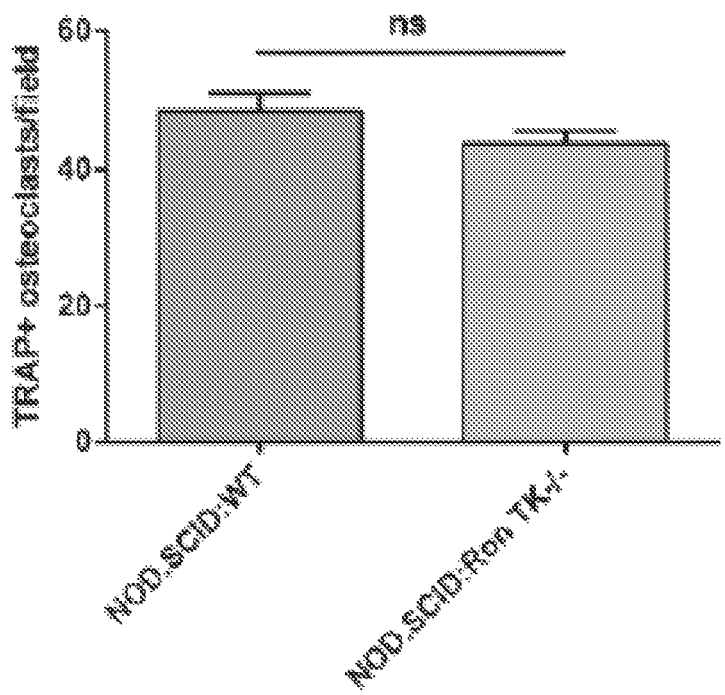
FIG. 9C is a bar chart showing TRAP+ osteoclasts from normal, uninjected bones.

To ensure that the findings were not restricted to the effects of mouse tumors or tumors engineered to overexpress MSP, the expression levels of MSP, RON, and matriptase in a panel of human breast cancer cell lines was examined and a cell line (DU4475) chosen that expressed each of these genes above an average expression level, similar to patient tumor samples (FIG. 9A). FIG. 9A shows mRNA expression levels of MSP, RON, and matriptase in a panel of human breast cancer cell lines, wherein dotted lines depict average expression level for each gene. The metastatic breast cancer cell line DU4475 was selected and injected into the tibias of WT or RonTK−/− mice (both crossed with NOD.SCID and then backcrossed into the FVB genetic background). While the DU4475 cell line was osteolytic in NOD.SCID mice carrying wild type alleles of RON (NOD.SCID/RonTK+/+), osteolysis was significantly reduced in the NOD.SCID/RonTK−/− mice (FIG. 2A and FIG. 2B). FIG. 2A shows representative X-ray images of DU4475 bone lesions in NOD.SCID/WT or NOD.SCID/Ron TK−/− mice, 42 days post tumor cell injection. FIG. 2B shows quantification of osteolytic area from tibial bone lesions (n=5; p<0.05). These results show that MSP/RON-dependent osteolysis was not restricted to the mouse overexpression model, but can be expanded to include human cell lines that naturally overexpress endogenous MSP. Again, there was no significant difference in the number of TRAP+ osteoclasts in NOD.SCID/RonTK+/+ versus NOD.SCID/RonTK−/− mice harboring DU4475 tumors (FIG. 2C and FIG. 2D) or in normal, non tumor-bearing NOD.SCID/RonTK+/+ and NOD.SCID/RonTK−/− mice (FIG. 9B and FIG. 9C). FIG. 2C shows TRAP staining on sections of tumor-bearing bones from each experimental group (scale bar, 100 μm), FIG. 2D shows quantification of TRAP+ osteoclasts in each experimental group (n=3-4; ns=not significant), FIG. 9B shows TRAP staining of normal, uninjected NOD.SCID:WT, and NOD.SCID:Ron TK−/− bones (scale bar, 100 μm), and FIG. 9C shows quantification of TRAP+ osteoclasts from normal, uninjected bones (n=4; ns=not significant). Again, the lack of osteolysis could not be explained by a decrease in tumor proliferation in the NOD.SCID/Ron TK−/− mice (FIG. 2E, which shows proliferation rate of DU4475 tumor cells in the bone; n=3-4; ns=not significant).

Example 4

T Cells are Dispensable for MSP-Induced Osteolysis

Figure 9D:
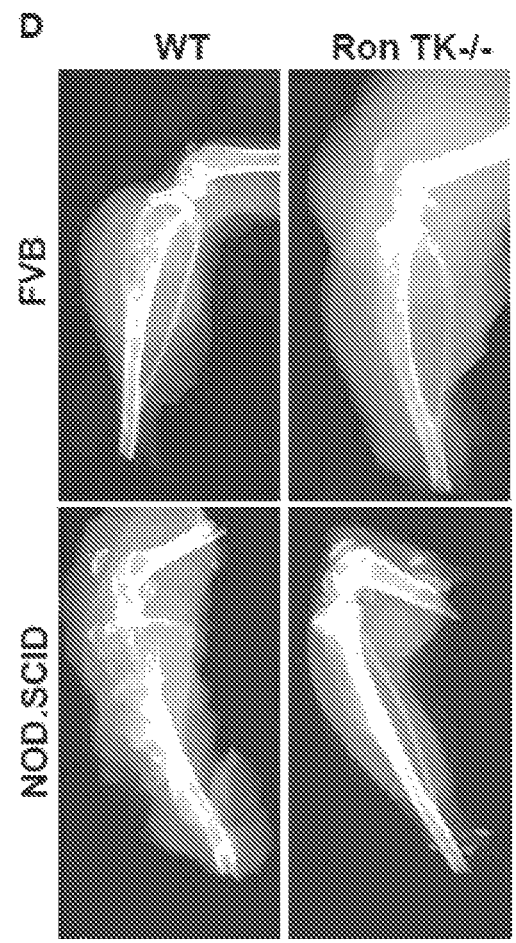
FIG. 9D is a series of X-ray images of bone lesions from various experimental groups.
Figure 9E:
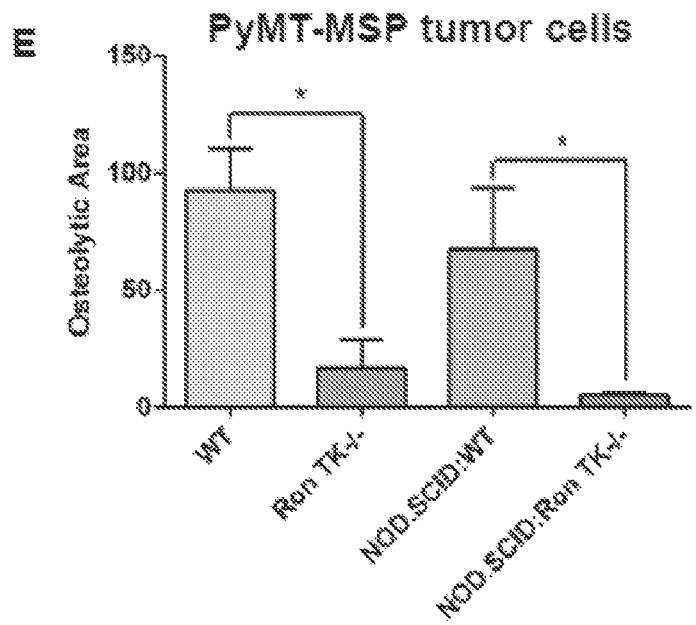
FIG. 9E is a bar chart showing the osteolytic area of bone lesions in mice from various experimental groups.
Figure 9F:
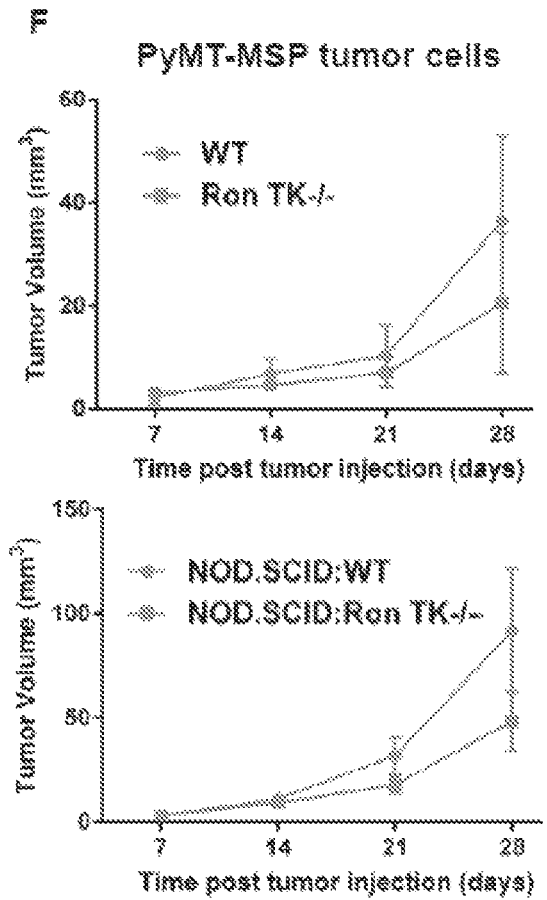
FIG. 9F is a pair of graphs showing growth curves of PyMT-MSP bone lesions from various experimental groups.
Figure 9G:
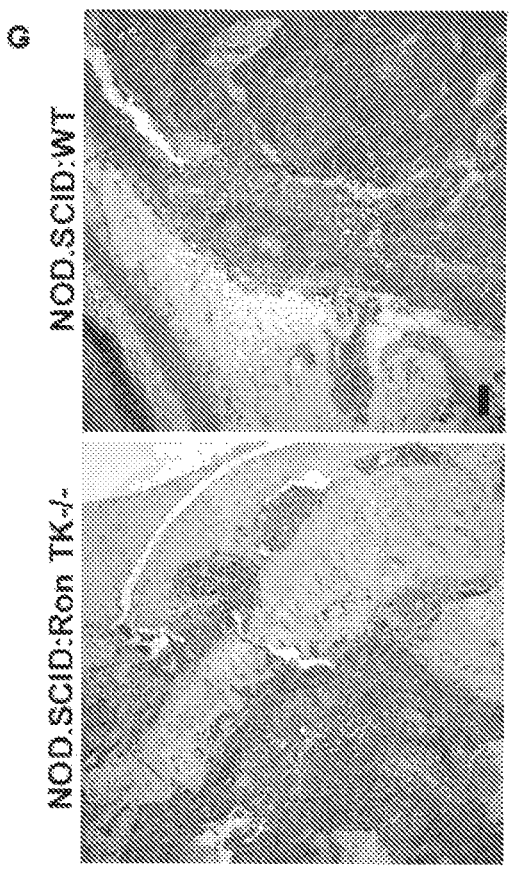
FIG. 9G is a pair of images of TRAP stained bone tumors from various experimental groups.
Figure 9H:
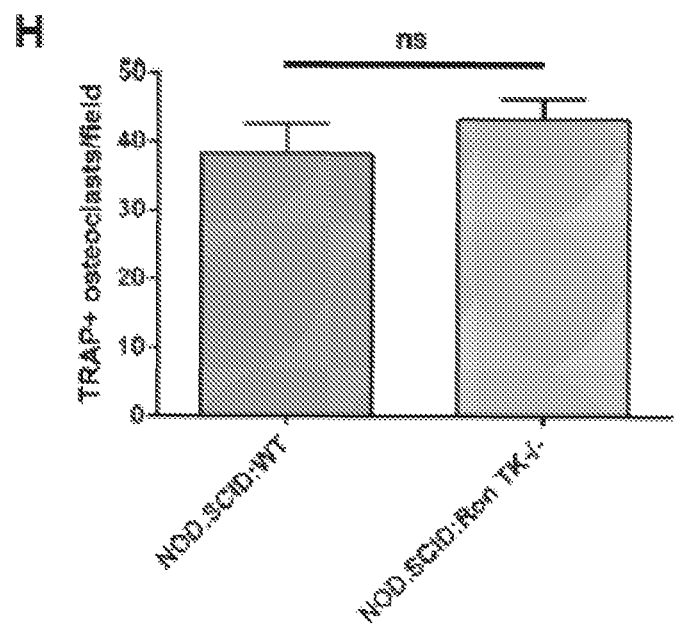
FIG. 9H is a bar chart showing TRAP+ osteoclasts from PyMT-MSP bone tumors of various experimental groups.

Because the above xenograft experiments had to be performed in immune-compromised mice, and because T cells have previously been shown to influence osteoclast activity, it was destired to ensure that the lack of tumor-induced osteolysis from human DU4475 cells in NOD.SCID/RonTK−/− mice was not due to a combination effect of RON TK deletion and the compromised immune system. To test whether T cells were required for MSP/RON-dependent osteolysis, the effects of injecting PyMT-MSP tumor cells into the tibias of syngenic immune-competent (FVB/RonTK+/+ or FVB/RonTK−/−), or immune-compromised (NOD.SCID/RonTK+/+ or NOD.SCID/RonTK−/−) mice were compared. MSP-mediated osteolysis was not significantly altered in the immune-compromised mice and still demonstrated the necessity for RON activity in the host (FIG. 9D and FIG. 9E). FIG. 9D shows X-ray images of bone lesions from each group. Mice were sacrificed 28 days post tumor cell injection for analysis. FIG. 9E shows quantification of osteolytic area of bone lesions in mice from each experimental group (n=3-5; p=0.04 and p=0.05 respectively). There was also no significant difference in tumor growth or in the number of TRAP+ osteoclasts in these experiments (FIG. 9F-H). FIG. 9F shows growth curves of PyMT-MSP bone lesions for each experimental group. Tumor size was determined by caliper measurements. FIG. 9G shows TRAP staining of bone tumors from each experimental group (scale bar, 100 μm). FIG. 9H shows quantification of TRAP+ osteoclasts from PyMT-MSP bone tumors of each experimental group (n=4). While not statistically significant, there was a trend toward increased growth in the immune-deficient background, but no difference in osteolysis. These data showed that the mechanism for MSP-driven bone destruction does not require T-cell activity, or any other component of the adaptive immune system.

Example 5

Treatment with RON Inhibitors Blocks Osteolysis

Figures 3A, 3B:
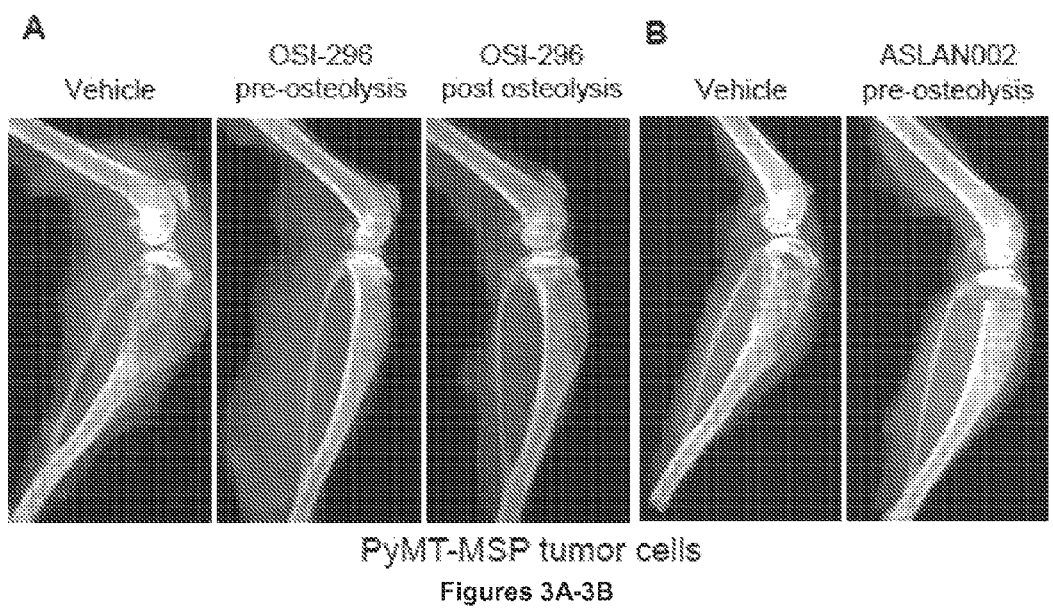
FIG. 3A is a series of X-ray images of PyMT-MSP bone lesions from mice treated with OSI-296.
FIG. 3B is a pair of X-ray images of PyMT-MSP bone lesions from mice treated with ASLAN002.
Figure 3C:
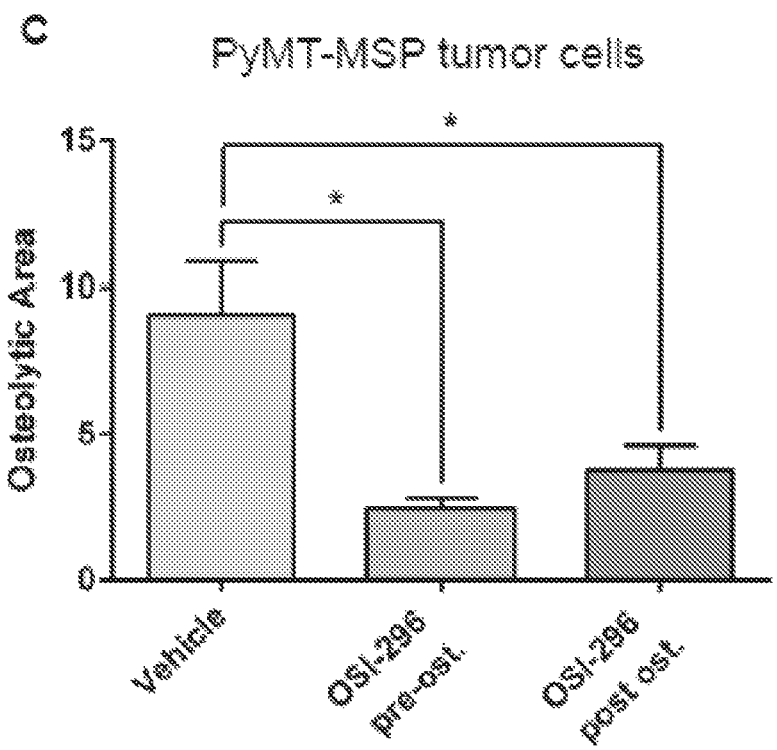
FIG. 3C is a bar chart showing osteolytic area in PyMT-MSP bone lesions from mice treated with OSI-296.
Figure 3D:
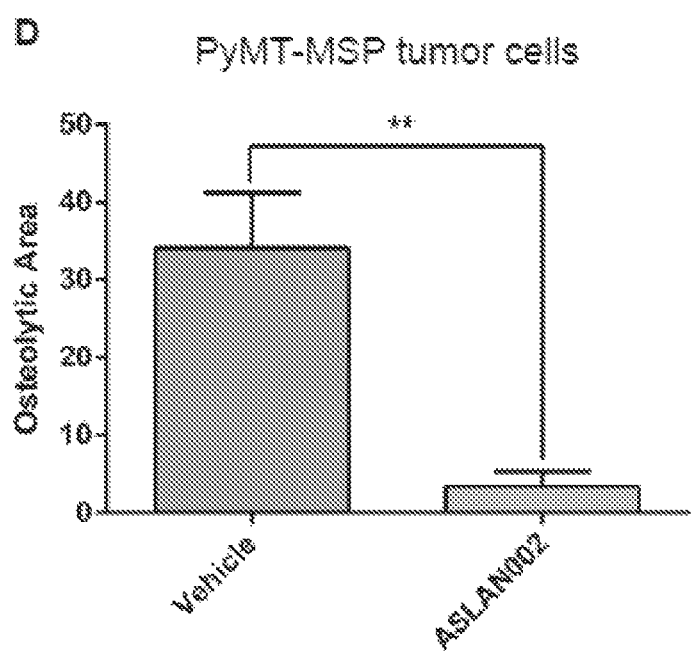
FIG. 3D is a bar chart showing the osteolytic area in PyMT-MSP bone lesions from mice treated with ASLAN002.
Figure 3E:
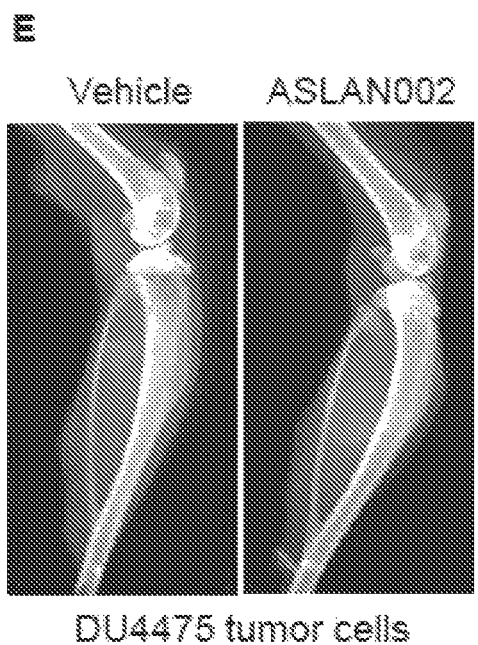
FIG. 3E is a pair of representative X-ray images of DU4475-induced bone lesions from mice treated with ASLAN002.
Figure 3F:
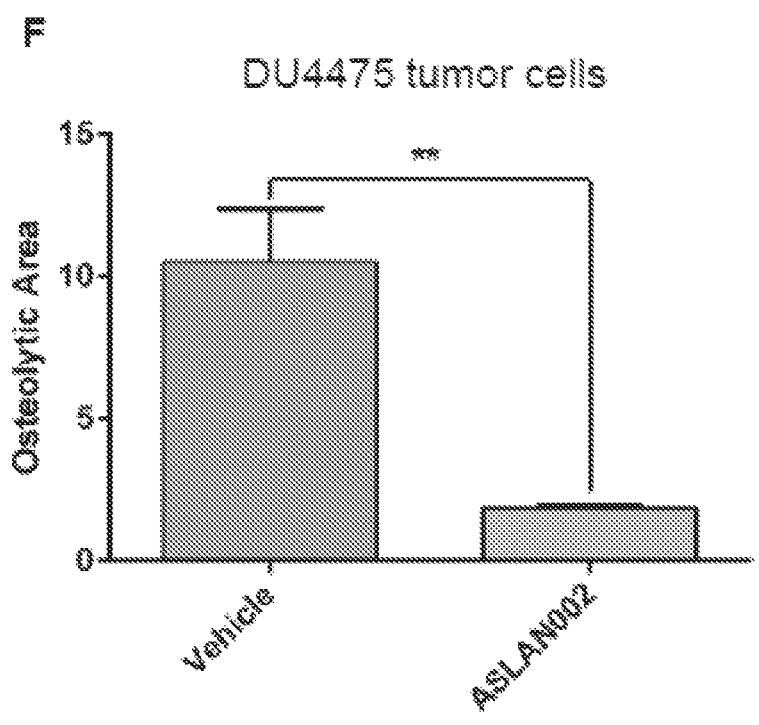
FIG. 3F is a bar chart showing the osteolytic area in DU4475 bone lesions from mice in various experimental groups.
Figure 3G:
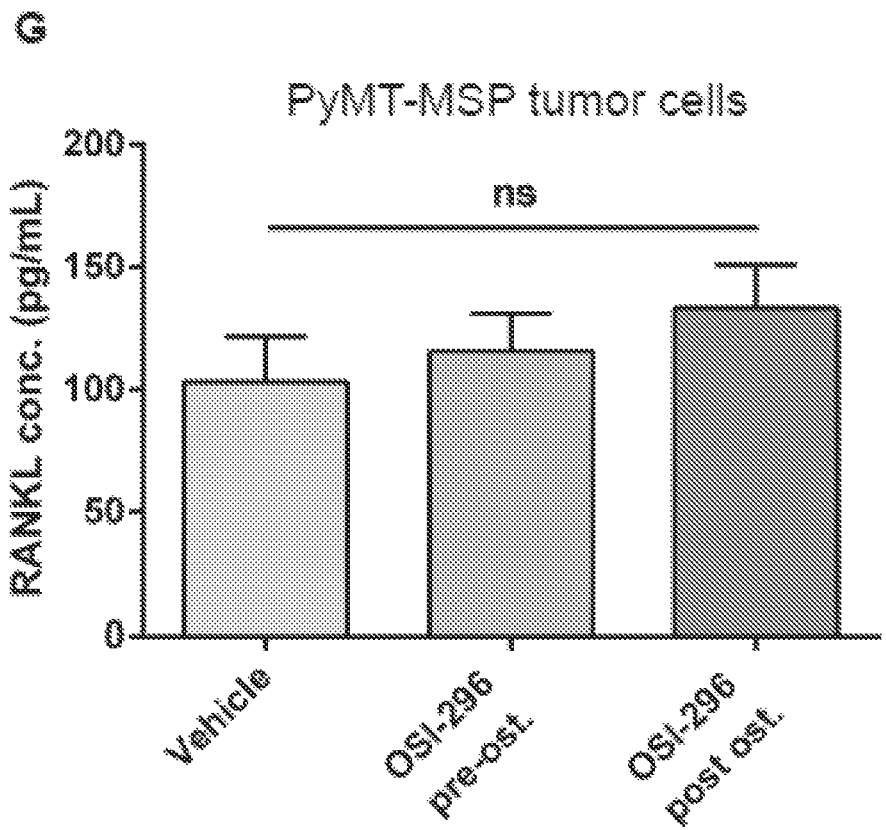
FIG. 3G is a bar chart showing serum RANKL concentration from mice in various experimental groups.
Figure 10A:
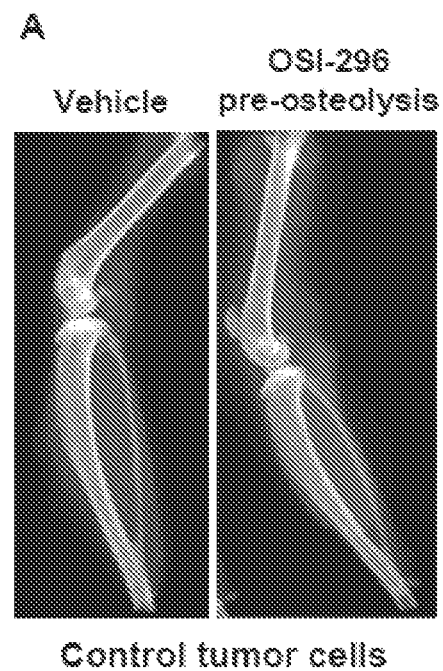
FIG. 10A is a pair of X-ray images of PyMT control bone lesions treated with OSI-296.
Figure 10B:
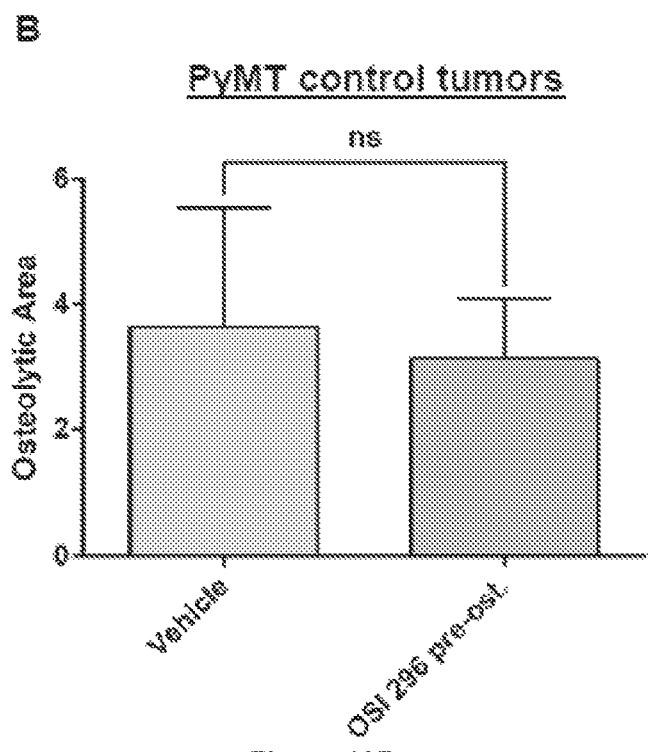
FIG. 10B is a bar chart showing the osteolytic area in mice with bone lesions treated with OSI 296.
Figure 10C:
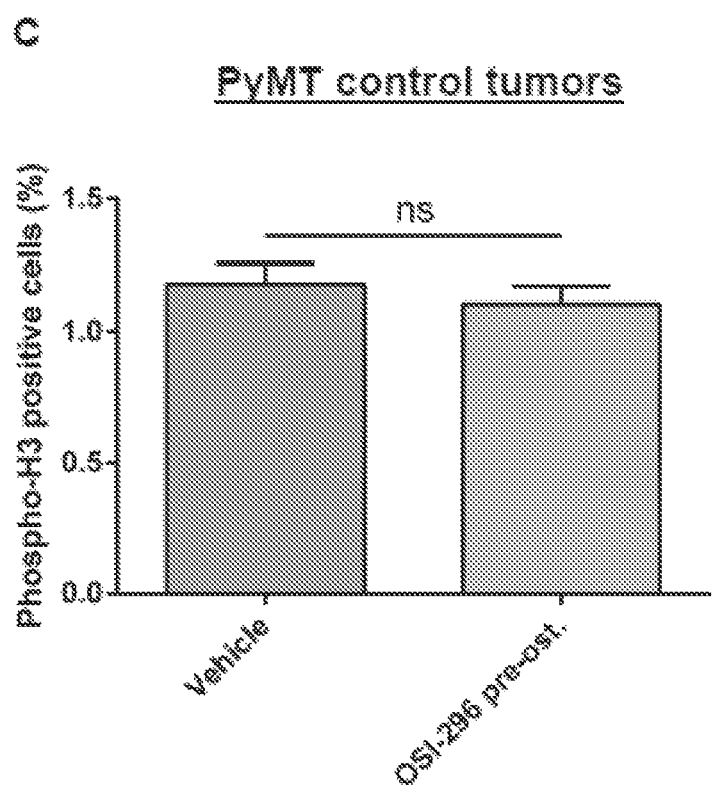
FIG. 10C is a bar chart showing the proliferation rate for PyMT control tumors indicated as percent cells staining positive for phospho-H3.
Figure 10D:
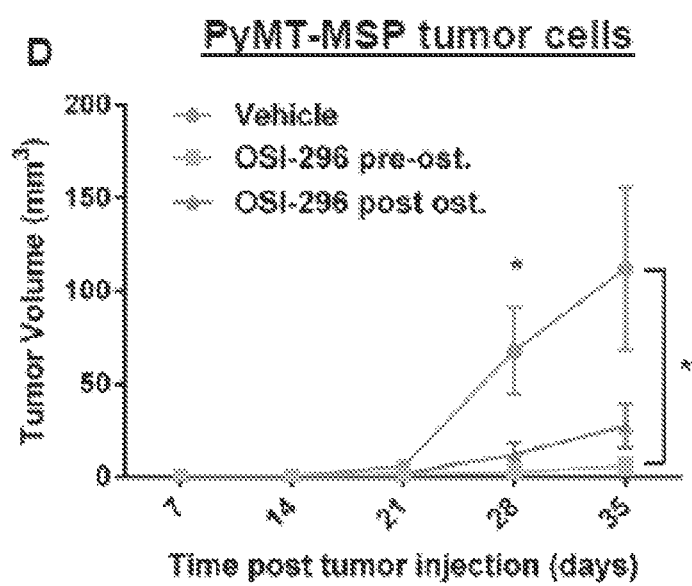
FIG. 10D is a graph showing the tumor growth curve for PyMT-MSP bone lesions treated with OSI-296.
Figure 10E:
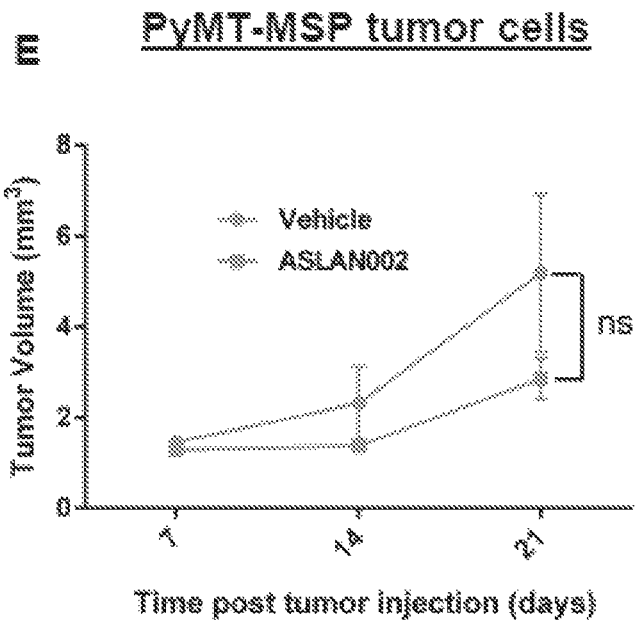
FIG. 10E is a graph showing the tumor growth curve for PyMT-MSP bone lesions treated with ASLAN002.
Figure 10F:
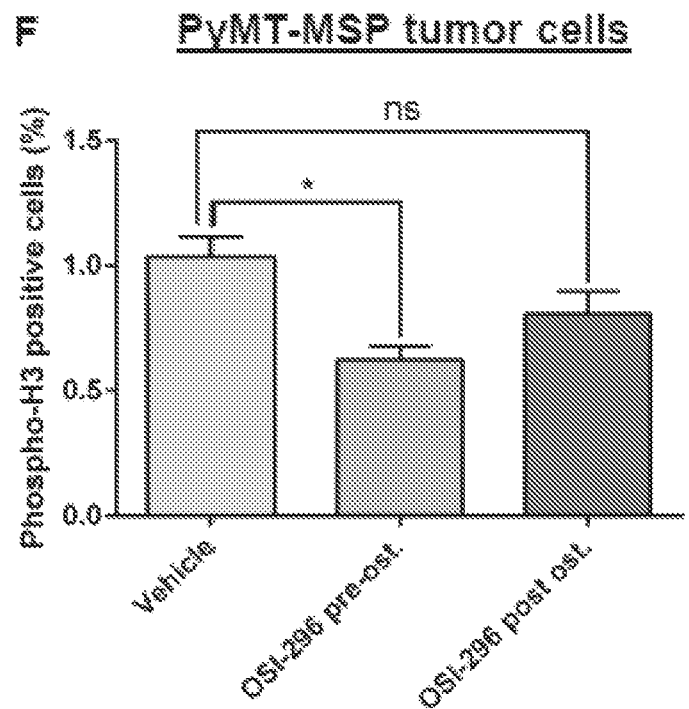
FIG. 10F is a bar chart showing the proliferation rate of PyMT-MSP tumors treated with OSI-296.
Figure 10G:
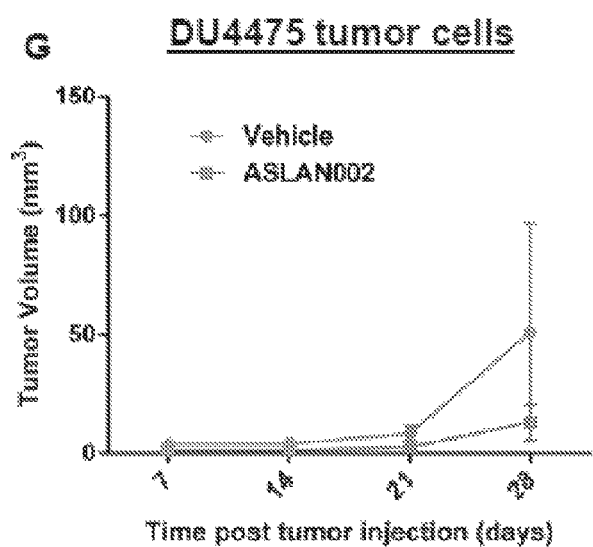
FIG. 10G is a graph showing the tumor growth curve for DU4475 bone lesions from experimental groups treated with ASLAN002.
Figure 11A:
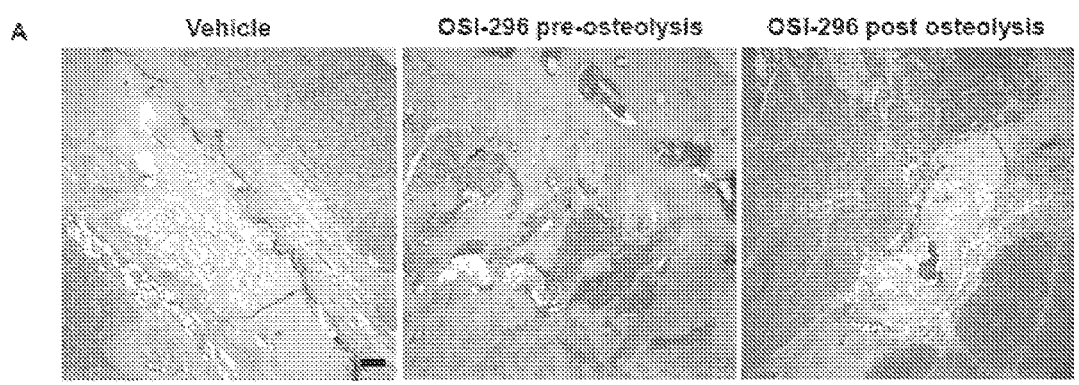
FIG. 11A is a series of images of TRAP stained PyMT-MSP bone tumors from mice treated with OSI-296 either 3 days post tumor cell injection for pre-osteolysis or 3 weeks post injection for post osteolysis treatment.
Figure 11B:
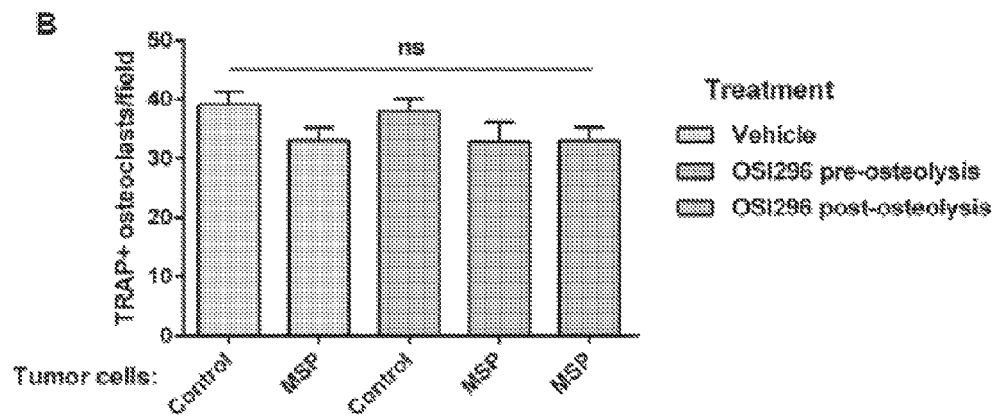
FIG. 11B is a bar chart showing TRAP+ osteoclasts from bone tumors in various experimental groups.
Figure 11C:
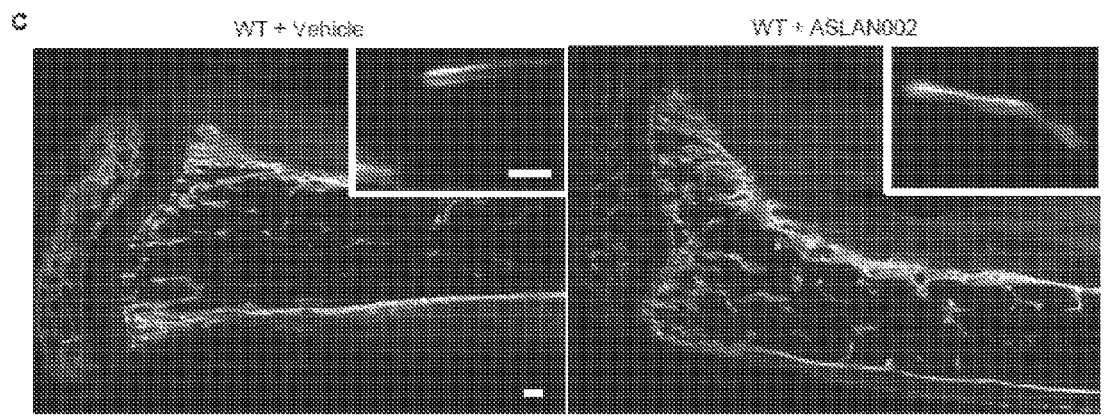
FIG. 11C is a pair of images showing bone formation as observed by calcein and Alizarin double labeling.
Figure 11D:
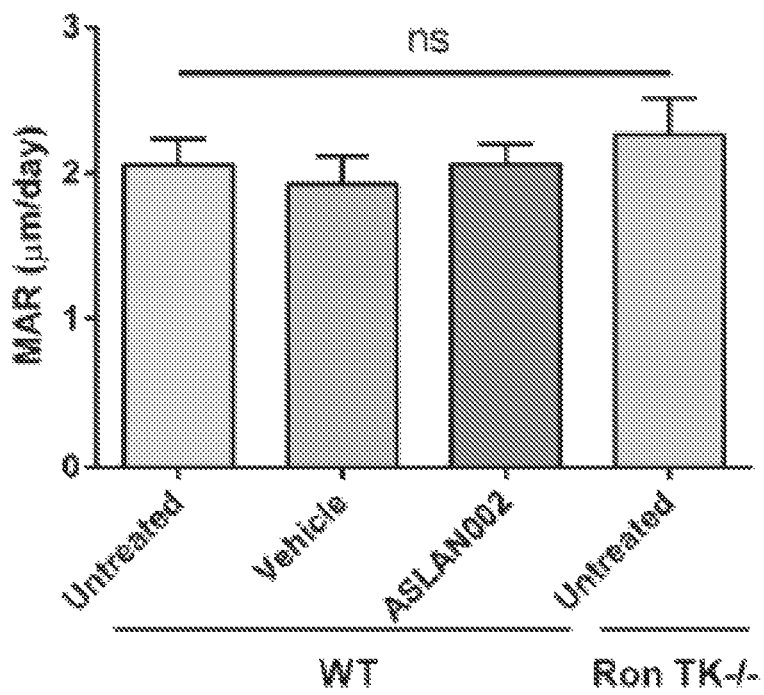
FIG. 11D is a bar chart showing mineral apposition rate in normal, uninjected animals treated with ASLAN002.
Figure 11E:
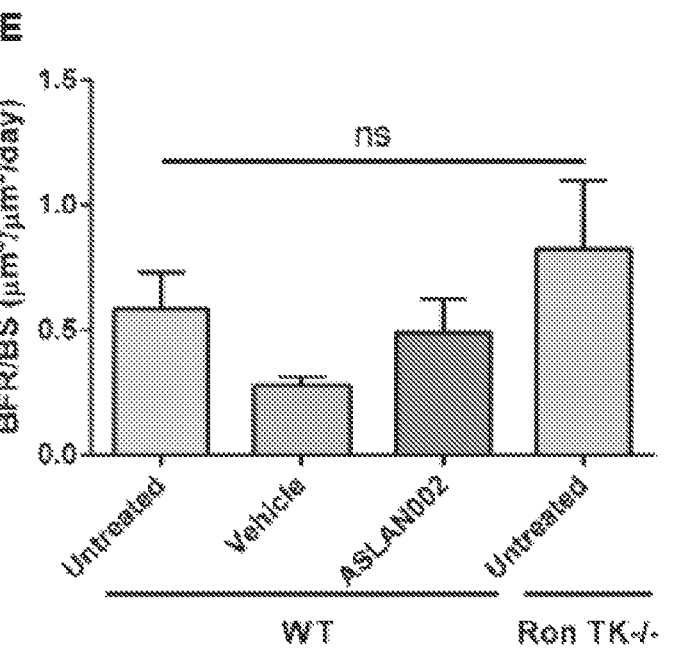
FIG. 11E is a bar chart showing bone formation rate per total bone surface in animals treated with ASLAN002.

Based on the data obtained using RonTK−/− mice, it was tested whether pharmacological inhibition of RON could provide protection from osteolysis. Tibias were injected with MSP-expressing PyMT tumor cells or DU4475 breast cancer cells and treated them with two different small molecule tyrosine kinase inhibitors that are selective for RON and Met (OSI-296 and ASLAN002). OSI-296 is more selective for Met ($IC_{50}$ of 42 nM for Met and 200 nM for RON; Steinig et al. *Bioorg. Med. Chem.* 2013, 23, 4381-4387), while ASLAN002 (also known as BMS-777607) is more selective for RON ($IC_{50}$ of 3.9 nM for Met and 1.8 nM for RON; Schroeder et al. *J. Med. Chem.* 2009, 52, 1251-1254). When animals were treated with either drug, beginning three days after tumor injection, osteolysis from PyMT-MSP tumors was significantly inhibited, phenocopying the results obtained with RonTK−/− mice. OSI-296 caused an average 4-6 fold inhibition of osteolysis, and ASLAN002 caused 6-10 fold inhibition of osteolysis (FIG. 3A-D). FIG. 3A shows X-ray images of PyMT-MSP bone lesions from mice treated with OSI-296. Treatment began 3 days post tumor cell injection for pre-osteolysis treatment and 3 weeks post injection for post osteolysis treatment. Mice were sacrificed 42 days post injection for analysis. FIG. 3B shows X-ray images of PyMT-MSP bone lesions from mice treated with ASLAN002. Treatment began 3 days post tumor cell injection. Mice were sacrificed 21 days post injection for analysis. FIG. 3C shows quantification of osteolytic area in PyMT-MSP bone lesions from mice treated with OSI-296 (n=7-10 per group; p=0.01). FIG. 3D shows quantification of osteolytic area in PyMT-MSP bone lesions from mice treated with ASLAN002 (n=4-5 per group; p=0.0074). ASLAN002, but not OSI-296, also prevented osteolysis from DU4475 cells (FIG. 3E and FIG. 3F). FIG. 3E shows representative X-ray images of DU4475-induced bone lesions from mice treated with ASLAN002. Treatment began 3 days post tumor cell injection, and mice were sacrificed 28 days post injection for analysis. FIG. 3F shows quantification of osteolytic area in DU4475 bone lesions from mice in each experimental group (n=5; p=0.0016). RON inhibition did not have an effect on the ability of tumors that do not express MSP to cause osteolysis, again implicating an osteolytic pathway that is independent of MSP/RON signaling (FIG. 10A and FIG. 10B). FIG. 10A shows X-ray images of PyMT control bone lesions treated with OSI-296. FIG. 10B shows quantification of osteolytic area in mice with bone lesions treated with OSI-296 (n=8.5). Control tumor cells were injected into the tibia of WT mice, and treatment began 3 days post tumor cell injection. Mice were sacrificed 42 days post injection for analysis (ns=not significant). To determine the potential of RON inhibitors in a more clinically relevant setting, the animals were allowed to develop osteolysis that was visible by X-ray in live animals, and then began treatment (this was, on average, three weeks after tumor injection). While the osteolysis in vehicle treated mice continued to progress, RON inhibition was able to prevent further tumor-induced bone loss. These results carry clinical relevance, as they suggest that RON inhibitors could be useful in the post-metastatic, post-osteolytic setting (FIG. 3A and FIG. 3C). Treatment with OSI-296 also reduced PyMT-MSP tumor growth and proliferation rate in the bone, while treatment with ASLAN002 showed a trend in decreased growth, but did not reach statistical significance (FIG. 10D-F). FIG. 10C shows the proliferation rate for PyMT control tumors indicated as percent cells staining positive for phospho-H3 (n=3). FIG. 10D shows tumor growth curve and proliferation rate for PyMT-MSP bone lesions treated with OSI-296 (n=5.4). PyMT-MSP tumor cells were injected into the tibia of WT mice, and treatment began 3 days post tumor cell injection for pre-osteolysis treatment and 3 weeks post injection for post osteolysis treatment. Mice were sacrificed 42 days post injection for analysis. FIG. 10E shows tumor growth curve and proliferation rate for PyMT-MSP bone lesions treated with ASLAN002 (n=5.4). PyMT-MSP tumor cells were injected into the tibia of WT mice and treatment began 3 days post tumor cell injection. Mice were sacrificed 21 days post tumor cell injection; tumor size was determined by caliper measurements. FIG. 10F shows proliferation rate of PyMT-MSP tumors treated with OSI-296 (n=3). Neither drug significantly inhibited growth of DU4475 tumors (FIG. 10G, showing tumor growth curve and proliferation rate for DU4475 bone lesions from each experimental group treated with ASLAN002 (n=5); DU4475 tumor cells were injected into the tibia of NOD.SCID/Ron TK+/+; treatment began 3 days post tumor cell injection, and mice were sacrificed 42 days post tumor cell injection for analysis). Again, RON inhibition had no significant effect on the number of TRAP+ osteoclasts present (FIG. 11A and FIG. 11B). FIG. 11A shows TRAP staining of PyMT-MSP bone tumors from mice treated with OSI-296 either 3 days post tumor cell injection for pre-osteolysis or 3 weeks post injection for post osteolysis treatment. Mice were sacrificed 42 days post injection for analysis. FIG. 11B shows quantification of TRAP+ osteoclasts from bone tumors in each experimental group (n=4; ns=not significant). RON inhibitors also did not affect RANKL production as measured by serum ELISA, suggesting that the lack of bone destruction was not due to indirect inhibition of RANKL signaling (FIG. 3G, showing ELISA-based quantification of serum RANKL concentration from mice in each experimental group; n=3; ns=not significant). RON inhibitors also did not affect bone formation in vivo, supporting a model in which blockade of RON signaling leads to a specific reduction in osteoclast activity, not an increase in osteoblast activity (FIG. 11C-E). FIG. 11C shows bone formation as observed by calcein and Alizarin double labeling (scale bar=100 μm for images at 4× magnification and 50 μm for inset images at 40× magnification). FIG. 11D shows mineral apposition rate in normal, uninjected animals treated with ASLAN002 (ns=not significant). FIG. 11E shows bone formation rate per total bone surface in animals treated with ASLAN002 (ns=not significant).

Example 6

Figure 4A:
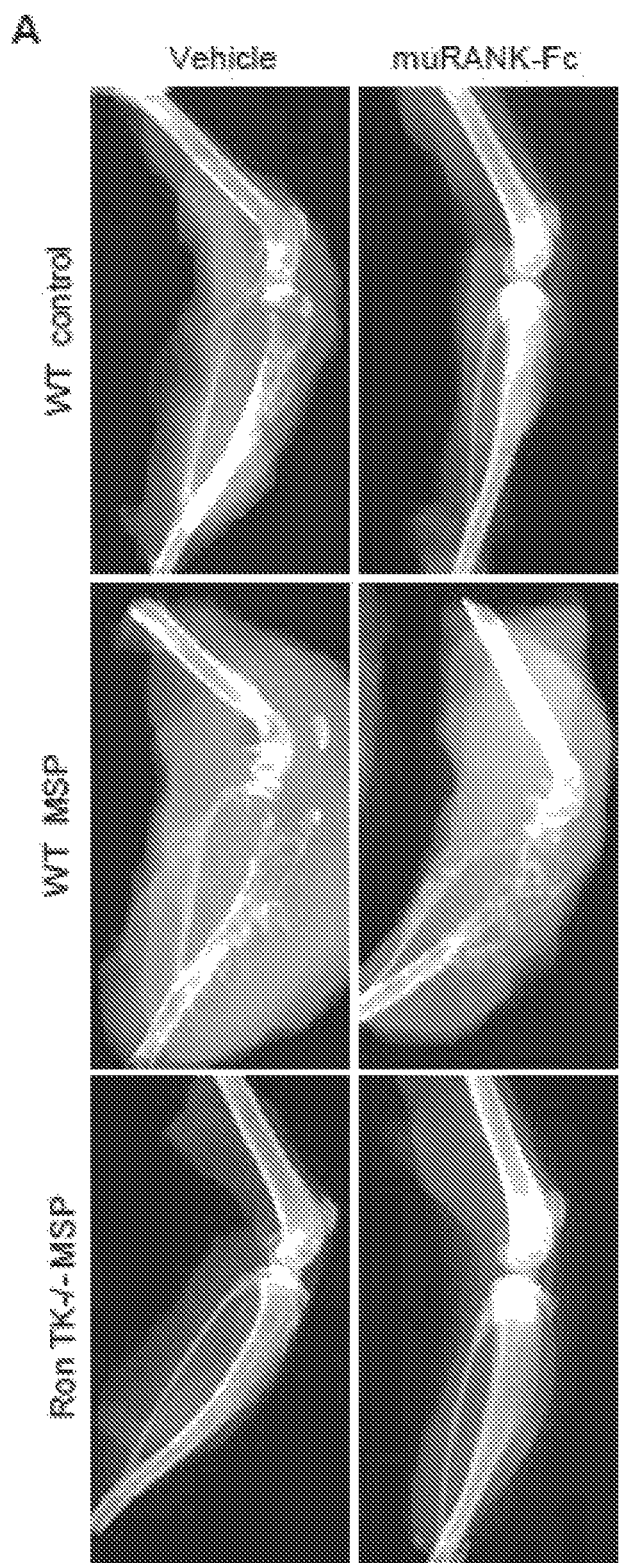
FIG. 4A is a series of representative X-ray images of PyMT-MSP bone lesions from mice treated with muRANK-Fc.
Figure 4B:
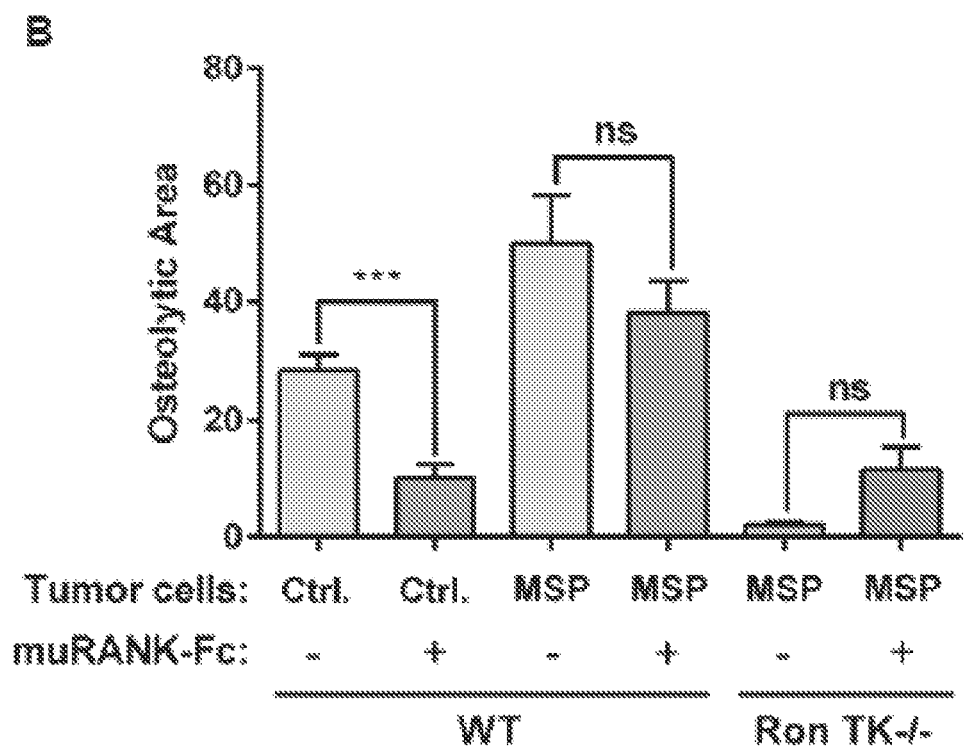
FIG. 4B is a bar chart of the osteolytic area in bone lesions from mice in each experimental group.
Figure 4C:
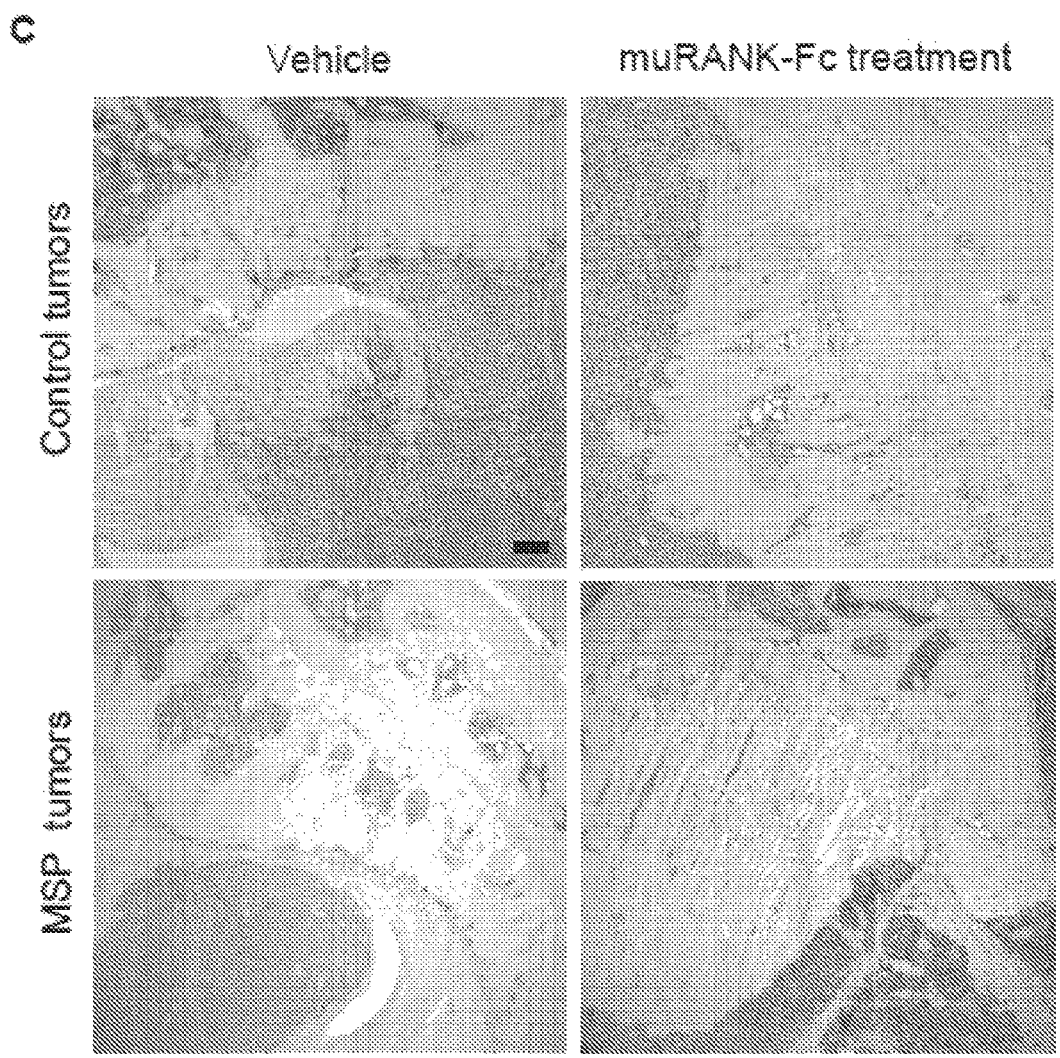
FIG. 4C is a series of images of TRAP stained tumor-bearing bones from various experimental groups.
Figure 12A:
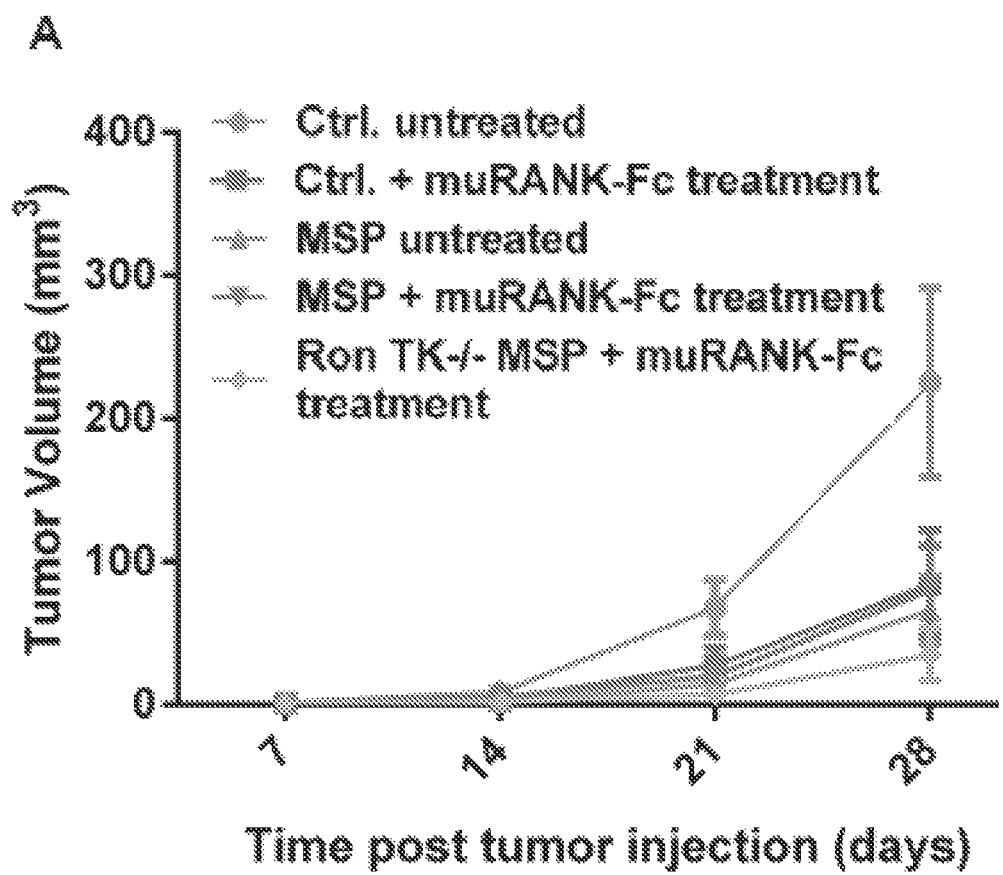
FIG. 12A is a graph showing the growth curve from bone lesions treated with muRANK-Fc in each experimental group.
Figure 12B:
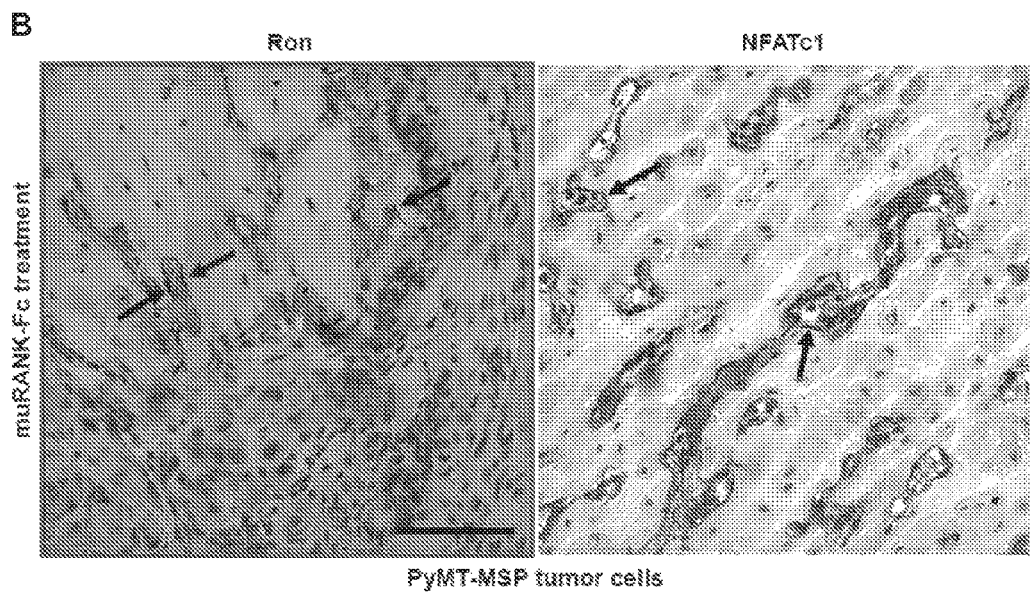
FIG. 12B is a pair of images of RON and NFATc1 stained tissue sections from PyMT-MSP tumor bearing bones treated with muRANK-Fc.
Figure 12C:
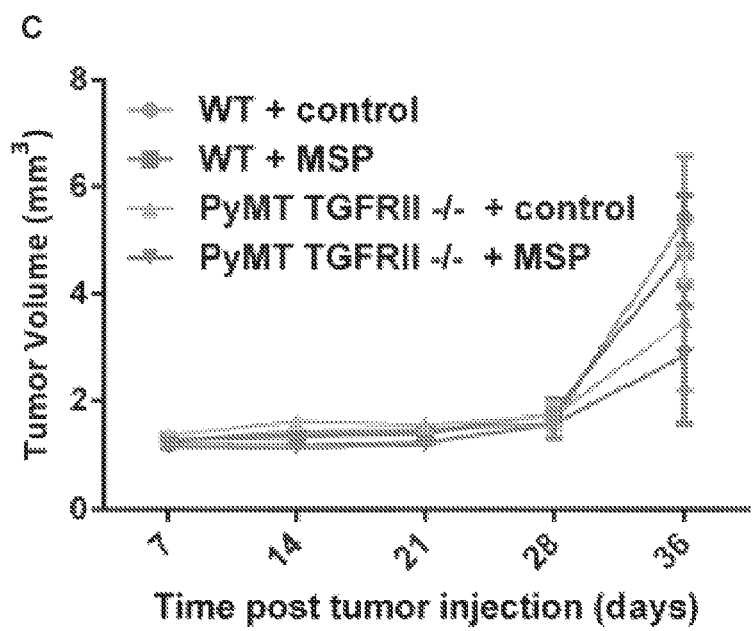
FIG. 12C is a graph showing a growth curve from bone lesions in mice from each experimental group.

MSP/RON Signaling is a Novel Mechanism of Osteolysis that is not Dependent on RANKL or TGFβ Signaling Both RANKL and TGFβ have been shown to play major roles in osteoclast activation and the "vicious cycle." Denosumab, a RANKL antagonist, was recently FDA-approved to treat bone metastases and osteoporosis based on demonstration of increased time to development of skeletal-related events, such as fracture, in patients. Mechanistically, we wanted to determine if MSP/RON functionally interacts with RANKL and/or TGF pathways. To test whether MSP-driven osteolysis is dependent on activation of RANK by RANKL, mice were treated with the murine RANKL antagonist, muRANK-Fc, three days after intratibial injection of tumor cells. Destruction of bone in PyMT control tumors was significantly impaired upon treatment with the RANKL antagonist (FIG. 4A and FIG. 4B), despite no significant effect on tumor growth (FIG. 12A). FIG. 4A shows representative X-ray images of PyMT-MSP bone lesions from mice treated with muRANK-Fc; treatment began 3 days post tumor cell injection; mice were sacrificed 42 days post tumor cell injection for analysis. FIG. 4B shows quantification of osteolytic area in bone lesions from mice in each experimental group (n=16 per group for WT mice and 3-5 per group for Ron TK−/− mice respectively; p<0.0001; ns=not significant). FIG. 12A shows growth curve from bone lesions treated with muRANK-Fc in each experimental group, tumor cells were injected into the tibia of WT or Ron TK−/− mice, treatment began 3 days post tumor cell injection, and tumor size was determined by caliper measurements. These data supported the observation that the low level of RON-independent osteolysis present in control tumors is dependent upon the RANKL pathway and, importantly, that the antagonist is functional in the assays. However, PyMT tumor cells overexpressing MSP were able to cause significant osteolysis even in the presence of the RANKL antagonist. In addition, although the levels of MSP-driven osteolysis in the Ron TK−/− mice were already very low, inhibition of RANKL did not reduce this further (FIG. 4A and FIG. 4B). Staining of sections from these samples demonstrated successful RANKL inhibition by the lack of TRAP+ cells in these groups, as expected because TRAP expression is regulated downstream of RANK (FIG. 4C, showing TRAP staining of tumor-bearing bones from each experimental group; scale bar, 100 μm). FIG. 12B shows RON and NFATc1 staining of tissue sections from PyMT-MSP tumor bearing bones treated with muRANK-Fc, wherein arrows indicate positively stained osteoclasts (scale bar=50 μm). However, osteoclasts were still present following RANKL inhibition, as demonstrated by NFATc1 and RON immuno-staining (FIG. 12C, showing growth curve from bone lesions in mice from each experimental group, wherein tumor cells were injected into the tibia of WT mice, and tumor size was determined by caliper measurements). These data suggest that although the RANKL antagonist was effective in the assays, the ability of MSP to induce osteolysis does not require active RANKL signaling.

Figure 4D:
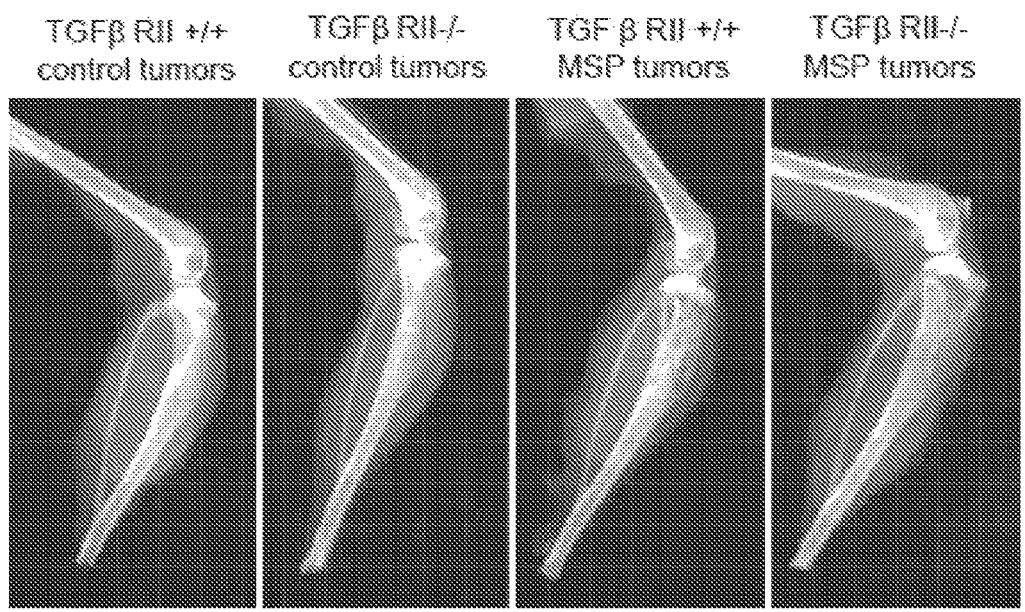
FIG. 4D is a series of X-ray images of PyMT bone lesions arising from tumors in the presence or absence of TGβRII.
Figure 4E:
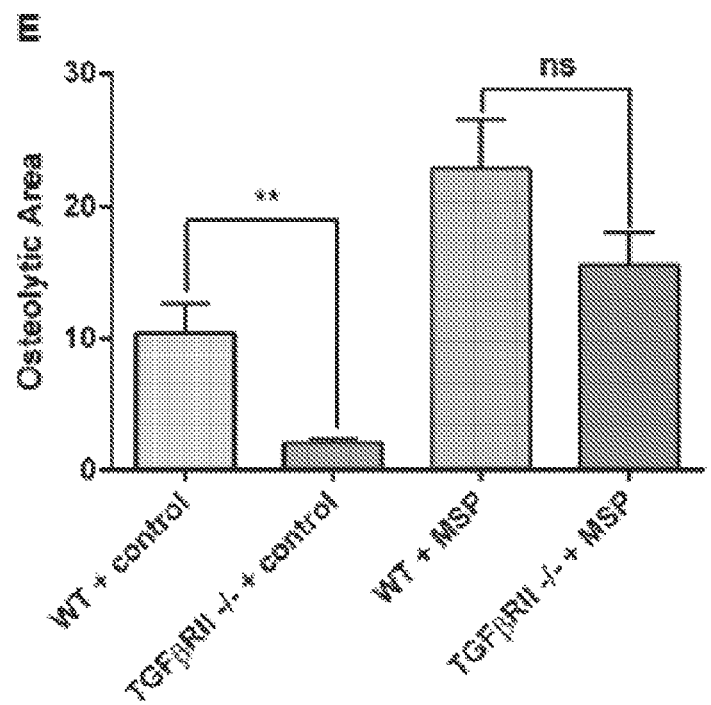
FIG. 4E is a bar chart showing the osteolytic area in bone lesions from mice in various experimental groups.

The TGFβ pathway has also been shown to be an integral part of the "vicious cycle." TGFβ is released from the bone matrix by osteoclasts and binds to its receptor on tumor cells, stimulating production of pro-osteoclastogenic cytokines. RANKL-independent mechanisms of osteolysis involving TGFβ may exist; therefore, it is possible that MSP/RON functionally interacts with the TGFβ pathway to induce osteoclast activation. To test this possibility, PyMT tumor cells were used in which the TGFβ type-II receptor (TGFβRII) had been deleted using a Cre-lox system (Forrester et al. Cancer Res. 15 2005, 65, 2296-302). MSP was then overexpressed and these cells were injected into WT mice. While the absence of TGFβ signaling did not affect tumor growth, it did affect the ability of control tumors to induce basal levels of osteolysis (FIG. 4D and FIG. 4E). FIG. 4D shows X-ray images of PyMT bone lesions arising from tumors in the presence or absence of TGFβRII. Mice were sacrificed 38 days post tumor cell injection for analysis. FIG. 4E shows quantification of osteolytic area in bone lesions from mice in each experimental group (n=5; p=0.0041; ns=not significant). Similar to RANKL inhibition, TGFβRII loss in the tumor cells impaired the ability of control tumors to induce osteolysis. This again supports the notion that the basal level of osteolysis induced by PyMT control tumor cells is dependent on RANKL and TGFβ signaling. Tumors overexpressing MSP, in contrast, caused robust osteolysis regardless of whether they expressed TGFβRII. Taken together, this evidence suggested that, while the RANKL-TGFβ portion of the vicious cycle is active in the PyMT model of bone metastasis, MSP/RON activates osteoclasts through a mechanism that does not depend on RANKL or TGFβ.

Figure 5A:
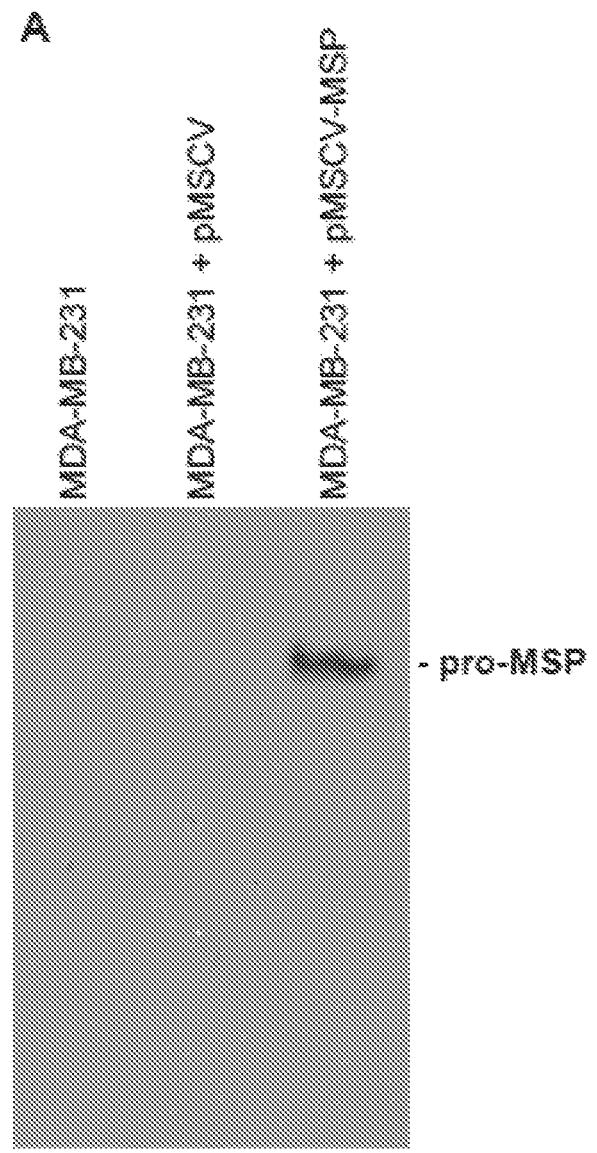
FIG. 5A is a Western blot showing MSP protein levels secreted into the media of parental, control, and MSP-overexpressing MDA-MB-231 cells.
Figure 5B:
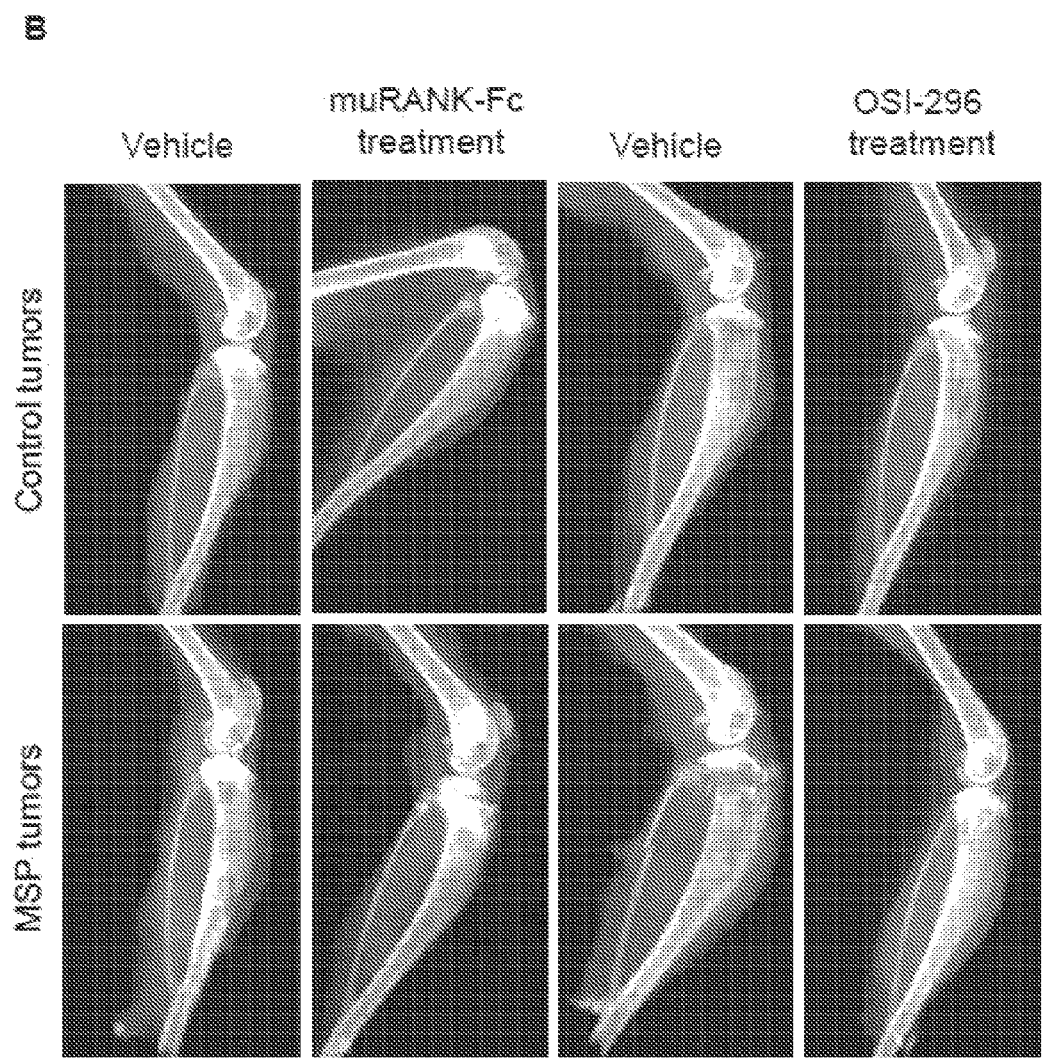
FIG. 5B is a series of X-ray images of bone lesions from NOD.SCID mice treated with muRANK-Fc or OSI-296 3 days post tumor cell injection.
Figure 5C:
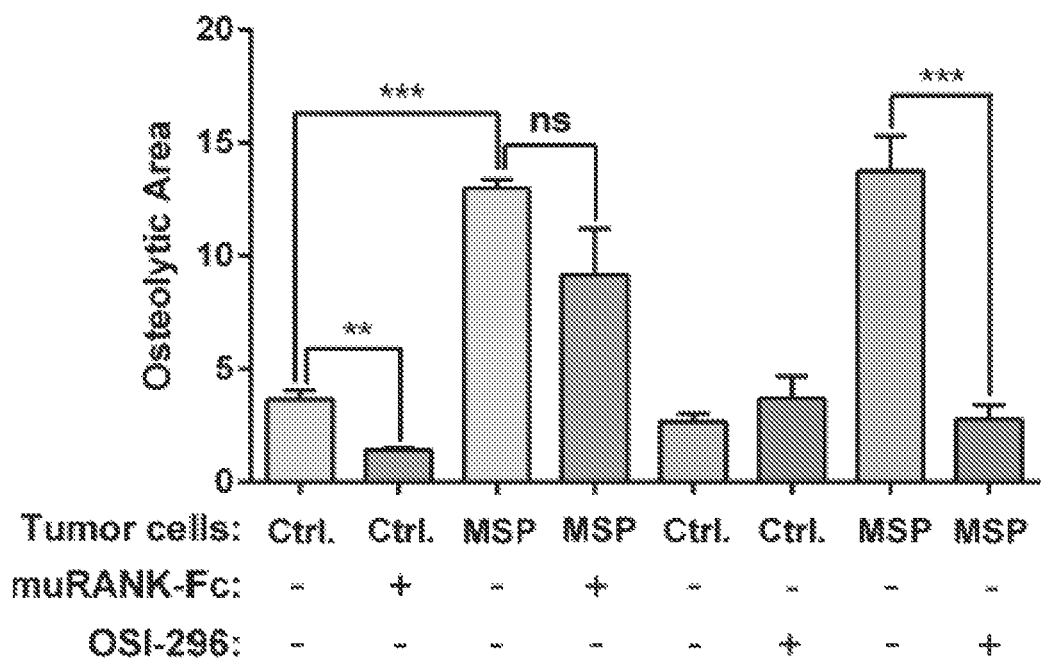
FIG. 5C is a bar chart showing the osteolytic area from bone lesions in mice from various experimental groups.

To further test the hypothesis that MSP/RON is sufficient to stimulate osteolysis in a manner that does not rely on the RANKL pathway, another human breast cancer model (MDA-MB-231) was used, which has been shown to be highly dependent on RANKL for osteolysis. Concordant with this, MDA-MB-231 cells did not express MSP at detectable levels (FIG. 5A, showing a Western blot of MSP protein levels secreted into the media of parental, control, and MSP-overexpressing MDA-MB-231 cells), allowing us to assess the consequences of MSP overexpression, which occurs in approximately 40% of human breast cancers. MSP was overexpressed in this cell line and injected these cells into the tibias of NOD.SCID mice. The expression of MSP led to a significant increase in the ability of these cells to induce osteolysis (FIG. 5B and FIG. 5C). FIG. 5B shows X-ray images of bone lesions from NOD.SCID mice treated with muRANK-Fc or OSI-296 3 days post tumor cell injection. Mice were sacrificed 30 days post tumor cell injection for analysis. FIG. 5C shows quantification of osteolytic area from bone lesions in mice from each experimental group (n=5; p=0.0014; p<0.0002; ns=not significant). While treatment with the RANKL antagonist again reduced osteolysis from control tumor cells, it did not significantly reduce the osteolysis from MSP-expressing tumor cells. Treatment with OSI-296, in contrast, was able to reduce MSP-mediated osteolysis to levels seen in control tumor cells. These data demonstrate that MSP gain-of-function can significantly increase osteolysis through a mechanism that can override RANKL dependency. Taken together, our data strongly suggested that the MSP/RON pathway is a novel mediator of osteoclast activity in bone-metastatic breast cancer.

Example 7

Figure 6A:
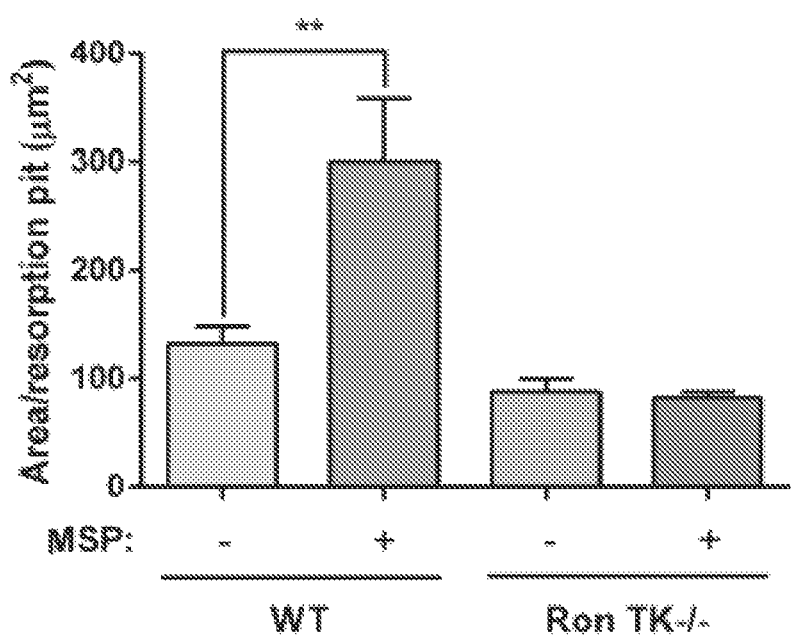
FIG. 6A is a bar chart showing the resorption area from various experimental groups.
Figure 6B:
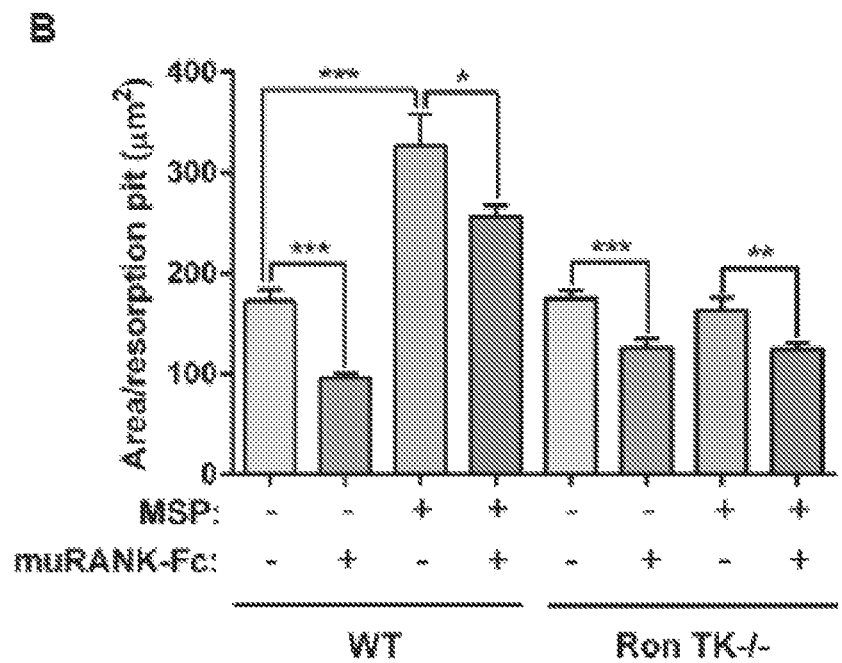
FIG. 6B is a bar chart showing the resorption area arising from WT and Ron TK−/− bone marrow precursor cells differentiated in the presence of M-CSF and RANKL for 9 days.
Figure 6C:
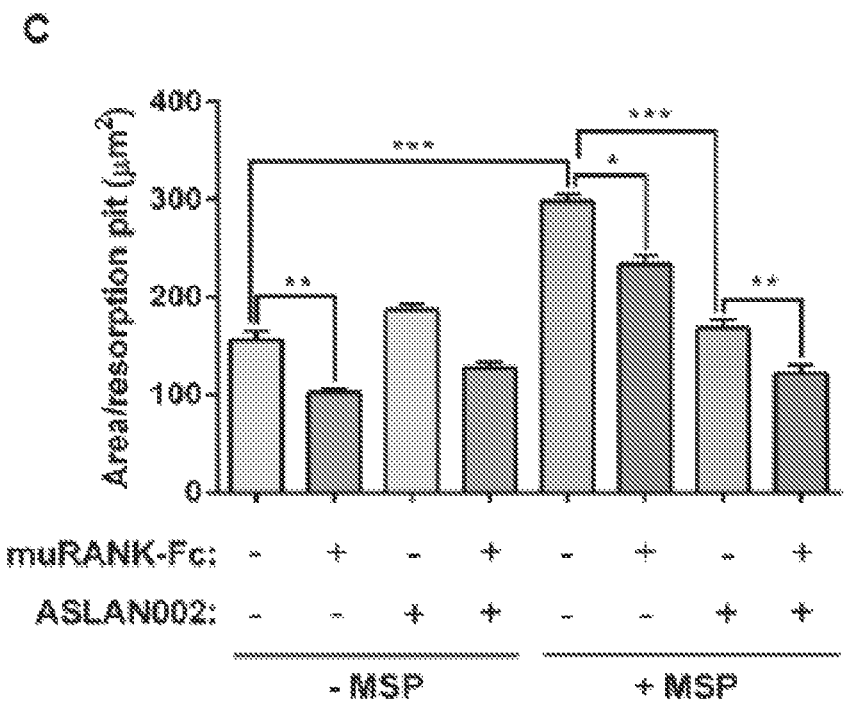
FIG. 6C is a bar chart showing the resorption area for WT bone marrow precursor cells seeded on osteologic slides and differentiated in the presence of M-CSF and RANKL for 9 days.
Figure 13A:
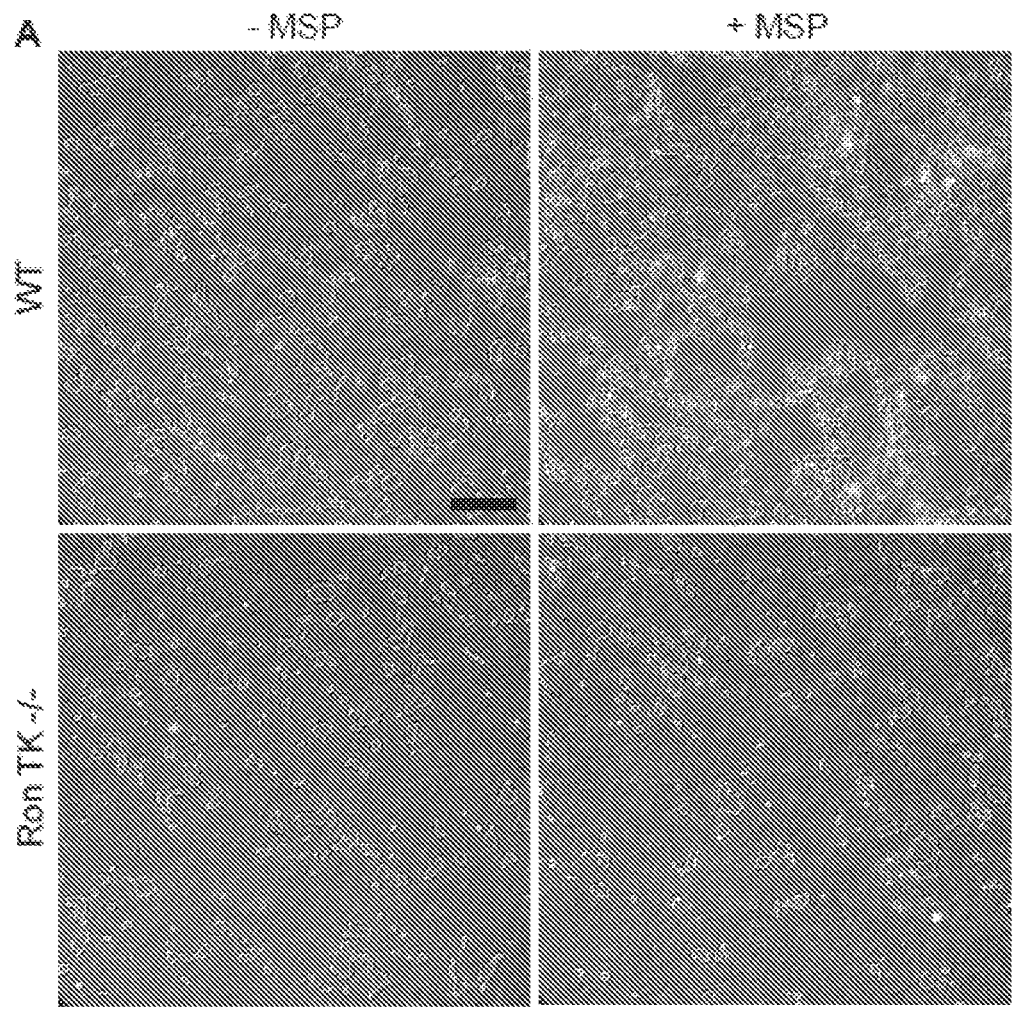
FIG. 13A is a series of representative images of resorption pits from WT and RonTK−/− osteoclasts in the presence and absence of MSP.
Figure 13B:
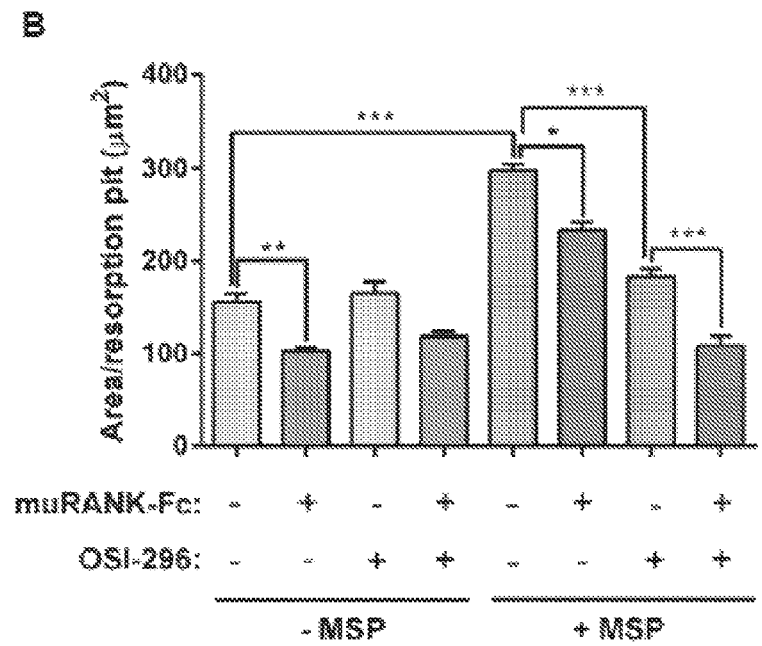
FIG. 13B is a bar chart showing the resorption area in various experimental groups.

MSP/RON Signaling Promotes Bone Degradation by Stimulating RANK-Independent Osteoclast Survival, c-Src Phosphorylation, and Osteolytic Activity To determine the cellular mechanism by which RON signaling functions in specific steps during osteoclastogenesis and osteoclast activation, the effect of MSP on osteoclasts was analyzed in vitro. Differentiated osteoclasts were stimulated with recombinant MSP, and their ability to resorb an artificial bone matrix was analyzed. Addition of MSP to WT osteoclasts led to a significant increase in the resorptive capacity of these cells, while having no effect on RonTK−/− osteoclasts (FIG. 6A and FIG. 13A). FIG. 6A shows quantification of the resorption area from each experimental group (n=4). Bone marrow precursor cells were differentiated in the presence of M-CSF and RANKL for 9 days. 100 pg/mL of MSP was added daily beginning on day 9 with the experiment ending on day 12 (p<0.001). FIG. 13A shows representative images of resorption pits from WT and RonTK−/− osteoclasts in the presence and absence of MSP. This increase in osteoclast resorption was only slightly reduced upon addition of the RANKL antagonist muRANK-Fc (FIG. 6B), but was dramatically reduced upon addition of RON inhibitors ASLAN002 or OSI-296 (FIG. 6C and FIG. 13B). FIG. 6B shows quantification of the resorption area arising from WT and Ron TK−/− bone marrow precursor cells differentiated in the presence of M-CSF and RANKL for 9 days (n=3). 10 μg/mL of muRANK-Fc was added daily beginning on day 9 with the experiment ending on day 12 (***p<0.0001, *p=0.04, p=0.0097). FIG. 6C shows quantification of the resorption area (n=3). WT bone marrow precursor cells were seeded on osteologic slides and differentiated in the presence of M-CSF and RANKL for 9 days. muRANK-Fc at a concentration of 10 μg/mL and/or ASLAN002 at a concentration of 10 μM was added daily beginning on day 9 with the experiment ending on day 12 (*p=0.0001, *p=0.01, p<0.005). FIG. 13B shows quantification of resorption area in each experimental group (n=3). WT bone marrow precursor cells were seeded on osteologic slides and differentiated in the presence of M-CSF and RANKL for 9 days. muRANK-Fc at a concentration of 10 μg/mL and/or OSI-296 at a concentration of 10 μM was added daily beginning on day 9, ending on day 12 (p=0.002, ***p<0.0001, *p=0.03). Simultaneous treatment with the RANKL antagonist and either of the RON inhibitors reduced osteoclast activity to a greater extent than either treatment alone (FIG. 6C and FIG. 13B), again suggesting that both RON and RANKL contribute to bone destruction, but do so through separate pathways in osteoclast activation.

Figure 13C:
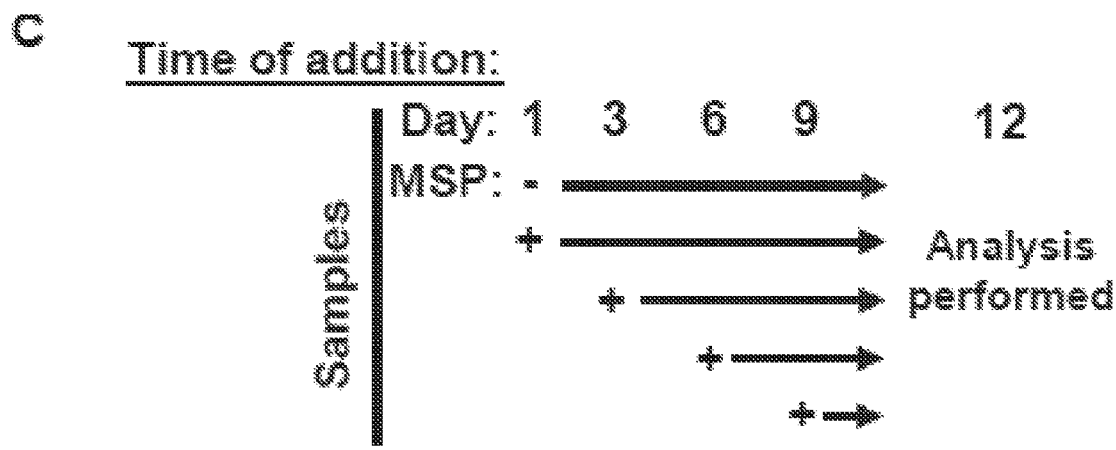
FIG. 13C is a timeline describing the addition of MSP during differentiation.
Figure 13D:
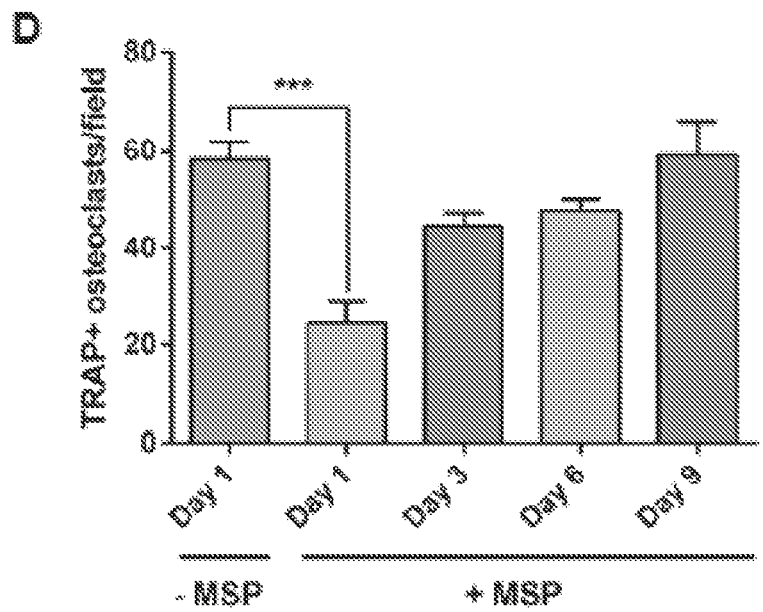
FIG. 13D is a bar chart showing TRAP+ osteoclasts in various experimental groups.
Figure 13E:
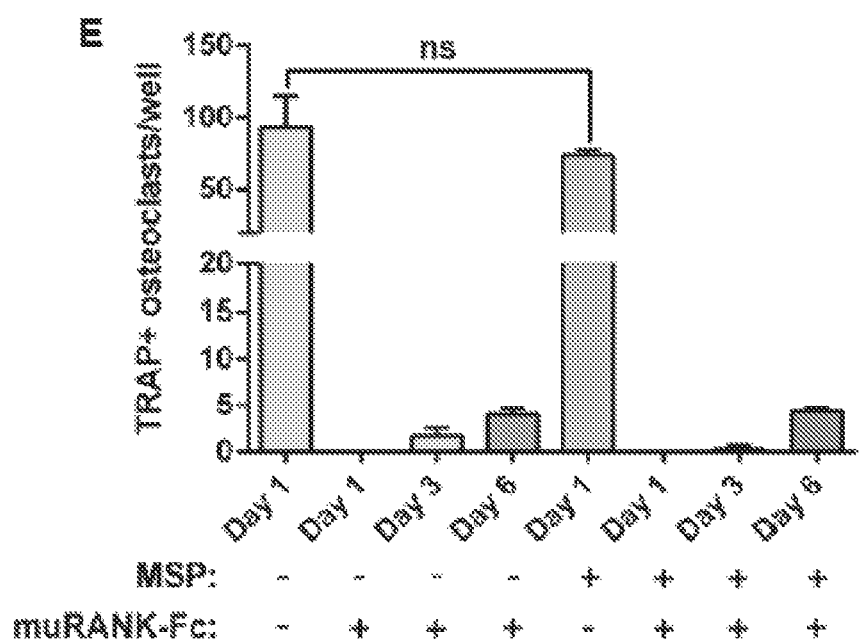
FIG. 13E is a bar chart showing the number of TRAP+ osteoclasts per well for various experimental groups.
Figure 13F:
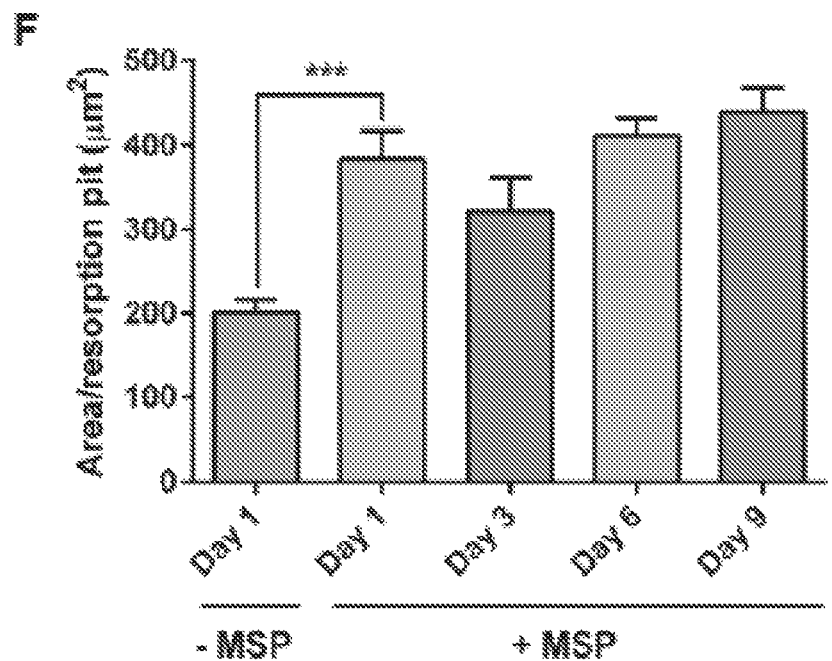
FIG. 13F is a bar chart showing the resorption area in various experimental groups.

As expected from the observations in vivo, MSP stimulation did not increase osteoclast differentiation, and even demonstrated an inhibitory effect when added at early time points relative to the onset of differentiation (FIG. 13C and FIG. 13D). FIG. 13C shows a timeline describing the addition of MSP during differentiation. M-CSF and RANKL were present continuously beginning on day 1 until experimental analysis. FIG. 13D shows quantification of TRAP+ osteoclasts in each experimental group (n=3). WT bone marrow precursor cells were seeded on glass coverslips and differentiated in the presence of M-CSF and RANKL. 100 pg/mL of recombinant MSP was added daily, beginning at the time points indicated. TRAP+ cells were identified by fluorescent TRAP stain and cells with 4 or more nuclei were counted (*p<0.0001). MSP was not sufficient for differentiation when added at any time during the differentiation process (FIG. 13E). FIG. 13E shows quantification of the number of TRAP+ osteoclasts per well for each experimental group (n=3). WT bone marrow precursor cells were seeded onto glass coverslips and differentiated in the presence of M-CSF and RANKL. RANKL was removed from the media, and 100 pg/mL of recombinant MSP was added at the indicated time points with the experiment terminating on day 9. This suggested that RANKL is required to prime these cells for cell fate determination and differentiation, similar to that of other factors which have been shown to activate osteoclasts. The ability of these cells to resorb matrix as they differentiated was also tested. Interestingly, MSP was able to stimulate osteoclast resorption of RANKL-differentiated osteoclast precursor cells, even when added at very early time points (FIG. 13F). FIG. 13F shows quantification of resorption area in each experimental group (n=3). WT bone marrow precursor cells were seeded on osteologic slides and differentiated in the presence of M-CSF and RANKL for 9 days. 100 pg/mL of recombinant MSP was added at the indicated time points with the experiment terminating on day 12 (*p<0.0001, *p=0.01, **p=0.0023). Together, these data suggested that RANKL is required for osteoclast differentiation, but can be dispensable for the resorptive activity of fully-differentiated osteoclasts when MSP is present.

Figure 6D:
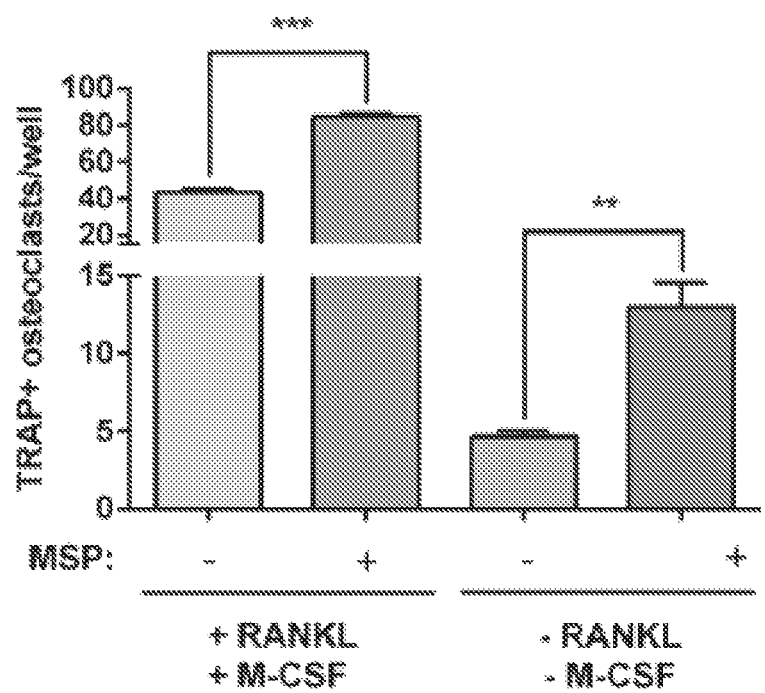
FIG. 6D is a bar chart showing the number of TRAP+ osteoclasts per well from various experimental groups.
Figure 13G:
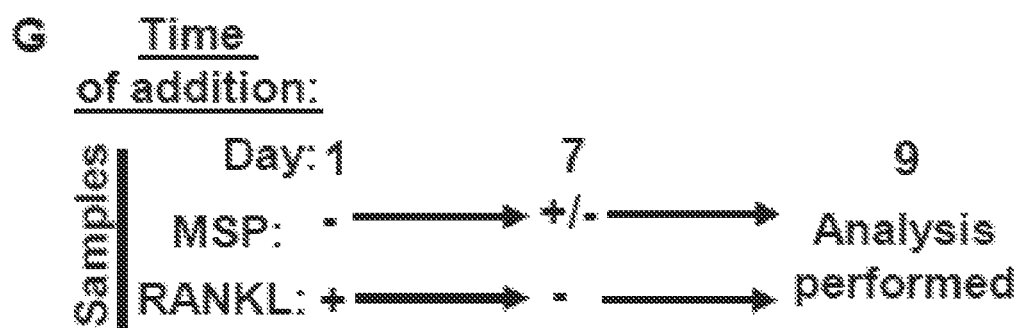
FIG. 13G is a timeline describing the addition of MSP and removal of RANKL to determine osteoclast survival.

Because RANK signaling is thought to be required for osteoclast survival, it was questioned whether MSP could affect the survival of existing osteoclasts in the absence of RANKL. To determine this, osteoclasts were fully differentiated in the presence of M-CSF and RANKL. These factors were then removed from the culture and MSP was added, see schematic in FIG. 13G, which is a timeline describing the addition of MSP and removal of RANKL to determine osteoclast survival. Cells were cultured in the presence of M-CSF and RANKL for 7 days. These factors were then removed from the culture, and 100 pg/mL of MSP was added daily, beginning on day 7, and continued for 48 hours. The cells were cultured for an additional 48 hours and osteoclast survival was determined by counting the number of TRAP+ cells present. While the number of surviving osteoclasts was reduced in all conditions tested without RANKL and M-CSF, the number of surviving osteoclasts was significantly augmented in the presence of MSP (FIG. 6D). FIG. 6D shows quantification of the number of TRAP+ osteoclasts per well from each experimental group (n=3). WT bone marrow precursor cells were differentiated in the presence of M-CSF and RANKL for 7 days. M-CSF and RANKL were washed out and 100 pg/mL of MSP was added daily, beginning on day 7, and continued for 48 hours. TRAP+ cells were identified by fluorescent TRAP stain and cells with 4 or more nuclei were counted (p<0.007, *p<0.0001). These experiments demonstrated that the MSP/RON pathway does not promote osteoclast differentiation, but instead functions to stimulate osteoclast activity and survival.

Figure 6E:
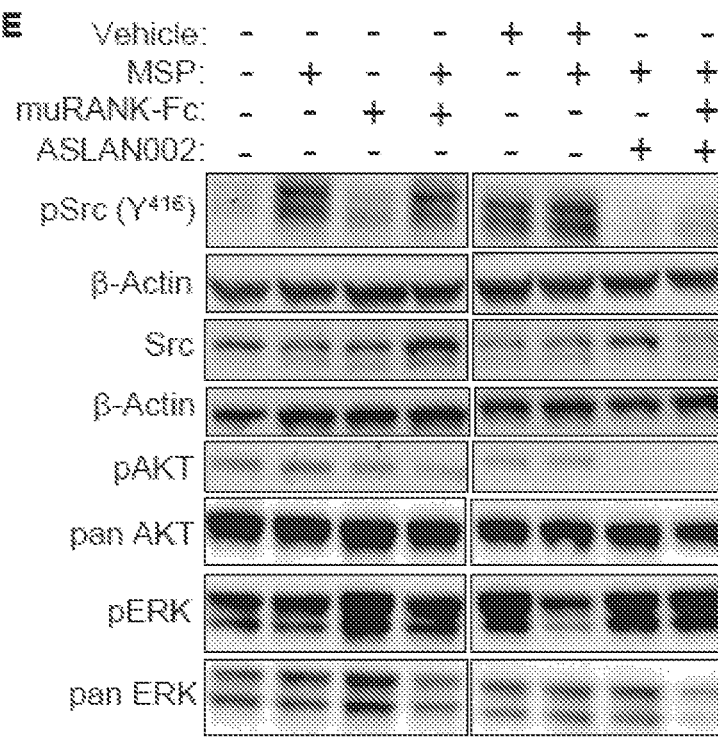
FIG. 6E is a pair of Western blots of osteoclast lysates from WT cells treated with MSP, muRANK-Fc, and/or ASLAN002.
Figure 6F:
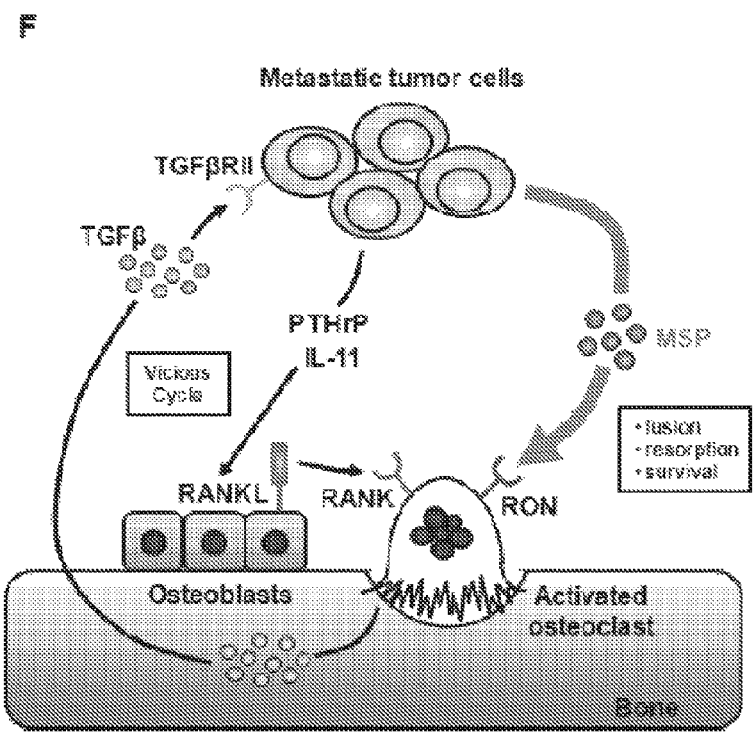
FIG. 6F is an illustration showing MSP/Ron function in the bone microenvironment.
Figure 17A:
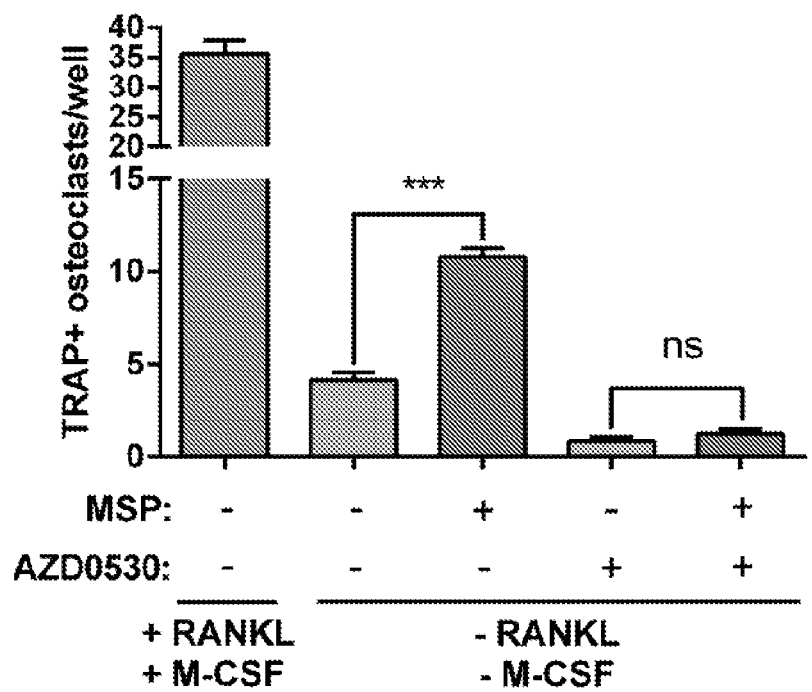
FIG. 17A is graph of the number of TRAP+ osteoclasts per well of WT bone marrow precursor cells differentiated in the presence of M-CSF and RANKL, with M-CSF and RANKL then washed out, and 100 pg/mL of MSP and/or 10
Figure 17B:
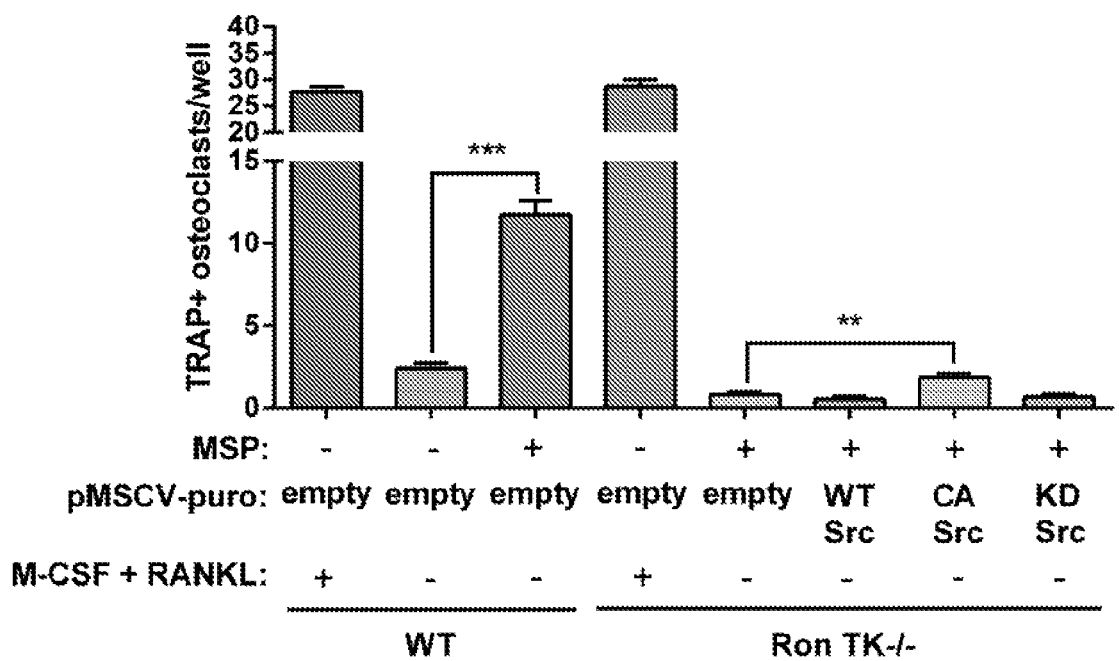
FIG. 17B is a graph of the number of TRAP+ osteoclasts per well in the presence or absence of MSP.
Figure 17C:
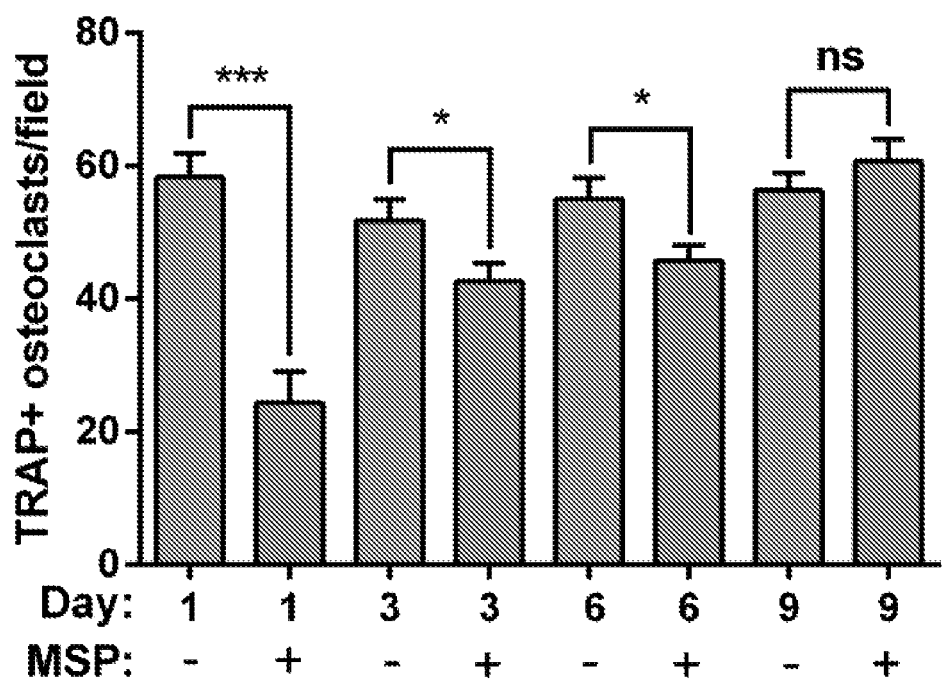
FIG. 17C is a graph of TRAP+ osteoclasts in WT bone marrow precursor cells differentiated in the presence of M-CSF and RANKL, with or without MSP added daily.

MSP promoted osteoclast survival (FIG. 13G, FIG. 17A), but not differentiation (FIG. 13C, FIG. 13E, FIG. 17C), in the absence of RANKL signaling. Shown in FIG. 17A is quantification of the number of TRAP+ osteoclasts per well from each experimental group (n=3 per group), wherein WT bone marrow precursor cells were differentiated in the presence of M-CSF and RANKL for 7 days. M-CSF and RANKL were then washed out and 100 pg/mL of MSP and/or 10 μM of the Src inhibitor AZD0530 were added daily, beginning on day 7, and continued for 48 hours. TRAP+ cells were identified by fluorescent TRAP stain and cells with 4 or more nuclei were counted (***p<0.0001; ns=not significant). Shown in FIG. 17C is quantification of TRAP+ osteoclasts in each experimental group (n=3 per group), wherein WT bone marrow precursor cells were seeded on glass coverslips and differentiated in the presence of M-CSF and RANKL. 100 pg/mL of recombinant MSP was added daily, beginning at the time points indicated. TRAP+ cells were identified by fluorescent TRAP stain, and cells with four or more nuclei were counted. Data in the figure represent mean+/− SEM; p values were based on Student's t test (*p<0.01; *p<0.0001; ns, not significant). With regard to survival, a small molecule inhibitor of Src kinase blocked MSP-mediated survival (FIG. 13G, FIG. 17B) and expression of constitutively active Src led to a small but statistically significant increase in survival of Ron TK−/− osteoclasts in the absence of RANKL signaling (FIG. 17B). Shown in FIG. 17B is quantification of the number of TRAP+ osteoclasts per well in the presence or absence of MSP (n=3 per group). Ron TK−/− bone marrow precursor cells were transduced with WT, constitutively active (CA), or kinase dead (KD) Src. The cells were then differentiated in the presence of M-CSF and RANKL for 7 days. M-CSF and RANKL were then washed out and 100 pg/mL of MSP was added daily to activate the osteoclasts, beginning on day 7 for 48 hours. TRAP+ cells were identified by fluorescent TRAP stain and cells with 4 or more nuclei were counted (*p<0.0001; **p<0.001). Together, these data suggest that RANKL (not Ron) promotes osteoclast differentiation, but both Ron and RANKL contribute to osteoclast survival and activity through separate pathways that may converge on Src signaling.

c-Src is critical in the regulation of osteoclast survival, motility, cytoskeletal reorganization, and resorption ability. To determine whether MSP/RON signaling stimulates c-Src activity independently of RANK, c-src phosphorylation was tested in the presence or absence of RANKL signaling. Addition of the RANKL antagonist to WT osteoclasts resulted in a decrease in phosphorylated c-Src. Addition of MSP to WT osteoclasts increased Src phosphorylation, which was blocked by ASLAN002, but not muRANK-Fc (FIG. 6E). However, MSP was able to rescue the loss of phosphorylated c-Src, indicating that the MSP/RON pathway functions as an alternative pathway of c-Src activation in the absence of RANKL signaling (FIG. 6E showing Western blots of osteoclast lysates from WT cells treated with MSP, muRANK-Fc, and/or ASLAN002; and FIG. 6F showing a model of MSP/RON function in the bone microenvironment).

Figure 13H:
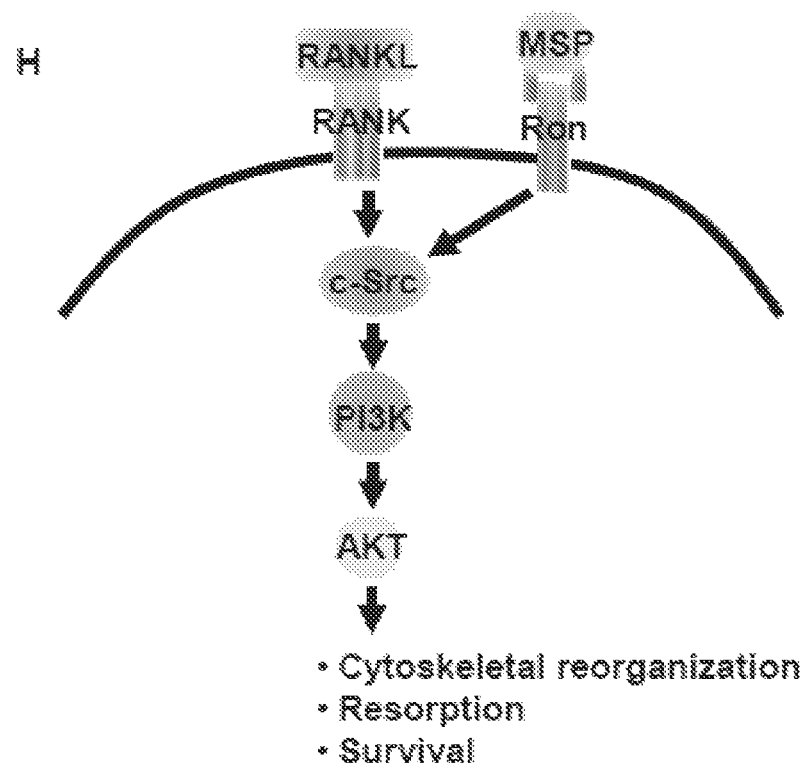
FIG. 13H is an illustration of signaling pathways activated downstream of RON activation in osteoclasts.
Figure 16:
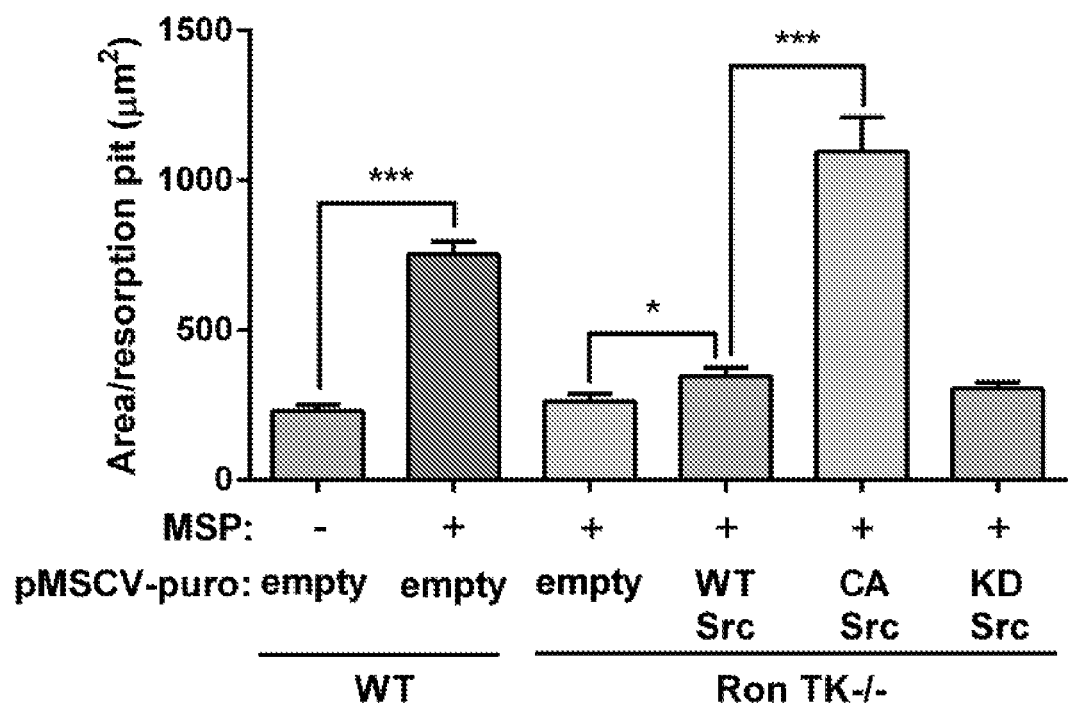
FIG. 16 is a graph of resorption area from Ron TK−/− bone marrow precursor cells transduced with WT, constitutively active (CA), or kinase dead (KD) Src in the presence or absence of MSP, with WT osteoclasts as control (n=3 per group).

ASLAN002 treatment also reduced downstream Src signaling, as demonstrated by the decrease in phosphorylated AKT, while having no effect on ERK activity. To determine whether Src activation could rescue the poor resorptive activity of RonTK−/− osteoclasts, RonTK−/− osteoclast precursors were transduced with WT Src, constitutively-active Src, or kinase-dead Src mutants. Expression of WT Src led to a slight but statistically significant increase in the resorptive ability of RonTK−/− osteoclasts, while constitutively active Src fully rescued resorption, and the kinase-dead Src mutant had no effect (FIG. 16, showing quantification of resorption area from Ron TK−/− bone marrow precursor cells transduced with WT, constitutively active (CA), or kinase dead (KD) Src in the presence or absence of MSP, with WT osteoclasts as control (n=3 per group); where indicated, 100 pg/mL of MSP was added daily beginning on day 9 with the experiment ending on day 12; *p<0.01; ***p<0.0001). Taken together, these data suggested that (1) RON plays a critical role in a signaling pathway that is known to be essential for osteoclast activity (FIG. 13H, showing a model of signaling pathways activated downstream of RON activation in osteoclasts); (2) Ron signaling promotes both survival and activity of osteoclasts through a parallel pathway to RANK signaling; and (3) c-Src kinase activity is necessary and sufficient for Ron-dependent osteoclast resorption but not sufficient to rescue survival of osteoclasts deprived of both RANKL and Ron signaling (FIG. 6F).

Example 8

RON Expression in the Host is Required for Ovariectomy-Induced Bone Loss

Figure 7A:
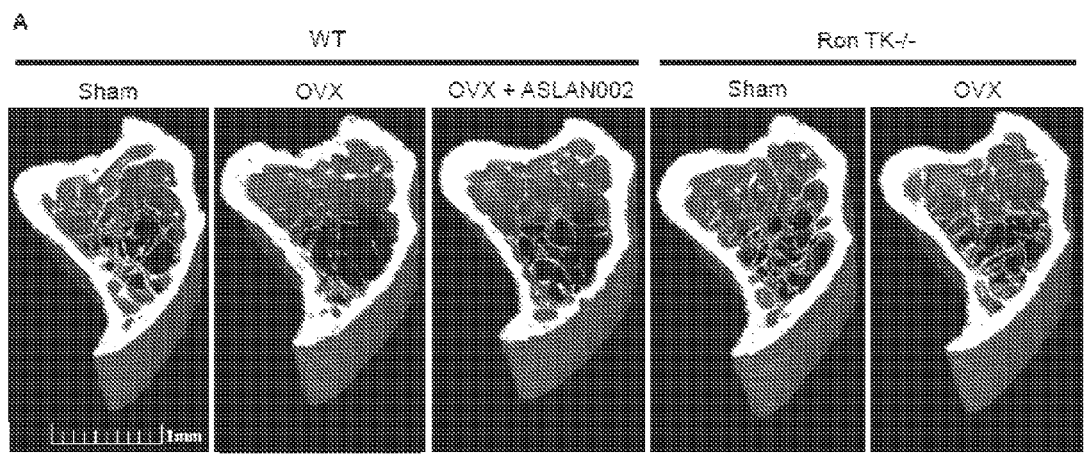
FIG. 7A is a series of μCT scans of the proximal tibia (axial view of the metaphyseal region) from WT and Ron TK−/− mice following ovariectomy (OVX) or sham operation.
Figure 7B:
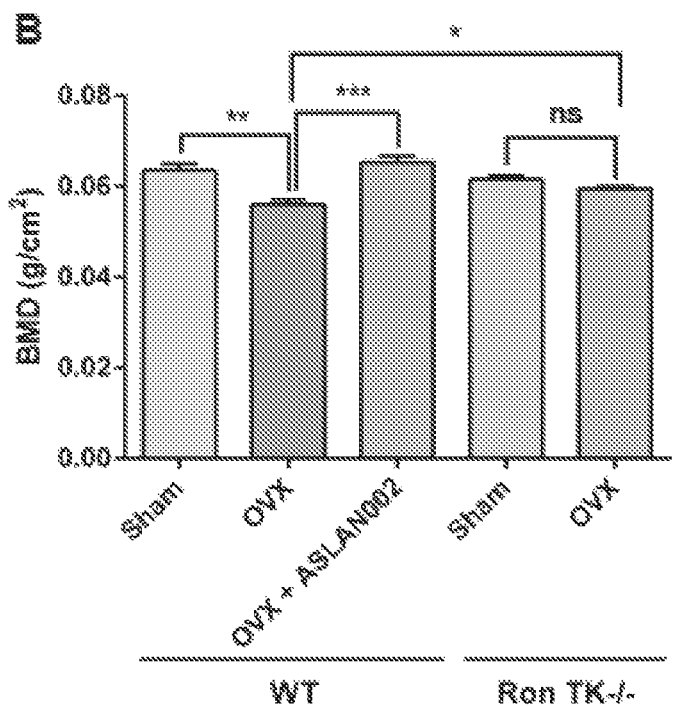
FIG. 7B is a bar chart showing the bone mineral density in the metaphyseal region of the tibia determined by bone histomorphometry analysis.
Figure 7C:
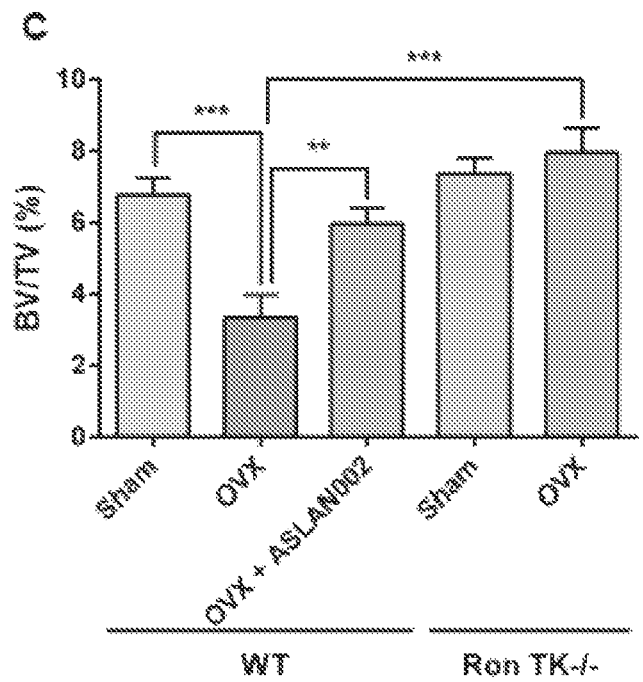
FIG. 7C is a bar chart showing trabecular bone volume in the tibia expressed at percent per total volume and determined by bone histomorphometry analysis.
Figure 7D:
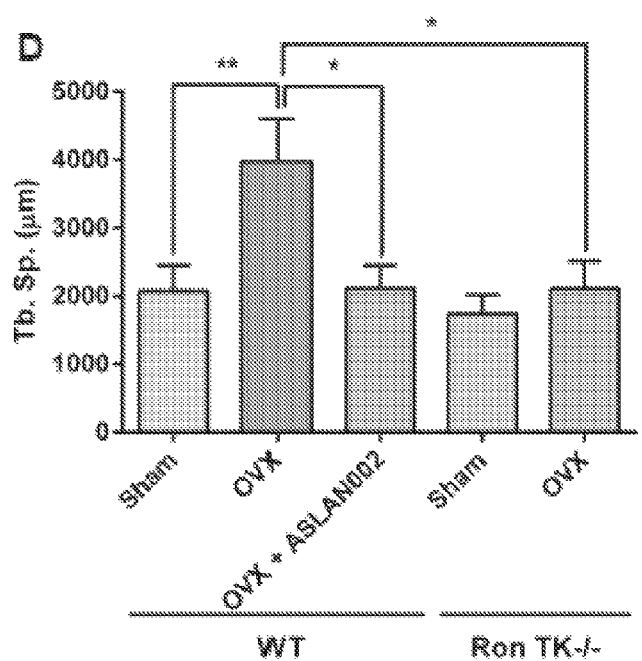
FIG. 7D is a bar chart showing trabecular separation in the tibia.
Figure 7E:
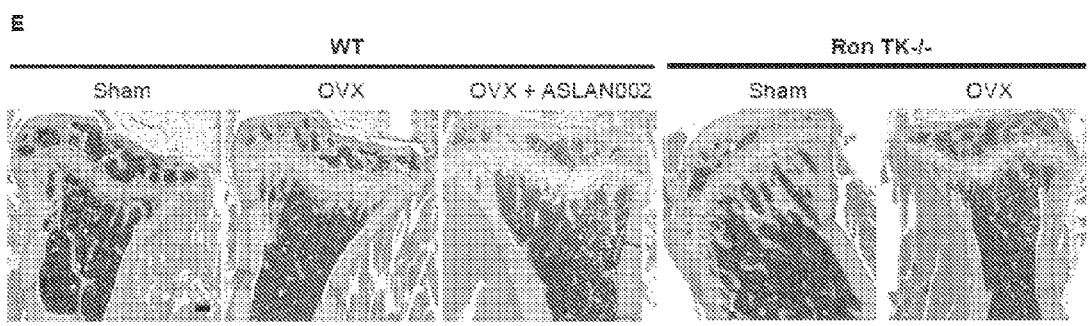
FIG. 7E is a series of images showing representative sections of the stained tibia from various experimental groups.

Pathways involved in tumor-driven osteolysis are also often implicated in other pathologies leading to bone destruction. To investigate the role of the MSP/RON pathway in bone loss due to post-menopausal osteoporosis, ovariectomies were performed in WT and RonTK−/− mice and bone loss was analyzed by dual-energy X-ray absorptiometry (DXA) and bone histomorphometry 28 days later. The ovarectomized RonTK−/− mice were more resistant to loss of bone mineral density (BMD), bone volume, and trabecular thickness, with a concomitant decrease in trabecular spacing as compared to WT mice or sham-operated controls (FIG. 7A-E). FIG. 7A shows μCT images of the proximal tibia (axial view of the metaphyseal region) from WT and RonTK−/− mice following ovariectomy (OVX) or sham operation. WT OVX mice were treated with ASLAN002 beginning 1 day post-ovariectomy. Mice were sacrificed 28 days post-ovariectomy for analysis. FIG. 7B shows quantification of bone mineral density in the metaphyseal region of the tibia determined by bone histomorphometry analysis (n=5; p<0.005, *p<0.0005, and *p<0.02). FIG. 7C shows quantification of trabecular bone volume in the tibia expressed at percent per total volume and determined by bone histomorphometry analysis (n=5; **p<0.0001, *p<0.002). FIG. 7D shows quantification of trabecular separation in the tibia (n=5; **p<0.008, *p<0.05). FIG. 7E shows representative sections of tibia stained from various experimental groups. Loss of Ron activity protected from osteoporotic bone loss.

Figure 14A:
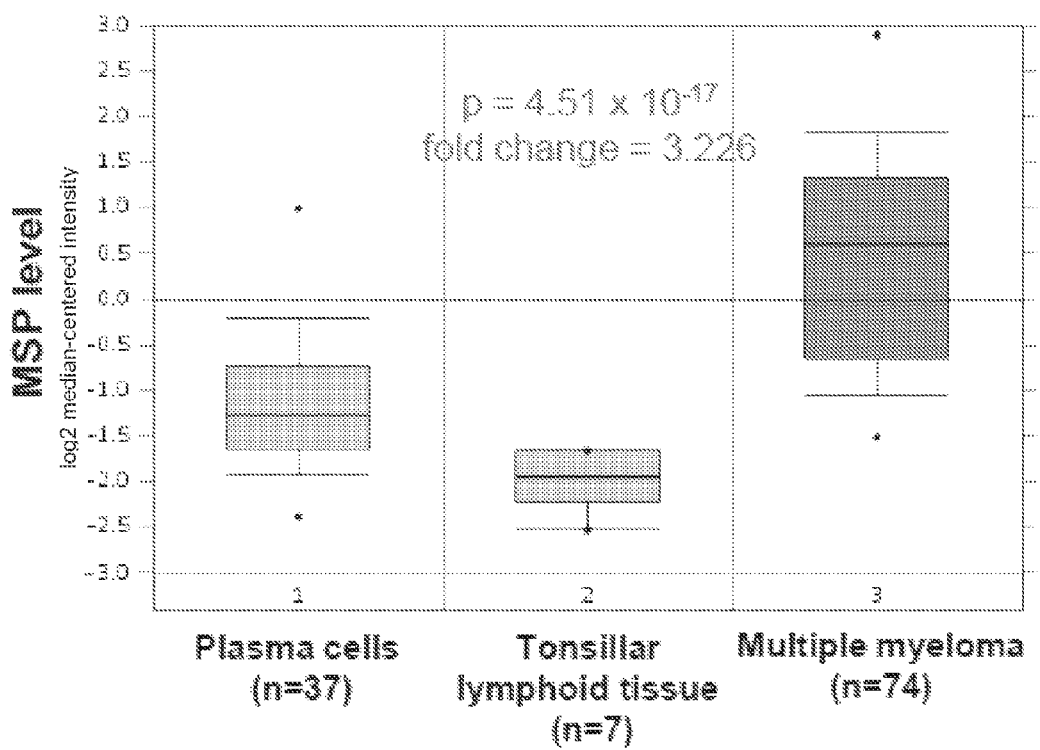
FIG. 14A is a chart of the expression of MSP in normal plasma cells versus myeloma cells.
Figure 14A:
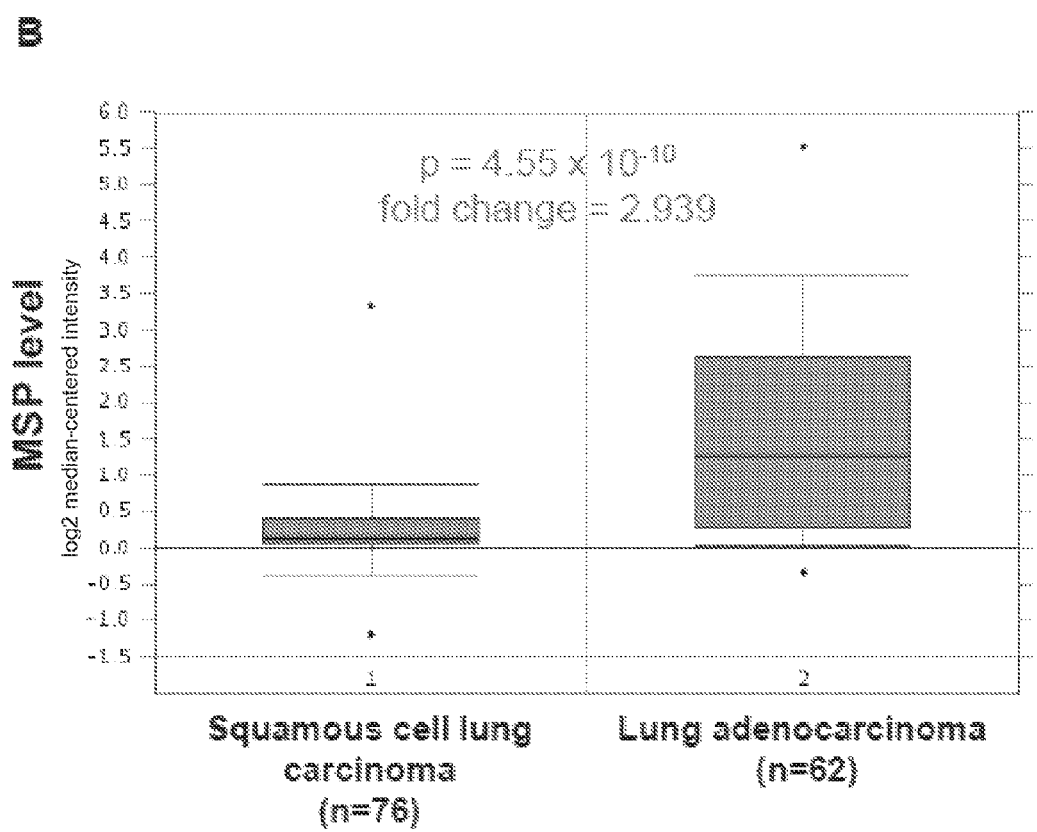

In fact, loss of RON resulted in complete protection from osteoporosis, as RonTK−/− bones were not statistically different than sham-operated controls. There also was no difference in the bone histomorphometric parameters between sham-operated mice of either genotype, demonstrating that there are no basal differences in bone density in the RonTK−/− mice under normal physiologic conditions. Importantly, treatment with ASLAN002 after ovary removal also completely prevented bone loss (FIG. 7A-E). These data further showed that MSP/RON activity is a critical pathway for osteoclast activation both in physiological and pathological states. FIG. 14A shows expression of MSP in normal plasma cells versus myeloma cells. FIG. 14B shows expression of MSP in lung carcinomas.

Example 9

ASLAN002 Reduces Bone Turnover in Postmenopausal Women

Figure 15A:
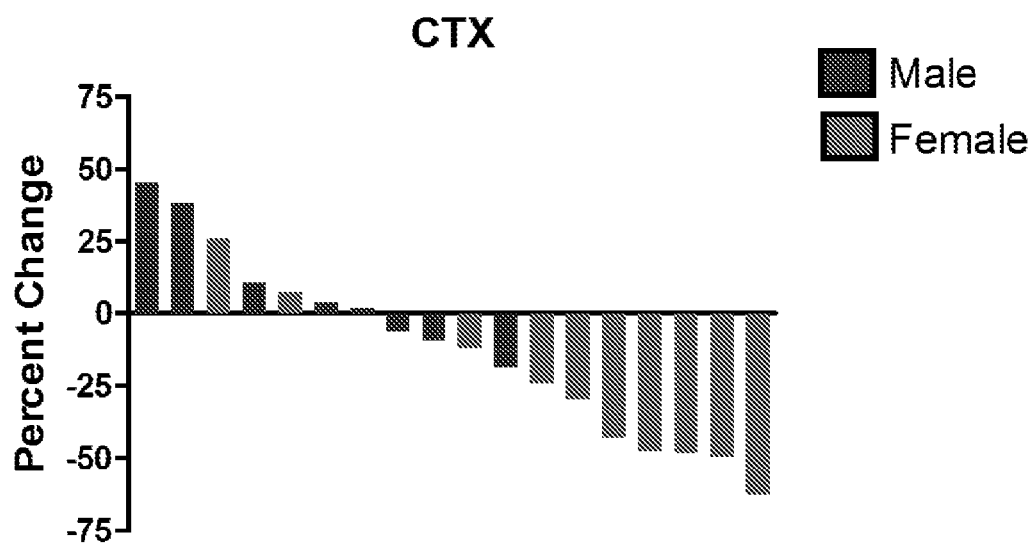
FIG. 15A is a graph of the percent change in plasma CTX levels compared to baseline prior to drug treatment for patients receiving ASLAN002 in a Phase I clinical trial.
Figure 15B:
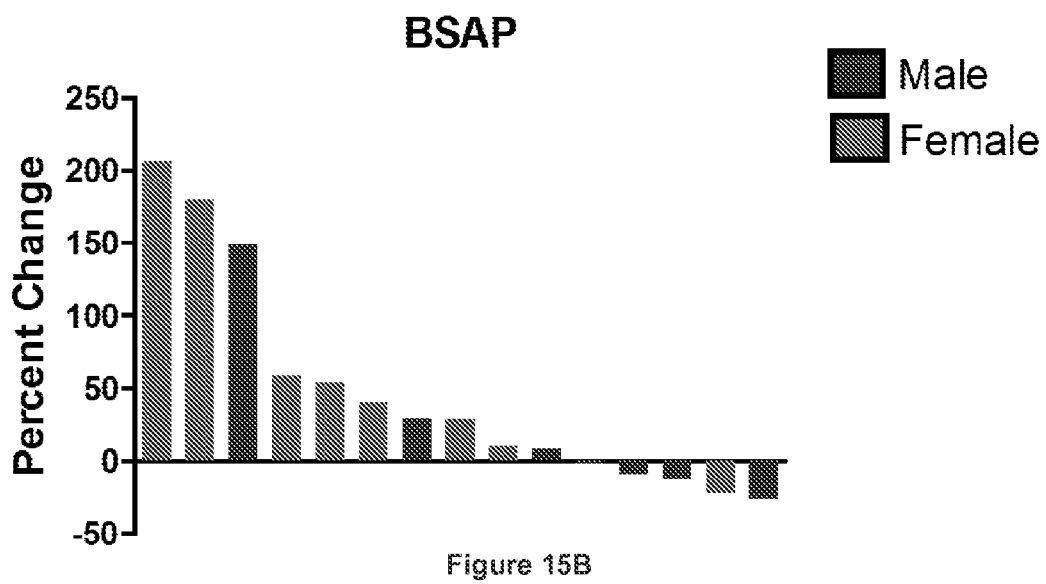
FIG. 15B is a graph of the percent change in BSAP levels (compared to baseline) in blood plasma of patients receiving ASLAN002.

ASLAN002 is currently in Phase I testing as an anti-cancer agent (NCT01721148). Regardless of cancer diagnosis, and even in the absence of bone metastasis, RON inhibition might affect normal bone turnover, especially in postmenopausal women due to their high rate of bone loss. Plasma samples from early cohorts of Phase I patients were examined for evidence of bone turnover at baseline and after treatment with ASLAN002, using a standard clinical test to detect cleaved bone-derived collagen in plasma (beta-cross-linked C-telopeptide, or CTX). These data showed that 11/18 (61%) of patients exhibited decreased CTX levels with ASLAN002 treatment, and 64% of those had a sufficient drop in CTX levels (≥25% reduction) to meet the Mayo clinic guidelines for response to bone anti-resorptive therapies (FIG. 15A). Shown in FIG. 15A is quantification of the percent change in plasma CTX levels (compared to baseline prior to drug treatment) in blood plasma of patients receiving ASLAN002 in the Phase I clinical trial. Most patients received ASLAN002 for 28 days; the exceptions in duration are noted (*15 days and ^84 days). Dark bars represent males, and light bars represent females. Interestingly, the best responses were seen in women, where 7/10 women (70%) showed ≥25% decreases in CTX (versus 0/8 men). In this analysis, all subjects except one were >50 years old; women older than 50 were expected to have the greatest amount of physiologic bone turnover due to menopause. None of the patients analyzed were treated concurrently with anti-osteoporotic agents. The decrease in CTX was not due to non-specific changes in bone turnover, since bone-specific alkaline phosphatase levels (BSAP, a marker of osteoblast activity) did not decrease with ASLAN002 treatment. Rather, increased plasma BSAP was noted, suggesting bone repair (FIG. 15B). Shown in FIG. 15B is quantification of the percent change in BSAP levels (compared to baseline) in blood plasma of patients receiving ASLAN002. The patients are the same as those shown in FIG. 15A, except those receiving only 15 days of ASLAN002 were not tested for BSAP. Dark bars represent males, and light bars represent females. Note that these patients were not selected based on a diagnosis of bone metastasis; rather, markers of bone turnover in patients with various cancer diagnoses who participated in the Phase I trial of ASLAN002 were simply assessed. These correlative data, when taken together with the pre-clinical data in animal models, strongly suggested that inhibition of Ron reduces osteoclast activity. These results provide rationale for continued investigation of Ron inhibitors to treat bone destructive diseases like osteolytic bone metastasis and osteoporosis.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method for inhibiting osteolysis or treating osteoporosis in a subject in need thereof, the method comprising administering to the subject an effective amount of at least one RON inhibitor.

Clause 2. The method of clause 1, wherein the subject has been diagnosed with a condition selected from the group consisting of inflammation, cyst, and cancer.

Clause 3. The method of any one of the above clauses, wherein the subject has been diagnosed with cancer with bone metastasis or cancer-mediated bone destruction.

Clause 4. The method of any one of clauses 2-3, wherein the cancer is selected from the group consisting of lymphoma, lung cancer, pancreatic cancer, breast cancer, rectal cancer, colon cancer, stomach cancer, larynx cancer, liver cancer, brain cancer, and skin cancer.

Clause 5. The method of clause 1, wherein the osteolysis is caused by a condition selected from the group consisting of tumor, inflammation, and cyst.

Clause 6. The method of clause 5, wherein the condition comprises a bone tumor or a tumor located in bone.

Clause 7. The method of clause 1, wherein the subject is premenopausal.

Clause 8. The method of clause 1, wherein the subject is menopausal.

Clause 9. The method of clause 1, wherein the subject is postmenopausal.

Clause 10. The method of any one of clauses 1-9, wherein the RON inhibitor is OSI-296.

Clause 11. The method of any one of clauses 1-9, wherein the RON inhibitor is a RON-selective inhibitor.

Clause 12. The method of clause 11, wherein the RON-selective inhibitor is ASLAN002.

Clause 13. The method of any one of clauses 1-12, wherein the RON inhibitor does not depend on the function of RANKL or TGFβ.

SEQUENCES

```
SEQ ID NO: 1
RON polypeptide, homo sapiens, 1351 amino acids, accession no. NP_001231866.
MELLPPLPQS FLLLLLLPAK PAAGEDWQCP RTPYAASRDF DVKYVVPSFS AGGLVQAMVT
YEGDRNESAV FVAIRNRLHV LGPDLKSVQS LATGPAGDPG CQTCAACGPG PHGPPGDTDT
KVLVLDPALP ALVSCGSSLQ GRCFLHDLEP QGTAVHLAAP ACLFSAHHNR PDDCPDCVAS
PLGTRVTVVE QGQASYFYVA SSLDAAVAAS FSPRSVSIRR LKADASGFAP GFVALSVLPK
HLVSYSIEYV HSFHTGAFVY FLTVQPASVT DDPSALHTRL ARLSATEPEL GDYRELVLDC
RFAPKRRRRG APEGGQPYPV LRVAHSAPVG AQLATELSIA EGQEVLFGVF VTGKDGGPGV
GPNSVVCAFP IDLLDTLIDE GVERCCESPV HPGLRRGLDF FQSPSFCPNP PGLEALSPNT
SCRHFPLLVS SSFSRVDLFN GLLGPVQVTA LYVTRLDNVT VAHMGTMDGR ILQVELVRSL
NYLLYVSNFS LGDSGQPVQR DVSRLGDHLL FASGDQVFQV PIQGPGCRHF LTCGRCLRAW
HFMGCGWCGN MCGQQKECPG SWQQDHCPPK LTEFHPHSGP LRGSTRLTLC GSNFYLHPSG
LVPEGTHQVT VGQSPCRPLP KDSSKLRPVP RKDFVEEFEC ELEPLGTQAV GPTNVSLTVT
NMPPGKHFRV DGTSVLRGFS FMEPVLIAVQ PLFGPRAGGT CLTLEGQSLS VGTSRAVLVN
GTECLLARVS EGQLLCATPP GATVASVPLS LQVGGAQVPG SWTFQYREDP VVLSISPNCG
YINSHITICG QHLTSAWHLV LSFHDGLRAV ESRCERQLPE QQLCRLPEYV VRDPQGWVAG
NLSARGDGAA GFTLPGFRFL PPPHPPSANL VPLKPEEHAI KFEVCVDGEC HILGRVVRPG
PDGVPQSTLL GILLPLLLLV AALATALVFS YWWRRKQLVL PPNLNDLASL DQTAGATPLP
ILYSGSDYRS GLALPAIDGL DSTTCVHGAS FSDSEDESCV PLLRKESIQL RDLDSALLAE
VKDVLIPHER VVTHSDRVIG KGHFGVVYHG EYIDQAQNRI QCAIKSLSRI TEMQQVEAFL
REGLLMRGLN HPNVLALIGI MLPPEGLPHV LLPYMCHGDL LQFIRSPQRN PTVKDLISFG
LQVARGMEYL AEQKFVHRDL AARNCMLDES FTVKVADFGL ARDILDREYY SVQQHRHARL
```

| SEQUENCES |
|---|
| PVKWMALESL QTYRFTTKSD VWSFGVLLWE LLTRGAPPYR HIDPFDLTHF LAQGRRLPQP<br>EYCPDSLYQV MQQCWEADPA VRPTFRVLVG EVEQIVSALL GDHYVQLPAT YMNLGPSTSH<br>EMNVRPEQPQ FSPMPGNVRR PRPLSEPPRP T<br><br>SEQ ID NO: 2<br>RON polynucleotide, *homo sapiens*, 4638 bp, accession no. NM_001244937.<br>agtgtacagc ggcggctggg gcggcaggtg aggcggctgg ggcgttgctg tcgtgcgtcc<br>gcaggcgtca ggtgctcaga cccgagggcc gggaagggat ttgggtttca caggaacctg<br>gggcggggggt ccgctatctt ggggctgtcg ggaccgctgc ttaaatttgg cccagtccag<br>acctcgagtc gggcccccag ccaggcccac gcccaggtcc aggcccaggc cggtagggat<br>cctctagggt cccagctcgc ctcgatggag ctcctcccgc cgctgcctca gtccttcctg<br>ttgctgctgc tgttgcctgc caagcccgcg gcggggcgagg actggcagtg cccgcgcacc<br>ccctacgcgg cctctcgcga ctttgacgtg aagtacgtgg tgcccagctt ctccgccgga<br>ggcctggtac aggccatggt gacctacgag ggcgacagaa atgagagtgc tgtgtttgta<br>gccatacgca atcgcctgca tgtgcttggg cctgacctga agtctgtcca gagcctggcc<br>acgggccctg ctggagaccc tggctgccag acgtgtgcag cctgtggcc aggacccccac<br>ggccctcccg gtgacacaga cacaaaggtg ctggtgctgg atcccgcgct gcctgcgctg<br>gtcagttgtg gctccagcct gcagggccgc tgcttcctgc atgacctaga gcccaaggg<br>acagccgtgc atctggcagc gccagcctgc ctcttctcag cccaccataa ccggcccgat<br>gactgccccg actgtgtggc cagcccattg ggcacccgtg taactgtggt tgagcaaggc<br>caggcctcct atttctacgt ggcatcctca ctggacgcag ccgtggctgc cagcttcagc<br>ccacgctcag tgtctatcag gcgtctcaag gctgacgcct cgggattcgc accgggcttt<br>gtggcgttgt cagtgctgcc caagcatctt gtctcctaca gtattgaata cgtgcacagc<br>ttccacacgg gagccttcgt atacttcctg actgtacagc cggccagcgt gacagatgat<br>cctagtgccc tgcacacacg cctggcacgg cttagcgcca ctgagccaga gttgggtgac<br>tatcgggagc tggtcctcga ctgcagattt gctccaaaac gcaggcgcc gggggccca<br>gaaggcggac agccctaccc tgtgctgcgg gtggcccact ccgctccagt gggtgcccaa<br>cttgccactg agctgagcat cgccgagggc caggaagtac tatttgggt cttgtgact<br>ggcaaggatg gtggtcctgg cgtgggcccc aactctgtcg tctgtgcctt ccccattgac<br>ctgctggaca cactaattga tgagggtgtg gagcgctgtt gtgaatcccc agtccatcca<br>ggcctccggc gaggcctcga cttcttccag tcgcccagtt tttgccccaa cccgcctggc<br>ctggaagccc tcagccccaa caccagctgc cgccacttcc ctctgctggt cagtagcagc<br>ttctcacgtg tggacctatt caatgggctg ttgggaccag tacaggtcac tgcattgtat<br>gtgacacgcc ttgacaacgt cacagtggca cacatgggca caatggatgg gcgtatcctg<br>caggtggagc tggtcaggtc actaaactac ttgctgtatg tgtccaactt ctcactgggt<br>gacagtgggc agcccgtgca gcgggatgtc agtcgtcttg ggaccacct actctttgcc<br>tctgggacc aggttttcca ggtacctatc caaggccctg gctgccgcca cttcctgacc<br>tgtgggcgtt gcctaagggc atggcattc atgggctgtg gctggtgtgg aacatgtgc<br>ggccagcaga aggagtgtcc tggctcctgg caacaggacc actgcccacc taagcttact<br>gagttccacc cccacagtgg acctctaagg ggcagtacaa ggctgaccct gtgtggctcc<br>aacttctacc ttcacccttc tggtctggtg cctgagggaa ccatcaggt cactgtgggc<br>caaagtcccc gccggccact gcccaaggac agctcaaaac tcagaccagt gccccggaaa<br>gactttgtag aggagtttga gtgtgaactg gagcccttgg gcacccaggc agtgggggcct<br>accaacgtca gcctcaccgt gactaacatg ccaccgggca agcacttccg ggtagacggc<br>acctccgtgc tgagaggctt ctcttttcatg gagccagtgc tgatagcagt gcaacccctc<br>tttggcccac gggcaggagg cacctgtctc actcttgaag ccagagtct gtctgtaggc<br>accagccggg ctgtgctggt caatgggact gagtgtctgc tagcacgggt cagtgagggg<br>cagcttttat gtgccacacc ccctggggcc acggtggcca gtgtcccct tagcctgcag<br>gtgggggtg cccaggtacc tggttcctgg accttccagt acagagaaga ccctgtcgtg<br>ctaagcatca gccccaactg tggctacatc aactcccaca tcaccatctg tggccagcat<br>ctaacttcag catggcactt agtgctgtca ttccatgacg gcttagggc agtgaaagc<br>aggtgtgaga ggcagcttcc agagcagcag ctgtgccgcc ttcctgaata tgtggtccga<br>gacccccagg gatgggtggc agggaatctg agtgcccgag gggatggagc tgctggcttt<br>acactgcctg gctttcgctt cctacccca cccatccac ccagtgccaa cctagttcca<br>ctgaagcctg aggagcatgc cattaagttt gaggtctgcg tagatggtga atgtcatatc<br>ctgggtagag tggtgcggcc agggccagat ggggtcccac agagcacgct ccttggtatc<br>ctgctgcctt tgctgctgct tgtggctgca ctggcgactg cactggtctt cagctactgg<br>tggcggagga agcagctagt tcttcctccc aacctgaatg acctggcatc cctggaccag<br>actgctggga ccacacccct gcctattctg tactcgggct ctgactacag aagtggcctt<br>gcactccctg ccattgatgg tctggattcc accacttgtg tccatggagc atccttctcc<br>gatagtgaag atgaatcctg tgtgccactg ctgcggaaaa agtccatcca gctaagggac<br>ctggactctg cgctcttggc tgaggtcaag gatgtgctga ttccccatga gcgggtggtc<br>acccacagtg accgagtcat ggcaaaggc cactttggag ttgtctacca cggagaatac<br>atagaccagg cccagaatcg aatccaatgt gccatcaagt cactaagtcg catcacagag<br>atgcagcagg tggaggcctt cctgcgagag gggctgctca tgcgtggcct gaaccacccg<br>aatgtgctgg ctctcattgg tatcatgttg cacctgagg gctgcccca tgtgctgctg<br>ccctatatgt gccacggtga cctgctccag ttcatccgct cacctcagcg gaacccacc<br>gtgaaggacc tcatcagctt ggcctgcag gtagcccgg gcatgagta cctggcagag<br>cagaagtttg tgcacaggga cctggctgcg cggaactgca tgctgacga gtcattcaca<br>gtcaaggtgc tgactttgg tttggcccgc gacatcctgg acagggagta ctatagtgtt<br>caacagcatc gccacgctcg cctacctgtg aagtggatgg cgctggagag cctgcagacc<br>tatagattta ccaccaagtc tgatgtgtgg tcatttggtg tgctgctgtg ggaactgctg<br>acacggggtg cccaccata ccgccacatt gaccctttg accttaccca cttcctggcc<br>cagggtcggc gcctgcccca gctgagtat gccctgatt ctctgtacca agtgatgcag<br>caatgctggg aggcagaccc agcagtgcga cccaccttca gagtactagt ggggaggtg<br>gagcagatag tgtctgcact gcttggggac cattatgtgc agctgccagc aacctacatg<br>aacttgggcc ccagcacctc gcatgagatg aatgtgcgtc cagaacagcc gcagttctca |

```
                               SEQUENCES
cccatgccag ggaatgtacg ccggcccggg ccactctcag agcctcctcg gcccacttga
cttagttctt gggctggacc tgcttagctg ccttgagcta accccaagct gcctctgggc
catgccaggc cagagggcag tggccctcca ccttgttcct gcccttttaac tttcagaggc
aataggtaaa tggggcccat taggtccctc actccacaga gtgagccagt gagggcagtc
ctgcaacatg tatttatgga gtgcctgctg tggaccctgt cttctgggca cagtggactc
agcagtgacc acaccaacac tgaccccttga accaataaag gaacaaatga ctattaaagc
acaaaaaaaa aaaaaaaa SEQ ID NO: 3
Met polypeptide, homo sapiens, 1390 amino acids, accession no. NP_000236.
MKAPAVLAPG ILVLLFTLVQ RSNGECKEAL AKSEMNVNMK YQLPNFTAET PIQNVILHEH
HIFLGATNYI YVLNEEDLQK VAEYKTGPVL EHPDCFPCQD CSSKANLSGG VWKDNINMAL
VVDTYYDDQL ISCGSVNRGT CQRHVFPHNH TADIQSEVHC IFSPQIEEPS QCPDCVVSAL
GAKVLSSVKD RFINFFVGNT INSSYFPDHP LHSISVRRLK ETKDGFMFLT DQSYIDVLPE
FRDSYPIKYV HAFESNNFIY FLTVQRETLD AQTFHTRIIR FCSINSGLHS YMEMPLECIL
TEKRKKRSTK KEVFNILQAA YVSKPGAQLA RQIGASLNDD ILFGVFAQSK PDSAEPMDRS
AMCAFPIKYV NDFFNKIVNK NNVRCLQHFY GPNHEHCFNR TLLRNSSGCE ARRDEYRTEF
TTALQRVDLF MGQFSEVLLT SISTFIKGDL TIANLGTSEG RFMQVVVSRS GPSTPHVNFL
LDSHPVSPEV IVEHTLNQNG YTLVITGKKI TKIPLNGLGC RHFQSCSQCL SAPPFVQCGW
CHDKCVRSEE CLSGTWTQQI CLPAIYKVFP NSAPLEGGTR LTICGWDPGF RRNNKFDLKK
TRVLLGNESC TLTLSESTMN TLKCTVGPAM NKHFNMSIII SNGHGTTQYS TFSYVDPVIT
SISPKYGPMA GGTLLTLTGN YLNSGNSRHI SIGGKTCTLK SVSNSILECY TPAQTISTEF
AVKLKIDLAN RETSIFSYRE DPIVYEIHPT KSFISGGSTI TGVGKNLNSV SVPRMVINVH
EAGRNFTVAC QHRSNSEIIC CTTPSLQQLN LQLPLKTKAF FMLDGILSKY FDLIYVHNPV
FKPFEKPVMI SMGNENVLEI KGNDIDPEAV KGEVLKVGNK SCENIHLHSE AVLCTVPNDL
LKLNSELNIE WKQAISSTVL GKVIVQPDQN FTGLIAGVVS ISTALLLLLG FFLWLKKRKQ
IKDLGSELVR YDARVHTPHL DRLVSARSVS PTTEMVSNES VDYRATFPED QFPNSSQNGS
CRQVQYPLTD MSPILTSGDS DISSPLLQNT VHIDLSALNP ELVQAVQHVV IGPSSLIVHF
NEVIGRGHFG CVYHGTLLDN DGKKIHCAVK SLNRITDIGE VSQFLTEGII MKDFSHPNVL
SLLGICLRSE GSPLVVLPYM KHGDLRNFIR NETHNPTVKD LIGFGLQVAK GMKYLASKKF
VHRDLAARNC MLDEKFTVKV ADFGLARDMY DKEYYSVHNK TGAKLPVKWM ALESLQTQKF
TTKSDVWSFG VLLWELMTRG APPYPDVNTF DITVYLLQGR RLLQPEYCPD PLYEVMLKCW
HPKAEMRPSF SELVSRISAI FSTFIGEHYV HVNATYVNVK CVAPYPSLLS SEDNADDEVD
TRPASFWETS SEQ ID NO: 4
Met polynucleotide, homo sapiens, 6641 bp, accession no. NM_000245.
gccctcgccg cccgcggcgc cccgagcgct ttgtgagcag atgcggagcc gagtggaggg
cgcgagccag atgcggggcg acagctgact tgctgagagg aggcgggag gcgcggagcg
cgcgtgtggt ccttgcgccg ctgacttctc cactggttcc tgggcaccga aagataaacc
tctcataatg aaggccccg ctgtgcttgc acctggcatc ctcgtgctcc tgtttacctt
ggtgcagagg agcaatgggg agtgtaaaga ggcactagca aagtccgaga tgaatgtgaa
tatgaagtat cagcttccca acttcaccgc ggaaacaccc atccagaatg tcattctaca
tgagcatcac attttccttg gtgccactaa ctacatttat gttttaaatg aggaagacct
tcagaaggtt gctgagtaca agactgggcc tgtgctggaa cacccagatt gtttcccatg
tcaggactgc agcagcaaag ccaatttatc aggaggtgtt tggaaagata acatcaacat
ggctctagtt gtcgacacct actatgatga tcaactcatt agctgtggca gcgtcaacag
agggacctgc cagcgacatg tctttcccca caatcatact gctgacatac agtcggaggt
tcactgcata ttctccccac agatagaaga gccccagtca tgtcctgact gtgtggtgag
cgccctggga gccaaagtcc tttcatctgt aaaggaccgg ttcatcaact tctttgtagg
caataccata aattcttctt atttcccaga tcatccattg cattcgatat cagtgagaag
gctaaaggaa acgaaagatg gttttatgtt tttgacggac cagtcctaca ttgatgtttt
acctgagttc agagattctt accccattaa gtatgtccat gcctttgaaa gcaacaattt
tatttacttc ttgacggtcc aaagggaaac tctagatgct cagacttttc acacaagaat
aatcaggttc tgttccataa actctggatt gcattcctac atggaaatgc ctctggagtg
tattctcaca gaaagagaa aaagagatc acaaagaag gaagtgttta atatacttca
ggctgcgtat gtcagcaagc ctgggcca gcttgctaga caaataggag ccagcctgaa
tgatgacatt cttttcgggg tgttcgcaca aagcaagcca gattctgccg aaccaatgga
tcgatctgcc atgtgtgcat tccctatcaa atatgtcaac gacttcttca caagatcgt
caacaaaaac aatgtgagat gtctccagca tttttacgga cccaatcatg agcactgctt
taataggaca cttctgagaa attcatcagg ctgtgaagcg cgccgtgatg aatatcgaac
agagttttacc acagctttgc agcgcgttga cttattcatg ggtcaattca gcgaagtcct
cttaacatct atatccacct tcattaaagg agacctcacc atagctaatc ttgggacatc
agagggtcgc ttcatgcagg ttgtggtttc tcgatcagga ccatcaaccc tcatgtgaa
ttttctcctg gactccatc cagtgtctcc agaagtgatt gtggagcata cattaaacca
aaatggctac acactggtta tcactgggaa gaagatcacg aagatcccat tgaatggctt
gggctgcaga catttccagt cctgcagtca atgcctctgc gccccacccc ttgttcagtg
tggctggtgc cacgacaaat gtgtgcgatc ggaggaatgc ctgagcggga catggactca
acagatctgt ctgcctgcaa tctacaaggt ttttccaaat agtgcacccc ttgaaggagg
gacaaggctg accatatgtg gctgggactt tggatttcgg aggaataata aatttgattt
aaagaaaact agagttctcc ttggaaatga gagctgcacc ttgacttaa gtgagagcac
gatgaataca ttgaaatgca cagttggtcc tgccatgaat aagcatttcc atatgtccat
aattatttca aatggccacg ggacaacaca atacagtaca ttctcctatg tggatcctgt
aataacaagt atttcgccga atacggtcc tatggctggt ggcacttttac ttactttaac
tggaaattac ctaaacagtg ggaattctag acacatttca attggtggaa aaacatgtac
tttaaaaagt gtgtcaaaca gtattcttga atgttataccc ccagcccaaa ccatttcaac
tgagtttgct gttaaattga aaattgactt agccaaccga gagacaagca tcttcagtta
```

-continued

| SEQUENCES |
|---|

```
ccgtgaagat cccattgtct atgaaattca tccaaccaaa tcttttatta gtggtgggag
cacaataaca ggtgttggga aaaacctgaa ttcagttagt gtcccgagaa tggtcataaa
tgtgcatgaa gcaggaagga actttacagt ggcatgtcaa catcgctcta attcagagat
aatctgttgt accactcctt ccctgcaaca gctgaatctg caactccccc tgaaaaccaa
agccttttc atgttagatg ggatcctttc caaatacttt gatctcattt atgtacataa
tcctgtgttt aagccttttg aaaagccagt gatgatctca atgggcaatg aaaatgtact
ggaaattaag ggaaatgata ttgaccctga agcagttaaa ggtgaagtgt taaaagttgg
aaataagagc tgtgagaata tacacttaca ttctgaagcc gttttatgca cggtccccaa
tgacctgctg aaattgaaca gcgagctaaa tatagagtgg aagcaagcaa tttcttcaac
cgtccttgga aaagtaatag ttcaaccaga tcagaatttc acaggattga ttgctggtgt
tgtctcaata tcaacagcac tgttattact acttgggttt ttcctgtggc tgaaaaagag
aaagcaaatt aaagatctgg gcagtgaatt agttcgctac gatgcaagag tacacactcc
tcatttggat aggcttgtaa gtgcccgaag tgtaagccca actacagaaa tggtttcaaa
tgaatctgta gactaccgag ctacttttcc agaagatcag tttcctaatt catctcagaa
cggttcatgc cgacaagtgc agtatcctct gacagacatg tcccccatcc taactagtgg
ggactctgat atatccagtc cattactgca aaatactgtc cacattgacc tcagtgctct
aaatccagag ctggtccagg cagtgcagca tgtagtgatt gggcccagta gcctgattgt
gcatttcaat gaagtcatag gaagagggca ttttggttgt gtatatcatg ggactttgtt
ggacaatgat ggcaagaaaa ttcactgtgc tgtgaaatcc ttgaacagaa tcactgacat
aggagaagtt tcccaatttc tgaccgaggg aatcatcatg aaagatttta gtcatcccaa
tgtcctctcg ctcctgggaa tctgcctgcg aagtgaaggg tctccgctgg tggtcctacc
atacatgaaa catggagatc ttcgaaattt cattcgaaat gagactcata atccaactgt
aaaagatctt attggctttg gtcttcaagt agccaaaggc atgaaatatc ttgcaagcaa
aaagtttgtc cacagagact tggctgcaag aaactgtatg ctggatgaaa aattcacagt
caaggttgct gattttggtc ttgccagaga catgtatgat aaagaatact atagtgtaca
caacaaaaca ggtgcaaagc tgccagtgaa gtggatggct ttggaaagtc tgcaaactca
aaagtttacc accaagtcag atgtgtggtc ctttggcgtg ctcctctggg agctgatgac
aagaggagcc ccaccttatc ctgacgtaaa caccttgat ataactgttt acttgttgca
agggagaaga ctcctacaac ccgaatactg cccagacccc ttatatgaag taatgctaaa
atgctggcac cctaaagccg aaatgcgccc atcctttct gaactggtgt cccggatatc
agcgatcttc tctactttca ttggggagca ctatgtccat gtgaacgcta cttatgtgaa
cgtaaaatgt gtcgctccgt atccttctct gttgtcatca gaagataacg ctgatgatga
ggtggacaca cgaccagcct ccttctggga gacatcatag tgctagtact atgtcaaagc
aacagtccac actttgtcca atggtttttt cactgcctga cctttaaaag gccatcgata
ttctttgctc ttgccaaaat tgcactatta taggacttgt attgttattt aaattactgg
attctaagga atttcttatc tgacagagca tcagaaccag aggcttggtc ccacaggcca
cggaccaatg gcctgcagcc gtgacaacac tcctgtcata ttggagtcca aaacttgaat
tctgggttga atttttttaaa aatcaggtac cacttgattt catatgggaa attgaagcag
gaaatattga gggcttcttg atcacagaaa actcagaaga gatagtaatg ctcaggacag
gagcggcagc cccagaacag gccactcatt tagaattcta gtgtttcaaa acacttttgt
gtgttgtatg gtcaataaca ttttcatta ctgatggtgt cattcaccca ttaggtaaac
attcccttt aaatgtttgt ttgttttttg agacaggatc tcactctgtt gccagggctg
tagtgcagtg gtgtgatcat agctcactgc aacctccacc tcccaggctc aagcctcccg
aatagctggg actacaggcg cacaccacca tccccggcta attttttgtat tttttgtaga
gacggggttt tgccatgttg ccaaggctgg tttcaaactc ctggactcaa gaaatccacc
cacctcagcc tcccaaagtg ctaggattac aggcatgagc cactgcgccc agcccttata
aattttgta tagacattcc tttggttgga agaatattta taggcaatac agtcaaagtt
tcaaaatagc atcacacaaa acatgtttat aaatgaacag gatgtaatgt acatagatga
cattaagaaa atttgtatga aataatttag tcatcatgaa atatttagtt gtcatataaa
aacccactgt ttgagaatga tgctactctg atctaatgaa tgtgaacatg tagatgtttt
gtgtgtattt ttttaaatga aaactcaaaa taagacaagt aatttgttga taaatatttt
taaagataac tcagcatgtt tgtaaagcag gatacatttt actaaaaggt tcattggttc
caatcacagc tcataggtag agcaaagaaa gggtggatgg attgaaaaga ttagcctctg
tctcggtggc aggttccac ctcgcaagca attggaaaca aaacttttgg ggagttttat
tttgcattag ggtgtgtttt atgttaagca aaacatactt tagaaacaaa tgaaaaggc
aattgaaaat cccagctatt tcacctagat ggaatagcca ccctgagcag aactttgtga
tgcttcattc tgtggaattt tgtgcttgct actgtatagt gcatgggtg taggttactc
taactggttt tgtcgacgta aacatttaaa gtgttatatt ttttataaaa atgttttt
ttaatgatat gagaaaaatt ttgttaggcc acaaaaacac tgcactgtga acatttaga
aaaggtatgt cagactggga ttaatgacag catgattttc aatgactgta aattgcgata
aggaaatgta ctgattgcca atacaccccca ccctcattac atcatcagga cttgaagcca
agggttaacc cagcaagcta caaagagggt gtgtcacact gaaactcaat agttgagttt
ggctgttgtt gcaggaaaat gattataact aaaagctctc tgatagtgca gagacttacc
agaagacaca aggaattgta ctgaagagct attacaatcc aaatattgcc gtttcataaa
tgtaataagt aatactaatt acagagtat tgtaaatggt ggatgacaaa agaaaatctg
ctctgtggaa agaaagaact gtctctacca gggtcaagag catgaacgca tcaatagaaa
gaactcgggg aaacatccca tcaacaggac tacacacttg tatatacatt cttgagaaca
ctgcaatgtg aaaatcacgt ttgctattta taaacttgtc cttagattaa tgtgtctgga
cagattgtgg gagtaagtga ttcttctaag aattagatac ttgtcactgc ctatacctgc
agctgaactg aatggtactt cgtatgttaa tagttgttct gataaatcat gcaattaaag
taaagtgatg caacatcttg taaaaaaaaa aaaaaaaaa a
```

We claim:

1. A method for inhibiting osteolysis or treating osteoporosis in a subject in need thereof, the method comprising administering to the subject a composition comprising an effective amount of at least one Recepteur d'Origine Nantais (RON) inhibitor selected from the group consisting of OSI-296 and ASLAN002.

2. The method of claim 1, wherein the subject has been diagnosed with a condition selected from the group consisting of inflammation, cyst, and cancer.

3. The method of claim 2, wherein the subject has been diagnosed with cancer with bone metastasis or cancer-mediated bone destruction.

4. The method of claim 2, wherein the cancer is selected from the group consisting of lymphoma, lung cancer, pancreatic cancer, breast cancer, rectal cancer, colon cancer, stomach cancer, larynx cancer, liver cancer, brain cancer, and skin cancer.

5. The method of claim 1, wherein the osteolysis is caused by a condition selected from the group consisting of tumor, inflammation, and cyst.

6. The method of claim 5, wherein the condition comprises a bone tumor or a tumor located in bone.

7. The method of claim 1, wherein the subject is pre-menopausal.

8. The method of claim 1, wherein the subject is menopausal.

9. The method of claim 1, wherein the subject is post-menopausal.

10. The method of claim 1, wherein the RON inhibitor does not depend on the function of RANKL or TGFβ.

* * * * *

SEQUENCE LISTING

<160> NUMBER OF SEQ ID NOS: 4

<210> SEQ ID NO 1
<211> LENGTH: 1351
<212> TYPE: PRT
<213> ORGANISM: Homo sapiens

<400> SEQUENCE: 1

```
Met Glu Leu Leu Pro Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
                20                  25                  30

Pro Tyr Ala Ala Ser Arg Asp Phe Asp Val Lys Tyr Val Val Pro Ser
                35                  40                  45

Phe Ser Ala Gly Gly Leu Val Gln Ala Met Val Thr Tyr Glu Gly Asp
        50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
                100                 105                 110

Gly Pro Pro Gly Asp Thr Asp Thr Lys Val Leu Val Leu Asp Pro Ala
                115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
                180                 185                 190

Gln Ala Ser Tyr Phe Tyr Val Ala Ser Ser Leu Asp Ala Ala Val Ala
                195                 200                 205

Ala Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
                260                 265                 270

Pro Ser Ala Leu His Thr Arg Leu Ala Arg Leu Ser Ala Thr Glu Pro
                275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
                340                 345                 350

Gly Lys Asp Gly Gly Pro Gly Val Gly Pro Asn Ser Val Val Cys Ala
                355                 360                 365
```

-continued

```
Phe Pro Ile Asp Leu Leu Asp Thr Leu Ile Asp Glu Gly Val Glu Arg
        370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Gln Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
```

-continued

```
            785                 790                 795                 800
        Leu Ser Phe His Asp Gly Leu Arg Ala Val Glu Ser Arg Cys Glu Arg
                        805                 810                 815
        Gln Leu Pro Glu Gln Gln Leu Cys Arg Leu Pro Glu Tyr Val Val Arg
                        820                 825                 830
        Asp Pro Gln Gly Trp Val Ala Gly Asn Leu Ser Ala Arg Gly Asp Gly
                        835                 840                 845
        Ala Ala Gly Phe Thr Leu Pro Gly Phe Arg Phe Leu Pro Pro His
                        850                 855                 860
        Pro Pro Ser Ala Asn Leu Val Pro Leu Lys Pro Glu Glu His Ala Ile
        865                 870                 875                 880
        Lys Phe Glu Val Cys Val Asp Gly Glu Cys His Ile Leu Gly Arg Val
                        885                 890                 895
        Val Arg Pro Gly Pro Asp Gly Val Pro Gln Ser Thr Leu Leu Gly Ile
                        900                 905                 910
        Leu Leu Pro Leu Leu Leu Val Ala Ala Leu Ala Thr Ala Leu Val
                        915                 920                 925
        Phe Ser Tyr Trp Trp Arg Arg Lys Gln Leu Val Leu Pro Pro Asn Leu
                        930                 935                 940
        Asn Asp Leu Ala Ser Leu Asp Gln Thr Ala Gly Ala Thr Pro Leu Pro
        945                 950                 955                 960
        Ile Leu Tyr Ser Gly Ser Asp Tyr Arg Ser Gly Leu Ala Leu Pro Ala
                        965                 970                 975
        Ile Asp Gly Leu Asp Ser Thr Thr Cys Val His Gly Ala Ser Phe Ser
                        980                 985                 990
        Asp Ser Glu Asp Glu Ser Cys Val Pro Leu Leu Arg Lys Glu Ser Ile
                    995                 1000                1005
        Gln Leu Arg Asp Leu Asp Ser Ala Leu Leu Ala Glu Val Lys Asp
                    1010                1015                1020
        Val Leu Ile Pro His Glu Arg Val Val Thr His Ser Asp Arg Val
                    1025                1030                1035
        Ile Gly Lys Gly His Phe Gly Val Val Tyr His Gly Glu Tyr Ile
                    1040                1045                1050
        Asp Gln Ala Gln Asn Arg Ile Gln Cys Ala Ile Lys Ser Leu Ser
                    1055                1060                1065
        Arg Ile Thr Glu Met Gln Gln Val Glu Ala Phe Leu Arg Glu Gly
                    1070                1075                1080
        Leu Leu Met Arg Gly Leu Asn His Pro Asn Val Leu Ala Leu Ile
                    1085                1090                1095
        Gly Ile Met Leu Pro Pro Glu Gly Leu Pro His Val Leu Leu Pro
                    1100                1105                1110
        Tyr Met Cys His Gly Asp Leu Leu Gln Phe Ile Arg Ser Pro Gln
                    1115                1120                1125
        Arg Asn Pro Thr Val Lys Asp Leu Ile Ser Phe Gly Leu Gln Val
                    1130                1135                1140
        Ala Arg Gly Met Glu Tyr Leu Ala Glu Gln Lys Phe Val His Arg
                    1145                1150                1155
        Asp Leu Ala Ala Arg Asn Cys Met Leu Asp Glu Ser Phe Thr Val
                    1160                1165                1170
        Lys Val Ala Asp Phe Gly Leu Ala Arg Asp Ile Leu Asp Arg Glu
                    1175                1180                1185
        Tyr Tyr Ser Val Gln Gln His Arg His Ala Arg Leu Pro Val Lys
                    1190                1195                1200
```

| Trp | Met | Ala | Leu | Glu | Ser | Leu | Gln | Thr | Tyr | Arg | Phe | Thr | Thr | Lys |
| | 1205 | | | | 1210 | | | | | 1215 | | | | |

| Ser | Asp | Val | Trp | Ser | Phe | Gly | Val | Leu | Trp | Glu | Leu | Leu | Thr |
| 1220 | | | | | 1225 | | | | 1230 | | | | |

| Arg | Gly | Ala | Pro | Pro | Tyr | Arg | His | Ile | Asp | Pro | Phe | Asp | Leu | Thr |
| 1235 | | | | | 1240 | | | | | 1245 | | | | |

| His | Phe | Leu | Ala | Gln | Gly | Arg | Arg | Leu | Pro | Gln | Pro | Glu | Tyr | Cys |
| 1250 | | | | | 1255 | | | | | 1260 | | | | |

| Pro | Asp | Ser | Leu | Tyr | Gln | Val | Met | Gln | Gln | Cys | Trp | Glu | Ala | Asp |
| 1265 | | | | | 1270 | | | | | 1275 | | | | |

| Pro | Ala | Val | Arg | Pro | Thr | Phe | Arg | Val | Leu | Val | Gly | Glu | Val | Glu |
| 1280 | | | | | 1285 | | | | | 1290 | | | | |

| Gln | Ile | Val | Ser | Ala | Leu | Leu | Gly | Asp | His | Tyr | Val | Gln | Leu | Pro |
| 1295 | | | | | 1300 | | | | | 1305 | | | | |

| Ala | Thr | Tyr | Met | Asn | Leu | Gly | Pro | Ser | Thr | Ser | His | Glu | Met | Asn |
| 1310 | | | | | 1315 | | | | | 1320 | | | | |

| Val | Arg | Pro | Glu | Gln | Pro | Gln | Phe | Ser | Pro | Met | Pro | Gly | Asn | Val |
| 1325 | | | | | 1330 | | | | | 1335 | | | | |

| Arg | Arg | Pro | Arg | Pro | Leu | Ser | Glu | Pro | Pro | Arg | Pro | Thr |
| 1340 | | | | | 1345 | | | | | 1350 | | |

<210> SEQ ID NO 2
<211> LENGTH: 4638
<212> TYPE: DNA
<213> ORGANISM: Homo sapiens

<400> SEQUENCE: 2

```
agtgtacagc ggcggctggg gcggcaggtg aggcggctgg ggcgttgctg tcgtgcgtcc        60
gcaggcgtca ggtgctcaga cccgagggcc gggaagggat ttgggtttca caggaacctg       120
gggcggggt ccgctatctt ggggctgtcg ggaccgctgc ttaaatttgg cccagtccag        180
acctcgagtc gggcccccag ccaggcccac gcccaggtcc aggcccaggc cggtagggat       240
cctctagggt cccagctcgc ctcgatggag ctcctcccgc cgctgcctca gtccttcctg       300
ttgctgctgc tgttgcctgc caagcccgcg gcgggcgagg actggcagtg cccgcgcacc       360
ccctacgcgg cctctcgcga cttttgacgtg aagtacgtgg tgcccagctt ctccgccgga       420
ggcctggtac aggccatggt gacctacgag ggcgacagaa atgagagtgc tgtgtttgta       480
gccatacgca atcgcctgca tgtgcttggg cctgacctga agtctgtcca gagcctggcc       540
acgggccctg ctggagaccc tggctgccag acgtgtgcag cctgtggccc aggaccccac       600
ggccctcccg gtgacacaga cacaaaggtg ctggtgctgg atcccgcgct gctgcgctg        660
gtcagttgtg gctccagcct gcagggccgc tgcttcctgc atgacctaga gccccaaggg       720
acagccgtgc atctggcagc gccagcctgc ctcttctcag cccaccataa ccggcccgat       780
gactgccccg actgtgtggc cagcccattg gcaccccgtg taactgtggt tgagcaaggc       840
caggcctcct atttctacgt ggcatcctca ctggacgcag ccgtggctgc cagcttcagc       900
ccacgctcag tgtctatcag gcgtctcaag gctgacgcct cgggattcgc accgggcttt       960
gtggcgttgt cagtgctgcc caagcatctt gtctcctaca gtattgaata cgtgcacagc      1020
ttccacacgg gagccttcgt atacttcctg actgtacagc cggccagcgt gacagatgat      1080
cctagtgccc tgcacacacg cctggcacgg cttagcgcca ctgagccaga gttgggtgac      1140
tatcgggagc tggtcctcga ctgcagattt gctccaaaaac gcaggcgccg ggggccccca      1200
```

```
gaaggcggac agccctaccc tgtgctgcgg gtggcccact ccgctccagt gggtgcccaa    1260
cttgccactg agctgagcat cgccgagggc caggaagtac tatttggggt ctttgtgact    1320
ggcaaggatg gtggtcctgg cgtgggcccc aactctgtcg tctgtgcctt ccccattgac    1380
ctgctggaca cactaattga tgagggtgtg gagcgctgtt gtgaatcccc agtccatcca    1440
ggcctccggc gaggcctcga cttcttccag tcgcccagtt tttgccccaa cccgcctggc    1500
ctggaagccc tcagcccaa caccagctgc cgccacttcc ctctgctggt cagtagcagc    1560
ttctcacgtg tggacctatt caatgggctg ttgggaccag tacaggtcac tgcattgtat    1620
gtgacacgcc ttgacaacgt cacagtggca cacatgggca caatggatgg gcgtatcctg    1680
caggtggagc tggtcaggtc actaaactac ttgctgtatg tgtccaactt ctcactgggt    1740
gacagtgggg agcccgtgca gcgggatgtc agtcgtcttg ggaccaccct actctttgcc    1800
tctggggacc aggttttcca ggtacctatc caaggccctg gctgccgcca cttcctgacc    1860
tgtgggcgtt gcctaagggc atggcatttc atgggctgtg gctggtgtgg gaacatgtgc    1920
ggccagcaga aggagtgtcc tggctcctgg caacaggacc actgcccacc taagcttact    1980
gagttccacc cccacagtgg acctctaagg ggcagtacaa ggctgaccct gtgtggctcc    2040
aacttctacc ttcaccccttc tggtctggtg cctgagggaa cccatcaggt cactgtgggc    2100
caaagtccct gccggccact gcccaaggac agctcaaaac tcagaccagt gccccggaaa    2160
gactttgtag aggagtttga gtgtgaactg gagcccttgg gcacccaggc agtggggcct    2220
accaacgtca gcctcaccgt gactaacatg ccaccgggca agcacttccg ggtagacggc    2280
acctccgtgc tgagaggctt ctctttcatg gagccagtgc tgatagcagt gcaacccctc    2340
tttggcccac gggcaggagg cacctgtctc actcttgaag gccagagtct gtctgtaggc    2400
accagccggg ctgtgctggt caatgggact gagtgtctgc tagcacgggt cagtgagggg    2460 cagctttat gtgccacacc ccctggggcc acggtggcca gtgtcccccct tagcctgcag    2520 gtgggggggtg cccaggtacc tggttcctgg accttccagt acagagaaga ccctgtcgtg    2580
ctaagcatca gccccaactg tggctacatc aactcccaca tcaccatctg tggccagcat    2640
ctaacttcag catggcactt agtgctgtca ttccatgacg ggcttagggc agtggaaagc    2700
aggtgtgaga ggcagcttcc agagcagcag ctgtgccgcc ttcctgaata tgtggtccga    2760 gaccccagg gatgggtggc agggaatctg agtgcccgag gggatggagc tgctggcttt    2820
acactgcctg gctttcgctt cctacccca ccccatccac ccagtgccaa cctagttcca    2880
ctgaagcctg aggagcatgc cattaagttt gaggtctgcg tagatggtga atgtcatatc    2940
ctgggtagag tggtgcggcc agggccagat ggggtcccac agagcacgct ccttggtatc    3000
ctgctgcctt tgctgctgct tgtggctgca ctggcgactg cactggtctt cagctactgg    3060
tggcggagga agcagctagt tcttcctccc aacctgaatg acctggcatc cctggaccag    3120
actgctggag ccacacccct gcctattctg tactcgggct ctgactacag aagtggcctt    3180
gcactccctg ccattgatgg tctggattcc accacttgtg tccatggagc atccttctcc    3240
gatagtgaag atgaatcctg tgtgccactg ctgcggaaag agtccatcca gctaagggac    3300
ctggactctg cgctcttggc tgaggtcaag gatgtgctga ttcccatga gcgggtggtc    3360 acccacagtg accgagtcat tggcaaaggc cactttggag ttgtctacca cggagaatac    3420
atagaccagg cccagaatcg aatccaatgt gccatcaagt cactaagtcg catcacagag    3480
atgcagcagg tggaggcctt cctgcgagag gggctgctca tgcgtggcct gaaccacccg    3540
aatgtgctgg ctctcattgg tatcatgttg ccacctgagg gcctgcccca tgtgctgctg    3600
```

-continued

```
ccctatatgt gccacggtga cctgctccag ttcatccgct cacctcagcg gaaccccacc   3660
gtgaaggacc tcatcagctt tggcctgcag gtagcccgcg gcatggagta cctggcagag   3720
cagaagtttg tgcacaggga cctggctgcg cggaactgca tgctggacga gtcattcaca   3780
gtcaaggtgg ctgactttgg tttggcccgc gacatcctgg acagggagta ctatagtgtt   3840
caacagcatc gccacgctcg cctacctgtg aagtggatgg cgctggagag cctgcagacc   3900
tatagattta ccaccaagtc tgatgtgtgg tcatttggtg tgctgctgtg ggaactgctg   3960
acacggggtg ccccaccata ccgccacatt gaccctttg accttaccca cttcctggcc   4020
cagggtcggc gcctgcccca gcctgagtat tgccctgatt ctctgtacca agtgatgcag   4080
caatgctggg aggcagaccc agcagtgcga cccaccttca gagtactagt ggggaggtg   4140 gagcagatag tgtctgcact gcttggggac cattatgtgc agctgccagc aacctacatg   4200
aacttgggcc ccagcacctc gcatgagatg aatgtgcgtc cagaacagcc gcagttctca   4260
cccatgccag gaatgtacg ccggcccgg ccactctcag agcctcctcg gcccacttga   4320
cttagttctt gggctggacc tgcttagctg ccttgagcta accccaagct gcctctgggc   4380
catgccaggc cagagggcag tggccctcca ccttgttcct gccctttaac tttcagaggc   4440
aataggtaaa tggggcccat taggtccctc actccacaga gtgagccagt gagggcagtc   4500
ctgcaacatg tatttatgga gtgcctgctg tggaccctgt cttctgggca cagtggactc   4560
agcagtgacc acaccaacac tgacccttga accaataaag gaacaaatga ctattaaagc   4620
acaaaaaaaa aaaaaaaa                                                 4638

<210> SEQ ID NO 3
<211> LENGTH: 1390
<212> TYPE: PRT
<213> ORGANISM: Homo sapiens

<400> SEQUENCE: 3

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
```

```
                180             185             190
Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
        210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605
```

```
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
        675                 680                 685
His Ile Ser Ile Gly Gly Lys Thr Cys Thr Leu Lys Ser Val Ser Asn
    690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu Asn
        755                 760                 765
Ser Val Ser Val Pro Arg Met Val Ile Asn Val His Glu Ala Gly Arg
770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
            820                 825                 830
Leu Ile Tyr Val His Asn Pro Val Phe Lys Pro Phe Glu Lys Pro Val
        835                 840                 845
Met Ile Ser Met Gly Asn Glu Asn Val Leu Glu Ile Lys Gly Asn Asp
    850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
            900                 905                 910
Gln Ala Ile Ser Ser Thr Val Leu Gly Lys Val Ile Val Gln Pro Asp
        915                 920                 925
Gln Asn Phe Thr Gly Leu Ile Ala Gly Val Val Ser Ile Ser Thr Ala
    930                 935                 940
Leu Leu Leu Leu Leu Gly Phe Phe Leu Trp Leu Lys Lys Arg Lys Gln
945                 950                 955                 960
Ile Lys Asp Leu Gly Ser Glu Leu Val Arg Tyr Asp Ala Arg Val His
                965                 970                 975
Thr Pro His Leu Asp Arg Leu Val Ser Ala Arg Ser Val Ser Pro Thr
            980                 985                 990
Thr Glu Met Val Ser Asn Glu Ser  Val Asp Tyr Arg Ala  Thr Phe Pro
        995                 1000                1005
Glu Asp Gln Phe Pro Asn Ser  Ser Gln Asn Gly Ser  Cys Arg Gln
    1010                1015                1020
```

Val Gln Tyr Pro Leu Thr Asp Met Ser Pro Ile Leu Thr Ser Gly
1025                1030                1035

Asp Ser Asp Ile Ser Ser Pro Leu Leu Gln Asn Thr Val His Ile
1040                1045                1050

Asp Leu Ser Ala Leu Asn Pro Glu Leu Val Gln Ala Val Gln His
1055                1060                1065

Val Val Ile Gly Pro Ser Ser Leu Ile Val His Phe Asn Glu Val
1070                1075                1080

Ile Gly Arg Gly His Phe Gly Cys Val Tyr His Gly Thr Leu Leu
1085                1090                1095

Asp Asn Asp Gly Lys Lys Ile His Cys Ala Val Lys Ser Leu Asn
1100                1105                1110

Arg Ile Thr Asp Ile Gly Glu Val Ser Gln Phe Leu Thr Glu Gly
1115                1120                1125

Ile Ile Met Lys Asp Phe Ser His Pro Asn Val Leu Ser Leu Leu
1130                1135                1140

Gly Ile Cys Leu Arg Ser Glu Gly Ser Pro Leu Val Val Leu Pro
1145                1150                1155

Tyr Met Lys His Gly Asp Leu Arg Asn Phe Ile Arg Asn Glu Thr
1160                1165                1170

His Asn Pro Thr Val Lys Asp Leu Ile Gly Phe Gly Leu Gln Val
1175                1180                1185

Ala Lys Gly Met Lys Tyr Leu Ala Ser Lys Lys Phe Val His Arg
1190                1195                1200

Asp Leu Ala Ala Arg Asn Cys Met Leu Asp Glu Lys Phe Thr Val
1205                1210                1215

Lys Val Ala Asp Phe Gly Leu Ala Arg Asp Met Tyr Asp Lys Glu
1220                1225                1230

Tyr Tyr Ser Val His Asn Lys Thr Gly Ala Lys Leu Pro Val Lys
1235                1240                1245

Trp Met Ala Leu Glu Ser Leu Gln Thr Gln Lys Phe Thr Thr Lys
1250                1255                1260

Ser Asp Val Trp Ser Phe Gly Val Leu Leu Trp Glu Leu Met Thr
1265                1270                1275

Arg Gly Ala Pro Pro Tyr Pro Asp Val Asn Thr Phe Asp Ile Thr
1280                1285                1290

Val Tyr Leu Leu Gln Gly Arg Arg Leu Leu Gln Pro Glu Tyr Cys
1295                1300                1305

Pro Asp Pro Leu Tyr Glu Val Met Leu Lys Cys Trp His Pro Lys
1310                1315                1320

Ala Glu Met Arg Pro Ser Phe Ser Glu Leu Val Ser Arg Ile Ser
1325                1330                1335

Ala Ile Phe Ser Thr Phe Ile Gly Glu His Tyr Val His Val Asn
1340                1345                1350

Ala Thr Tyr Val Asn Val Lys Cys Val Ala Pro Tyr Pro Ser Leu
1355                1360                1365

Leu Ser Ser Glu Asp Asn Ala Asp Asp Glu Val Asp Thr Arg Pro
1370                1375                1380

Ala Ser Phe Trp Glu Thr Ser
1385                1390

<210> SEQ ID NO 4
<211> LENGTH: 6641
<212> TYPE: DNA

<213> ORGANISM: Homo sapiens

<400> SEQUENCE: 4

```
gccctcgccg cccgcggcgc cccgagcgct tgtgagcag atgcggagcc gagtggaggg    60
cgcgagccag atgcggggcg acagctgact tgctgagagg aggcggggag gcgcggagcg   120
cgcgtgtggt ccttgcgccg ctgacttctc cactggttcc tgggcaccga aagataaacc   180
tctcataatg aaggcccccg ctgtgcttgc acctggcatc ctcgtgctcc tgtttacctt   240
ggtgcagagg agcaatgggg agtgtaaaga ggcactagca aagtccgaga tgaatgtgaa   300
tatgaagtat cagcttccca acttcaccgc ggaaacaccc atccagaatg tcattctaca   360
tgagcatcac attttccttg gtgccactaa ctacattat gttttaaatg aggaagacct   420
tcagaaggtt gctgagtaca agactgggcc tgtgctggaa cacccagatt gtttcccatg   480
tcaggactgc agcagcaaag ccaatttatc aggaggtgtt tggaaagata acatcaacat   540
ggctctagtt gtcgacacct actatgatga tcaactcatt agctgtggca gcgtcaacag   600
agggacctgc cagcgacatg tctttcccca aatcatact gctgacatac agtcggaggt   660
tcactgcata ttctccccac agatagaaga gcccagccag tgtcctgact gtgtggtgag   720
cgccctggga gccaaagtcc tttcatctgt aaaggaccgg ttcatcaact tctttgtagg   780
caataccata aattcttctt atttcccaga tcatccattg cattcgatat cagtgagaag   840
gctaaaggaa acgaaagatg gttttatgtt tttgacggac cagtcctaca ttgatgtttt   900
acctgagttc agagattctt acccccattaa gtatgtccat gcctttgaaa gcaacaattt   960
tatttacttc ttgacggtcc aaagggaaac tctagatgct cagacttttc acacaagaat  1020
aatcaggttc tgttccataa actctggatt gcattcctac atggaaatgc ctctggagtg  1080
tattctcaca gaaaagagaa aaagagatc cacaaagaag gaagtgttta atatacttca  1140
ggctgcgtat gtcagcaagc ctggggccca gcttgctaga caaataggag ccagcctgaa  1200
tgatgacatt cttttcgggg tgttcgcaca aagcaagcca gattctgccg aaccaatgga  1260
tcgatctgcc atgtgtgcat tccctatcaa atatgtcaac gacttcttca caagatcgt  1320
caacaaaaac aatgtgagat gtctccagca tttttacgga cccaatcatg agcactgctt  1380
taataggaca cttctgagaa attcatcagg ctgtgaagcg cgccgtgatg aatatcgaac  1440
agagtttacc acagctttgc agcgcgttga cttattcatg ggtcaattca gcgaagtcct  1500
cttaacatct atatccacct tcattaaagg agacctcacc atagctaatc ttgggacatc  1560
agagggtcgc ttcatgcagg ttgtggtttc tcgatcagga ccatcaaccc ctcatgtgaa  1620
ttttctcctg gactccatcc agtgtctcc agaagtgatt gtggagcata cattaaacca  1680
aaatggctac acactggtta tcactgggaa gaagatcacg aagatcccat gaatggctt   1740
gggctgcaga catttccagt cctgcagtca atgcctctct gccccaccct tgttcagtg   1800
tggctggtgc cacgacaaat gtgtgcgatc ggaggaatgc ctgagcggga catggactca  1860
acagatctgt ctgcctgcaa tctacaaggt tttcccaaat agtgcacccc ttgaaggagg  1920
gacaaggctg accatatgtg gctgggactt tggatttcgg aggaataata aatttgattt  1980
aaagaaaact agagttctcc ttggaaatga gagctgcacc ttgactttaa gtgagagcac  2040
gatgaataca ttgaaatgca cagttggtcc tgccatgaat aagcatttca atatgtccat  2100
aattatttca aatggccacg ggacaacaca atacagtaca ttctcctatg tggatcctgt  2160
aataacaagt atttcgccga atacggtcc tatggctggt ggcactttac ttactttaac  2220
tggaaattac ctaaacagtg ggaattctag acacatttca attggtggaa aaacatgtac  2280
```

```
tttaaaaagt gtgtcaaaca gtattcttga atgttatacc ccagcccaaa ccatttcaac      2340
tgagtttgct gttaaattga aaattgactt agccaaccga gagacaagca tcttcagtta      2400
ccgtgaagat cccattgtct atgaaattca tccaaccaaa tcttttatta gtggtgggag      2460
cacaataaca ggtgttggga aaaacctgaa ttcagttagt gtcccgagaa tggtcataaa      2520
tgtgcatgaa gcaggaagga actttacagt ggcatgtcaa catcgctcta attcagagat      2580
aatctgttgt accactcctt ccctgcaaca gctgaatctg caactccccc tgaaaaccaa      2640 agccttttc atgttagatg ggatcctttc caaatacttt gatctcattt atgtacataa       2700
tcctgtgttt aagccttttg aaaagccagt gatgatctca atgggcaatg aaaatgtact      2760
ggaaattaag ggaaatgata ttgaccctga agcagttaaa ggtgaagtgt aaaagttgg       2820 aaataagagc tgtgagaata tacacttaca ttctgaagcc gttttatgca cggtccccaa      2880
tgacctgctg aaattgaaca gcgagctaaa tatagagtgg aagcaagcaa tttcttcaac     2940
cgtccttgga aaagtaatag ttcaaccaga tcagaatttc acaggattga ttgctggtgt     3000
tgtctcaata tcaacagcac tgttattact acttgggttt ttcctgtggc tgaaaaagag     3060
aaagcaaatt aaagatctgg gcagtgaatt agttcgctac gatgcaagag tacacactcc    3120
tcatttggat aggcttgtaa gtgcccgaag tgtaagccca actacagaaa tggtttcaaa    3180
tgaatctgta gactaccgag ctacttttcc agaagatcag tttcctaatt catctcagaa    3240
cggttcatgc cgacaagtgc agtatcctct gacagacatg tcccccatcc taactagtgg    3300
ggactctgat atatccagtc cattactgca aaatactgtc cacattgacc tcagtgctct    3360
aaatccagag ctggtccagg cagtgcagca tgtagtgatt gggcccagta gcctgattgt    3420
gcatttcaat gaagtcatag gaagagggca ttttggttgt gtatatcatg ggactttgtt    3480
ggacaatgat ggcaagaaaa ttcactgtgc tgtgaaatcc ttgaacagaa tcactgacat    3540
aggagaagtt tcccaatttc tgaccgaggg aatcatcatg aaagatttta gtcatcccaa    3600
tgtcctctcg ctcctgggaa tctgcctgcg aagtgaaggg tctccgctgg tggtcctacc    3660
atacatgaaa catggagatc ttcgaaattt cattcgaaat gagactcata atccaactgt    3720
aaaagatctt attggctttg tcttcaagt agccaaaggc atgaaatatc ttgcaagcaa     3780
aaagtttgtc cacagagact tggctgcaag aaactgtatg ctggatgaaa aattcacagt     3840
caaggttgct gattttggtc ttgccagaga catgtatgat aaagaatact atagtgtaca     3900
caacaaaaca ggtgcaaagc tgccagtgaa gtggatggct ttggaaagtc tgcaaactca     3960
aaagtttacc accaagtcag atgtgtggtc ctttggcgtg ctcctctggg agctgatgac     4020
aagaggagcc ccaccttatc ctgacgtaaa cacctttgat ataactgttt acttgttgca     4080
agggagaaga ctcctacaac ccgaatactg cccagacccc ttatatgaag taatgctaaa     4140
atgctggcac cctaaagccg aaatgcgccc atccttttct gaactggtgt cccggatatc     4200
agcgatcttc tctactttca ttggggagca ctatgtccat gtgaacgcta cttatgtgaa     4260
cgtaaaatgt gtcgctccgt atccttctct gttgtcatca aagataacg ctgatgatga      4320 ggtggacaca cgaccagcct ccttctggga gacatcatag tgctagtact atgtcaaagc     4380
aacagtccac actttgtcca atggttttt cactgcctga cctttaaaag gccatcgata      4440
ttctttgctc ttgccaaaat tgcactatta taggacttgt attgttattt aaattactgg     4500
attctaagga atttccttatc tgacagagca tcagaaccag aggcttggtc ccacaggcca    4560
cggaccaatg gcctgcagcc gtgacaacac tcctgtcata ttggagtcca aaacttgaat    4620
```

```
tctgggttga attttttaaa aatcaggtac cacttgattt catatgggaa attgaagcag    4680
gaaatattga gggcttcttg atcacagaaa actcagaaga gatagtaatg ctcaggacag    4740
gagcggcagc cccagaacag gccactcatt tagaattcta gtgtttcaaa acacttttgt    4800
gtgttgtatg gtcaataaca tttttcatta ctgatggtgt cattcaccca ttaggtaaac    4860 attcccttttt aaatgtttgt ttgtttttttg agacaggatc tcactctgtt gccagggctg  4920
tagtgcagtg gtgtgatcat agctcactgc aacctccacc tcccaggctc aagcctcccg    4980
aatagctggg actacaggcg cacaccacca tcccCggcta atttttgtat tttttgtaga    5040
gacggggttt tgccatgttg ccaaggctgg tttcaaactc ctggactcaa gaatccacc     5100 cacctcagcc tcccaaagtg ctaggattac aggcatgagc cactgcgccc agcccttata    5160 aattttttgta tagacattcc tttggttgga agaatattta taggcaatac agtcaaagtt    5220
tcaaaatagc atcacacaaa acatgtttat aaatgaacag gatgtaatgt acatagatga    5280
cattaagaaa atttgtatga aataatttag tcatcatgaa atatttagtt gtcatataaa    5340
aacccactgt ttgagaatga tgctactctg atctaatgaa tgtgaacatg tagatgtttt    5400
gtgtgtattt ttttaaatga aaactcaaaa taagacaagt aatttgttga taaatatttt    5460
taaagataac tcagcatgtt tgtaaagcag gatacatttt actaaaaggt tcattggttc    5520
caatcacagc tcataggtag agcaaagaaa gggtggatgg attgaaaaga ttagcctctg    5580
tctcggtggc aggttcccac ctcgcaagca attggaaaca aaacttttgg ggagttttat    5640
tttgcattag ggtgtgtttt atgttaagca aaacatactt tagaaacaaa tgaaaaaggc    5700
aattgaaaat cccagctatt tcacctagat ggaatagcca ccctgagcag aactttgtga    5760
tgcttcattc tgtggaattt tgtgcttgct actgtatagt gcatgtggtg taggttactc    5820
taactggttt tgtcgacgta aacatttaaa gtgttatatt ttttataaaa atgtttattt    5880
ttaatgatat gagaaaaatt tgttaggcc acaaaaacac tgcactgtga acattttaga    5940
aaaggtatgt cagactggga ttaatgacag catgattttc aatgactgta aattgcgata    6000
aggaaatgta ctgattgcca atacaccca ccctcattac atcatcagga cttgaagcca    6060
agggttaacc cagcaagcta caaagagggt gtgtcacact gaaactcaat agttgagttt    6120
ggctgttgtt gcaggaaaat gattataact aaaagctctc tgatagtgca gagacttacc    6180
agaagacaca aggaattgta ctgaagagct attacaatcc aaatattgcc gtttcataaa    6240
tgtaataagt aatactaatt cacagagtat tgtaaatggt ggatgacaaa agaaaatctg    6300
ctctgtggaa agaaagaact gtctctacca gggtcaagag catgaacgca tcaatagaaa    6360
gaactcgggg aaacatccca tcaacaggac tacacacttg tatatacatt cttgagaaca    6420
ctgcaatgtg aaaatcacgt ttgctattta taaacttgtc cttagattaa tgtgtctgga    6480
cagattgtgg gagtaagtga ttcttctaag aattagatac ttgtcactgc ctatacctgc    6540
agctgaactg aatggtactt cgtatgttaa tagttgttct gataaatcat gcaattaaag    6600
taaagtgatg caacatcttg taaaaaaaaa aaaaaaaaa a                          6641
```